United States Patent
Park et al.

(10) Patent No.: US 9,187,725 B2
(45) Date of Patent: Nov. 17, 2015

(54) AUTOMATIC BIOLOGICAL SAMPLE PURIFICATION APPARATUS EQUIPPED WITH MAGNETIC FILED APPLYING PART, METHOD OF EXTRACTING TARGET SUBSTANCE FROM BIOLOGICAL SAMPLE, AND PROTEIN EXPRESSION AND PURIFICATION METHOD

(75) Inventors: Han-Oh Park, Daejeon (KR); Jong-Kab Kim, Daejeon (KR); Yang-Won Lee, Daejeon (KR); Jong-Hoon Kim, Daejeon (KR)

(73) Assignee: BIONEER CORPORATION, Daejeon (KR)

( * ) Notice: Subject to any disclaimer, the term of this patent is extended or adjusted under 35 U.S.C. 154(b) by 155 days.

(21) Appl. No.: 13/643,395

(22) PCT Filed: Apr. 29, 2011

(86) PCT No.: PCT/KR2011/003245
§ 371 (c)(1),
(2), (4) Date: Oct. 25, 2012

(87) PCT Pub. No.: WO2011/136624
PCT Pub. Date: Nov. 3, 2011

(65) Prior Publication Data
US 2013/0043191 A1    Feb. 21, 2013

(30) Foreign Application Priority Data
Apr. 30, 2010  (KR) .................. 10-2010-0040933

(51) Int. Cl.
*B03C 1/02*  (2006.01)
*C12M 1/32*  (2006.01)
*C12N 15/10*  (2006.01)

(52) U.S. Cl.
CPC ........... *C12M 33/06* (2013.01); *C12N 15/1003* (2013.01)

(58) Field of Classification Search
CPC .............. B03C 1/02; B03C 1/12; G01N 1/34; C02F 1/48; C02F 1/481; C02F 1/482; C12N 15/1003
USPC .................. 422/501, 504, 509, 518–521, 63, 422/65–68.1, 527; 210/695, 222; 436/174–175, 177, 178
See application file for complete search history.

(56) References Cited

U.S. PATENT DOCUMENTS

| 4,988,618 A | 1/1991 | Li et al. |
| 5,443,791 A | 8/1995 | Cathcart et al. |

(Continued)

FOREIGN PATENT DOCUMENTS

| EP | 1260583 A1 | 11/2002 |
| KR | 20040069368 A | 8/2004 |

OTHER PUBLICATIONS

International Search Report: mailed Dec. 21, 2011; PCT/KR2011/003245.

*Primary Examiner* — Brian R Gordon
(74) *Attorney, Agent, or Firm* — Ladas & Parry LLP

(57) ABSTRACT

An automatic biological sample purification apparatus is disclosed. The apparatus is equipped with a magnetic field applying part, in which the magnetic field applying part for purifying biological samples and a heating part are integrally formed with each other so as to be movable up and down. A method of extracting a target substance from the biological sample using the automatic biological sample purification apparatus equipped with the magnetic field applying part is also disclosed.

21 Claims, 39 Drawing Sheets

(56) References Cited

U.S. PATENT DOCUMENTS

| | | | |
|---|---|---|---|
| 5,789,251 A * | 8/1998 | Astle | 436/48 |
| 6,040,192 A | 3/2000 | Tuunanen | |
| 7,267,800 B2 * | 9/2007 | Takii et al. | 422/501 |
| 2004/0115720 A1 | 6/2004 | McWilliams et al. | |
| 2006/0133965 A1 * | 6/2006 | Tajima et al. | 422/100 |
| 2008/0009074 A1 * | 1/2008 | Valinsky | 436/180 |

* cited by examiner

AUTOMATIC BIOLOGICAL SAMPLE PURIFICATION APPARATUS EQUIPPED WITH MAGNETIC FILED APPLYING PART, METHOD OF EXTRACTING TARGET SUBSTANCE FROM BIOLOGICAL SAMPLE, AND PROTEIN EXPRESSION AND PURIFICATION METHOD

TECHNICAL FIELD

The present invention relates to an automatic purification apparatus for isolating target substances from multiple biological samples, and more particularly to an automatic biological sample purification apparatus equipped with a magnetic field applying part, in which the magnetic field applying part for purifying biological samples and a heating part are integrally formed with each other so as to be movable up and down.

Further, the present invention relates to a method of extracting a target substance from the biological sample using the automatic biological sample purification apparatus equipped with the magnetic field applying part.

BACKGROUND ART

Generally, a method using magnetic particles is widely used in order to isolate a target substance, such as nucleic acid and protein, from a biological sample. In this method, biochemical substances in the suspension state are rapidly attached to the fine magnetic particles having large surface areas, and the magnetic field is applied so as to collect the magnetic particles on which the target substance are attached, and then a solution thereof is removed. And various automatic equipments associated with this method have been developed.

Recently, an automated method using pipettes has been used widely.

U.S. Pat. No. 5,647,994 (claiming a priority date of Jun. 21, 1993) filed by Labsystems Oy describes various methods of separating the magnetic particles using a disposable pipette. These methods are prior arts for collecting the magnetic particles in the pipette like in U.S. Pat. Nos. 5,702,950 and 6,187,270. And the construction elements thereof includes a tubular member serially connected to a jet channel, the jet channel defining a flow port at a free end of the tubular member and also having a diameter that is less than a diameter of a separation chamber; and a magnetic element disposed at one of a first location adjacent to the outer side of the separation wall and a second location within the separation chamber, wherein the magnetic element is adapted to be brought into such a state that magnetic particles will gather under the influence of magnetic field when disposed in a first location, or into such a state that the magnetic field no longer keeps the magnetic particles when disposed in a second location, and wherein the tubular member includes a second portion defining a cylindrical channel serially connected to the separation chamber on a side remote from the jet channel, the cylindrical channel receiving a movable piston thereby defining a suction cylinder for drawing liquid into the separation chamber and for removing the liquid from the separation chamber through the jet channel via the flow port.

A magnetic substance attracting/releasing control method proposed by Precision System Science Co. Ltd (U.S. Pat. Nos. 5,702,950 and 6,231,814) has the same fundamental principle as in U.S. Pat. No. 5,647,994, except that a magnet is attached and detached in one direction of the pipette and thus magnetic field is controlled in one direction of a pipette tip. This magnetic substance attracting/releasing control method comprises the steps of: providing a pipette device having a liquid suction line including a liquid inlet end for sucking liquid containing the magnetic substance from a container and discharging the liquid through the liquid inlet end, and a magnet body or magnet bodies being detachably fitted to an external peripheral surface of the liquid suction line of the pipette device; the pipette device providing attracting/releasing control by absorbing and maintaining the magnetic substance contained in the liquid and attracted to the liquid suction line due to magnetism in the magnet body or bodies on an internal surface of the liquid suction line, the magnetic substance being maintained on the internal surface of the pipette device and also by releasing the magnetic substance from the liquid suction line by means of interrupting effect by magnetism in the magnet body or bodies so that the substance is discharged together with the liquid to outside of the liquid suction line through the liquid inlet end.

In U.S. Pat. No. 6,187,270 (Roche Diagnostics GmbH), there is disclosed a method of separation of magnetic particles, in which a permanent magnet is approached to a disposable tip so as to attach the magnetic particles, thereby separating the magnetic particles from a solution. To this end, an apparatus for separation of the magnetic particles includes a pipette connected to a pump, a magnet, and a means for moving the magnet to the pipette side or the opposite side thereof. According to claim 1 of this patent, it is characterized in that a device for separating magnetic microparticles from a suspension in a liquid comprises a pipette having an inner wall, the pipette containing a suspension of magnetic microparticles in a liquid therein, as pipette contents, wherein the pipette is configured to be rotatable about a longitudinal axis thereof; a pump connected to the pipette; a magnet exterior of the pipette and locatable to apply a magnetic field to at least part of the pipette contents to deposit the microparticles on the inner wall of the pipette; and moving means for causing relative movement of the pipette and the magnet to move at least one of them toward the other. According to claim 2 thereof, it is characterized in that the device comprises a pipette having an inner wall, the pipette containing a suspension of magnetic microparticles in a liquid therein as pipette contents; a pump connected to the pipette; a magnet exterior of the pipette and locatable to apply a magnetic field to at least part of the pipette contents to deposit the microparticles on the inner wall of the pipette; and moving means for causing relative movement of the pipette and the magnet to move at least one of them toward the other, wherein the magnet is configured to be movable around a longitudinal axis of the pipette. In the device of claim 2, the magnet is formed to be movable around the longitudinal axis of the pipette instead of the rotation of the pipette. And according to a third independent claim of this patent, it is characterized in that the pipette and magnet are movable relative to one another so that the magnetic field deposits microparticles on the inner wall in order to collect and eject magnetic microparticles deposited on the inner wall of the pipette in the pipette tip.

In these structures, there have been proposed methods of separating the magnetic particles from a solution using a disposable pipette and then suspending them in other solution. Herein, however, there is a serious problem that a lower end of the pipette may be clogged with the magnetic particles and thus an inaccurate result may be occurred frequently. Further, since a series of processes for separating a target substance from a biochemical mixed liquid is carried out in a pipette, it is difficult to uniformly maintain a suspension of a liquid, and also since alcohol is not completely removed even after a final step of cleaning alcohol, there is another problem that the alcohol is remained upon elution and thus may exert an influence on other post-process such as PCR.

In order to solve these problems, there has been developed again a special method in which a process of catching and collecting magnetic substances from a liquid is performed in a sample vessel instead of a pipette. The method in which a reaction is carried out in the sample vessel had been proposed already before.

Gen-Probe, Inc. also discloses a method of separating magnetically attractable particles from a fluid using a magnetic separation rack. The magnetic separation rack includes a plurality of test tube retaining portions, and a plurality of magnets arranged such that each magnet is alternately located at one side of the test tube. Herein, the magnet is arranged to one side of the test tube and at an upper portion thereof but not contacted with a bottom surface thereof. The magnetically labeled particles are attracted to the side of the test tube and then rinsed or removed with a liquid, thereby performing quantitative analysis thereof. However, since the magnetic particles in the test tube cannot sensitively response to the magnetic separation rack, there is a disadvantage in that the purification efficiency is deteriorated.

Amersham International plc had developed a method which can switch a magnet filed by moving a doughnut-shaped magnet vertically to a vessel (U.S. Pat. No. 5,897,783). And Beckman instruments, Inc. had developed an automatic purification apparatus for separating a magnetic substance from a sample using a magnetic plate (EP0479448). The magnetic plate is formed into a plate having a plurality holes through which a vessel can be inserted, and the automatic purification apparatus includes meaning for moving the magnetic plate up and down.

In case that the magnet has to be manufactured according to a certain shape and size, such as a doughnut and a plate, it is difficult to manufacture it and the manufacturing cost is increased. Thus, it is economically infeasible.

In case of using a commercially available rod magnet, it is advantageous to fabricate the apparatus. Gene-Trak systems had proposed a magnetic separation device using such the rod magnet (EP0317286). The magnetic separation apparatus includes base means having a plurality of orifices for receiving nonferrous containers adapted to contain magnetic particles; and a plurality of magnet means mounted on the said base spaced about the periphery of each receiving orifice wherein each of the said magnet means possess a north-south magnetic field orientation in a direction which is coplanar with a cross-sectional plane through the receiving orifices and wherein each of the north-south magnet fields of the magnet means are oriented in a common direction. However, in this system, there is not disclosed a method of minutely controlling up and down movements of the magnet means.

Meanwhile, temperature controlling in purification of a biological sample is one of the very important parameters. The optimal active temperature of protease K which is generally applied upon lysis is 55~65, and the temperature controlling is essential in the purification. Further, after the final step of cleaning alcohol, it is preferable to completely dry and remove the alcohol. If the alcohol is not completely removed, other post-process such as PCR is influenced by the alcohol remained even after elution. Therefore, it is necessary to perform a high temperature treatment, thereby completely removing the alcohol.

Nevertheless, in the existing automatic purification apparatuses, temperature controlling means for improving the purification efficiency is not considered yet. Generally, the existing automatic systems which have been developed until now do not treat the lysis step at all which needs the temperature controlling. Even though the temperature controlling is carried out, the sample has to be moved to a new block in which the temperature controlling can be performed and then reacted therein. However, in this case, loss of the sample is inevitable due to the frequent movement of the sample.

Furthermore, in protein expression outside of cells, it is essential to control the temperature into 30~40° C. and properly maintain the temperature for 3 hours or more. In a test tube, enzyme activity has to be occurred in all processes that RNA is synthesized from DNA and a protein is synthesized from the RNA. Herein, the above-mentioned reactions are carried out only when the temperature is maintained into 30~40° C.

Also in case of using the above-mentioned pipettes, it is actually impossible to control the temperature due to its structural problem.

Therefore, in order to purify the biological sample using the magnetic particles, there is an increasing necessity for a new automatic purification apparatus in which the magnetic field is applied to the outside of a test tube, not a pipette and its up and down movement and temperature can be controlled and also which can be facilely fabricated.

DISCLOSURE

Technical Problem

An object of the present invention is to provide an automatic purification apparatus which can moves up and down a magnet mounting part and a heating part and thus can apply and release magnetic field and also can control temperature.

Another object of the present invention is to provide an automatic purification apparatus in which a plurality of unit well inserting grooves formed in the magnet mounting part are formed so as to enclose a lower portion of each unit well of a multi-well plate, thereby improving reaction efficiency.

Yet another object of the present invention is to provide an automatic purification apparatus which can prevent solution drips undesirably fallen from a plurality of pipettes from being introduced into the unit wells of the multi-well plate.

Yet another object of the present invention is to provide an automatic purification apparatus which can maintain nucleic acid received in a target substance receiving tube and a diagnostic kit or a diagnostic reagent received in a target substance diagnosing tube at a low temperature, e.g., 3~5° C.

Yet another object of the present invention is to provide an automatic purification apparatus which can prevent the multi-well plate from being separated upward when the pipettes installed at the pipette block is moved up and down so as to access to the unit wells of the multi-well plate.

Yet another object of the present invention is to provide an automatic purification apparatus which can automatically mix purified nucleic acid and the diagnostic kit or the diagnostic reagent received in the target substance diagnosing tube using the plurality of pipettes.

Yet another object of the present invention is to provide an automatic purification apparatus which can perform the expression and purification of protein as the target substance from the biological samples using the plurality of pipettes installed at the pipette block.

Yet another object of the present invention is to provide an automatic purification apparatus in which heat transfer is occurred from a heating part to an auxiliary heating part enclosing a particular unit well of the multi-well plate, thereby efficiently heating the particular unit well of the multi-well plate.

Yet another object of the present invention is to provide an automatic purification apparatus in which a contamination preventing device can block an upper end of the target substance receiving tube and thus aerosol generated from purified nucleic acid is prevented from being spread to the outside of the target substance receiving tube when the purified nucleic acid is discharged from the plurality of pipettes.

Technical Solution

To achieve the object of the present invention, the present invention provides an automatic purification apparatus for isolating a target substance from a plurality of biological samples, comprising a pipette block 100 which is disposed to be moved vertically and horizontally and in which a plurality of pipettes 141, 142 for sucking and discharging a fluid material are removably installed; and a magnetic field applying part 700 which is mounted on a base plate 400 so as to apply and release magnetic field to a particular unit well of a multi-well plate 420, 420' located at a lower side of the pipette block 100.

Preferably, the magnetic field applying part 700 comprises a magnet mounting part 710 on which a magnet 711 is mounted and which is located at a lower side of the particular unit well of the multi-well plate 420, 420'; and a lifting part 760 which lifts up and down the magnet mounting part 710 so as to apply and release magnetic field to the particular unit well of the multi-well plate 420, 420'. Further, a unit well inserting groove 713 is formed at an upper surface of the magnet mounting part 710 so that the lower portion of the particular unit well of the multi-well plate 420, 420' is inserted therein, and the base plate 400 is formed with a unit well exposing hole 400-3 so that the lower portion of the particular unit well of the multi-well plate 420, 420' is inserted in the unit well inserting groove 713 when the magnet mounting part 710 is lifted up, and also the magnet 711 is installed around the unit well inserting groove 713.

Preferably, the present invention may further comprise a heating part 810 for heating the particular unit well of a multi-well plate 420, 420', and the magnetic field applying part 700 comprises a magnet mounting part 710 on which a magnet 711 is mounted and which is located at a lower side of the particular unit well of the multi-well plate 420, 420'; and a lifting part 760 which lifts up and down the magnet mounting part 710 so as to apply and release magnetic field to the particular unit well of the multi-well plate 420, 420', and the heating part 810 is installed at the magnet mounting part 710. Further, the heating part 810 may be a heat generating film which is contacted with the magnet mounting part 710.

Preferably, the present invention may further comprise a fixed body 200 which supports the pipette block 100; and a solution drip tray 510 which is disposed to be horizontally moved by a solution drip tray moving means installed at the fixed body 200 and thus located at a lower side of the plurality of pipettes 141 and 142 installed at the pipette block 100 when the pipette block 100 is moved horizontally, and also may further comprises an aerosol prevention part 1070 which is tightly contacted with the solution drip tray 510 located at the lower side of the plurality of pipettes 141 and 142 so as to enclose portions of the pipettes 141 and 142, which are wetted with a solution containing the target substance, such that the portions of the pipettes 141 and 142, which are wetted with the solution containing the target substance, can be blocked from the outside.

Preferably, a pipette rack 430 in which the plurality of pipettes 141 and 142 to be installed at the pipette block 100 are received, a first tube rack 440 which receives a plurality of target substance receiving tubes 442-1 for receiving the target substance, and a waste liquid container 450 which collects waste liquid discharged from the plurality of pipettes 141 and 142 installed at the pipette block 100 are mounted on the base plate 400. Further, a cooling block 441 for cooling the first tube rack 440 may be mounted on the base plate 400.

Further, the present invention provides a method of extracting a target substance from a biological sample using the automatic purification apparatus, wherein, in case that a mixture except magnetic particles on which the target substance and impurities are attached is removed from a first mixture containing the magnetic particles on which the target substance and impurities are attached using the pipettes 141 and 142, in case that a mixture except magnetic particles on which the target substance is attached is removed from a second mixture containing the magnetic particles on which the target substance is attached using the pipettes 141 and 142, and in case that a mixture except magnetic particles is obtained from a third mixture containing the magnetic particles and the target substance separated from the magnetic particles using the pipettes 141 and 142, magnetic field is applied to lower portions of wells of the multi-well plate 420, 420' in which the first, second and third mixtures are injected, using the magnetic field applying part 700.

Further, the present invention provides an automatic purification apparatus for isolating a target substance from a plurality of biological samples, comprising a pipette block 100 which is disposed to be moved vertically and horizontally and in which a plurality of pipettes 141, 142 for sucking and discharging a fluid material are removably installed; a magnet mounting part 710 on which a magnet 711 for applying magnetic field to a particular unit well of a multi-well plate 420 and 420' mounted on a base plate 400 and located at a lower side of the pipette block 100 is mounted, and which is located at a lower side of the particular unit well of the multi-well plate 420, 420'; a lifting part 760 which lifts up and down the magnet mounting part 710 so as to apply and release the magnetic field to the particular unit well of the multi-well plate 420, 420'; a heating part 810 which is installed at the magnet mounting part 710 so as to heat the magnet mounting part 710; and an auxiliary heating part 820 in which the particular unit well of the multi-well plate 420, 420' is inserted and of which a lower surface is contacted with an upper surface of the magnet mounting part 710 when the magnet mounting part 710 is moved up.

Preferably, the auxiliary heating part 820 comprises a first body 821 which is contacted with an outer surface of one side of the particular unit well of the multi-well plate 420, 420'; a second body 822 which is contacted with an outer surface of the other side of the particular unit well of the multi-well plate 420, 420'; and a tightly-contacting spring 824 which presses the second body 822 toward the first body 821 so that the outer surface of the particular unit well of the multi-well plate 420, 420' is tightly contacted with the first and second bodies 821 and 822, and a unit well inserting groove 713 is formed at an upper surface of the magnet mounting part 710 so that the lower portion of the particular unit well of the multi-well plate 420, 420' is inserted therein, and the base plate 400 is formed with a unit well exposing hole 400-3 so that the lower portion of the particular unit well of the multi-well plate 420, 420' is inserted in the unit well inserting groove 713 when the magnet mounting part 710 is moved up. Further, the heating part 810 may be a heat generating film which is contacted with the magnet mounting part 710.

Further, the present invention provides a method of extracting a target substance from a biological sample using the automatic purification apparatus, comprising a mixing step S1010, S1020, S1030 of mixing the biological sample with a cell lysis solution injected into a well of the multi-well plate 420, 420' using the pipette 141, 142; a first heating step S1040 of heating the particular unit well of the multi-well plate 420, 420' using the heating part 720 while the magnet mounting part 710 is lifted up and thus heating the biological sample; a binding solution mixing step S1050 of mixing a mixture of the cell lysis solution and the biological sample with a binding solution injected into the well of the multi-well plate 420, 420' using the pipette 141, 142; an aqueous dispersion solution of magnetic particles mixing step S1060 of mixing a mixture of the binding solution with an aqueous dispersion solution of magnetic particles injected into the well of the multi-well plate 420, 420' using the pipette 141, 142; a first magnetic field applying step S1080 of lifting up the magnet mounting part 710 and then applying magnetic field from the magnet 710 to a lower portion of the particular unit well of the multi-well plate 420, 420' in which a mixture of the aqueous dispersion solution of magnetic particles is received; a first removing step S1090 of removing a mixture except the magnetic particles and a substance attached on the magnetic particles from the mixture of the aqueous dispersion solution of magnetic particles using the pipette 141, 142, while the magnetic particles and the substance attached on the magnetic particles in the mixture of the aqueous dispersion solution of magnetic particles are attached to a lower inner surface of the particular unit well; a third injecting and washing step S1100 of injecting a washing solution injected into the well of the multi-well plate 420, 420' to the particular unit well of multi-well plate 420, 420' using the pipette 141, 142 and thus washing and separating impurities except the target substance from the magnetic particles; a second removing step S1120 of removing a mixture except the magnetic particles on which the target substance is attached from the mixture of the washing solution using the pipette 141, 142, while the magnetic particles on which the target substance is attached in the mixture of the washing solution are attached to the lower inner surface of the particular unit well of the multi-well plate 420, 420'; a fourth injecting and nucleic acid isolating step S1140 of injecting an nucleic acid elution solution injected into the well of the multi-well plate 420, 420' to the particular unit well of multi-well plate 420, 420' using the pipette 141, 142 and thus separating the target substance from the magnetic particles; and a target substance containing solution obtaining step S1160 of obtaining a target substance containing solution except the magnetic particles from the nucleic acid elution solution containing the target substance separated from the magnetic particles using the pipette 141, 142, while the magnetic particles in the nucleic acid elution solution containing the target substance separated from the magnetic particles are attached to the lower inner surface of the particular unit well of multi-well plate 420, 420'.

Preferably, the washing solution includes alcohol, and the present invention may further comprise a second heating step S1130 of heating the lower portion of the particular unit well of multi-well plate 420, 420' using the heating part 720 and thus removing alcohol contained in the washing solution remained in the magnetic particles, while the magnet mounting part 710 is lifted up before the fourth injecting and nucleic acid isolating step S1140 and the lower portion of the particular unit well of multi-well plate 420, 420' is inserted into the unit well inserting groove 713. And the target substance containing solution obtaining step S1160 may comprise a step of injecting the target substance containing solution into a target substance receiving tube 442-1 or a target substance diagnosing tube 442-3 installed at the base plate 400 using the pipette 141, 142.

Further, the present invention provides an automatic purification apparatus for isolating a target substance from a plurality of biological samples, comprising a pipette block 100 which is disposed to be moved vertically and horizontally and in which a plurality of pipettes 141, 142 for sucking and discharging a fluid material are removably installed; a magnetic field applying part 700 which is mounted on the base plate 400 so as to apply magnetic field to a particular unit well of the multi-well plate 420, 420' located at a lower side of the pipette block 100; a first tube rack 440 which is mounted on the base plate 400 so as to receive a target substance tube 442-1, 442-3 for receiving the target substance; and a contamination preventing device 460 which is mounted on the base plate 400 so as to block an upper end of the target substance tube 442-1, 442-3, so that aerosol generated from the target substance discharged from the plurality of pipettes 141 and 142 is prevented from being spread to an outside of the target substance tube 442-1, 442-3.

Preferably, the contamination preventing device 460 comprises a cover film 461 having a cut line 461-1 which is gaped by pressing force of the plurality of pipettes 141 and 142 so as to allow the lower portions of the pipettes 141 and 142 to be passed therethrough; and a film supporter which is mounted on the base plate 400 so that the cut line 461-1 is located at an upper side of the target substance tube 442-1, 442-3. And the film supporter comprises a settle plate 463 on which the cover film 461 is settled and which is formed with a through-hole 463-1 through which an upper end of the target substance tube 442-1, 442-3 is inserted; and a horizontal movement preventing plate 465 which is installed at an upper surface of the settle plate 463 so as to prevent a horizontal movement of the cover film 461 by contacting an outer surface of the cover film 461. Further, the film supporter comprises a vertical movement preventing plate 467 which is installed at an upper surface of the cover film 461 so as to prevent a vertical movement of the cover film 461 and also formed with an exposing hole 467-1 for exposing the cut line 461-1 of the cover film 461, and the film supporter comprises a settle plate supporter 469 which is inserted onto the first tube rack 440 so that a lower end of the settle plate supporter 469 is installed at the base plate 400, and of which an upper end is connected with the settle plate 463.

Preferably, a foil 462 which can be punched by pressing force of the pipettes 141 and 142 is disposed between the settle plate 463 and the cover film 461, and the target substance tube 442-1, 442-3 comprises at least one of a target substance receiving tube 442-1 and a target substance diagnosing tube 442-3.

Preferably, the present invention may further comprises a waste liquid container 450 which receives waste liquid discharged from the pipettes 141 and 142 installed at the pipette block 100, and which is mounted on the base plate 400 being adjacent to a unit well exposing hole 400-3 with which the base plate 400 is formed so that the magnetic field applying part 700 is lifted up so as to apply the magnetic field to the lower portion of the particular unit well of the multi-well plate 420, 420', and a second tube rack 470 which is disposed so as to be faced with the unit well exposing hole 400-3 with waste liquid container 450 in the center and also to be adjacent to the waste liquid container 450, and which receives a biological sample tube 472 in which a biological sample is injected.

Further, the present invention provides a protein expression and purification method which can automatically expressing and isolating protein using the automatic purification apparatus.

Advantageous Effects

According to the automatic purification apparatus of the present invention, it is possible to move up and down a magnet mounting part and a heating part, thereby applying and releasing the magnetic field and also controlling the temperature.

Since a plurality of unit well inserting grooves formed in the magnet mounting part are formed so as to enclose a lower portion of each unit well of a multi-well plate, it is possible to improve the reaction efficiency.

According to the automatic purification apparatus of the present invention, since it is possible to stably isolate the target substance while basically preventing cross contamination due to the aerosol generated from the biological sample, the automatic purification apparatus can be properly used for clinical specimens.

According to the present invention, it is possible to prevent solution drips undesirably fallen from the plurality of pipettes from being introduced into the unit wells of the multi-well plate, thereby stably isolating the target substance.

Further, it is possible to maintain nucleic acid received in the target substance receiving tube and the diagnostic kit or diagnostic reagent received in the target substance diagnosing tube at a low temperature, e.g., 3~5° C.

Further, it is possible to prevent the multi-well plate from being separated upward when the pipettes installed at the pipette block is moved up and down so as to access to the unit wells of the multi-well plate.

Furthermore, it is possible to automatically mix the purified target substance and the diagnostic kit or diagnostic reagent received in the target substance diagnosing tube using the plurality of pipettes.

Further, since the heat transfer is occurred from the heating part to the auxiliary heating part enclosing the particular unit well of the multi-well plate, it is possible to efficiently heat the particular unit well of the multi-well plate.

Further, since the contamination preventing device can block an upper end of the target substance receiving tube, the aerosol generated from the purified target substance can be prevented from being spread to the outside of the target substance receiving tube when the purified target substance is discharged from the plurality of pipettes.

DESCRIPTION OF DRAWINGS

The above and other objects, features and advantages of the present invention will become apparent from the following description of preferred embodiments given in conjunction with the accompanying drawings, in which.

[Detailed Description of Main Elements]

| | |
|---|---|
| 100: pipette block | 121, 122: syringe pin |
| 130: syringe pin guiding block | 131, 132: syringe pin guiding hole |
| 131-1, 132-1: X-ring | 133, 134: pipette mounting part |
| 133-1, 134-1: communicating hole | 140, 141, 142: pipette |
| 200: fixed body | 400: base plate |
| 400-3: unit well exposing hole | 420, 420' : multi-well plate |
| 430: pipette rack | 440: first tube rack |
| 441: cooling block | 441-1: cooling water inlet line |
| 441-2: cooling water outlet line | 442-1: target substance receiving tube |
| 442-3: target substance diagnosing tube | 450: waste liquid container |
| 460: contamination preventing device | 461: cover film |
| 461-1: cutting line | 462: foil |
| 463: settle plate | 463-1: through-hole |
| 465: horizontal movement preventing plate | |
| 467: vertical movement preventing plate | |
| 467-1: exposing hole | 469: settle plate supporter |
| 470: second tube rack | 472: biological sample tube |
| 510: solution drip tray | |
| 521: pinion | 531: rack |
| 533: rack supporter | 533-1: rack supporter guiding hole |
| 535: rack supporter guiding rod | |
| 700: magnetic field applying part | 710: magnet mounting part |
| 711: magnet | 713: unit well inserting groove |
| 720: magnet mounting part supporter | 730: guiding rod |
| 740: guide block | 750: tension spring |
| 760: lifting part | 761: lifting motor |
| 762: first lifting shaft | 763: lifting cam |
| 764: second lifting shaft | |
| 810: heating part | 820: auxiliary heating part |
| 821: first body | 822: second body |
| 823: sliding rod | 824: tightly-contacting spring |
| 1151-G: insertion groove | |
| 1251, 1351: lower plate for solution drip tray | |
| 1253, 1353-1, 1353-2: side plate for solution drip tray | |
| 1373-1, 1373-2: side plate for aerosol prevention part | |
| 1050: solution drip tray | 1070: aerosol prevention part |

BEST MODE

Hereinafter, the embodiments of the present invention will be described in detail with reference to accompanying drawings.

First Embodiment

A first embodiment relates to an automatic purification apparatus equipped with a magnetic field applying part, which can isolate a target substance reversibly bound with magnetic particles from a plurality of biological samples using the magnetic particles.

Figure 1:
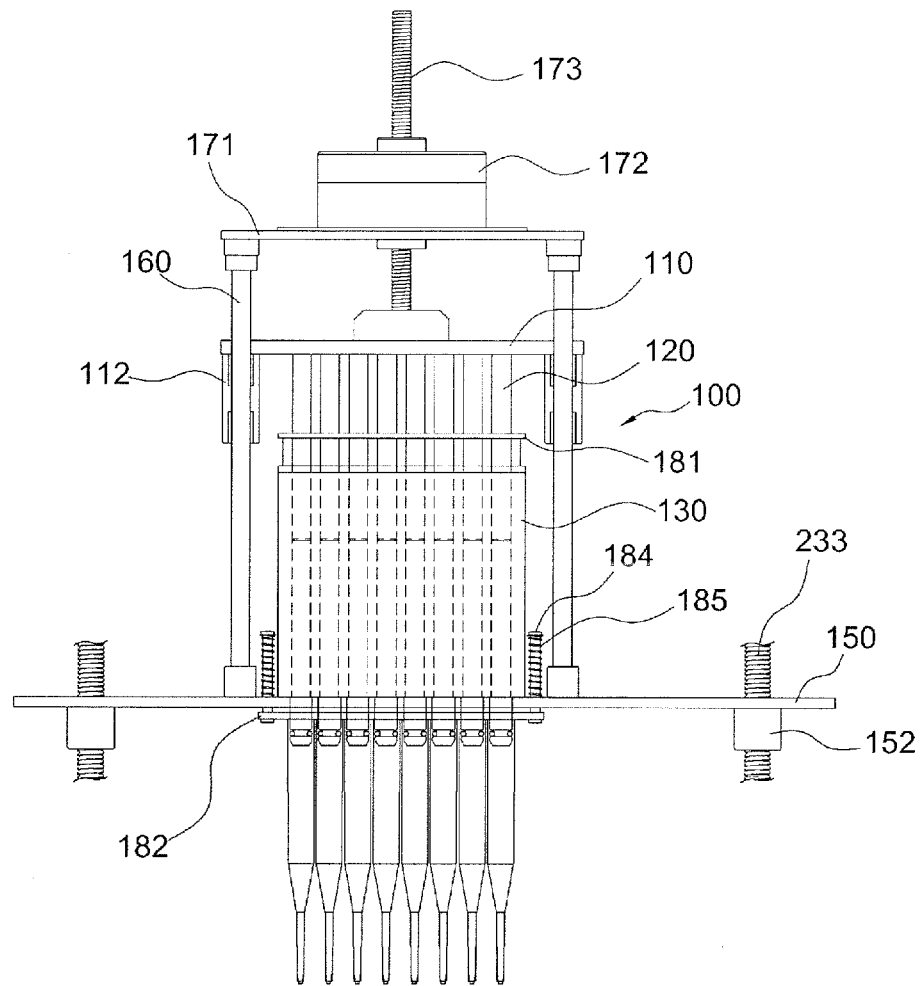
FIG. 1 is a schematic view of a pipette block according to a first embodiment of the present invention.
Figure 2:
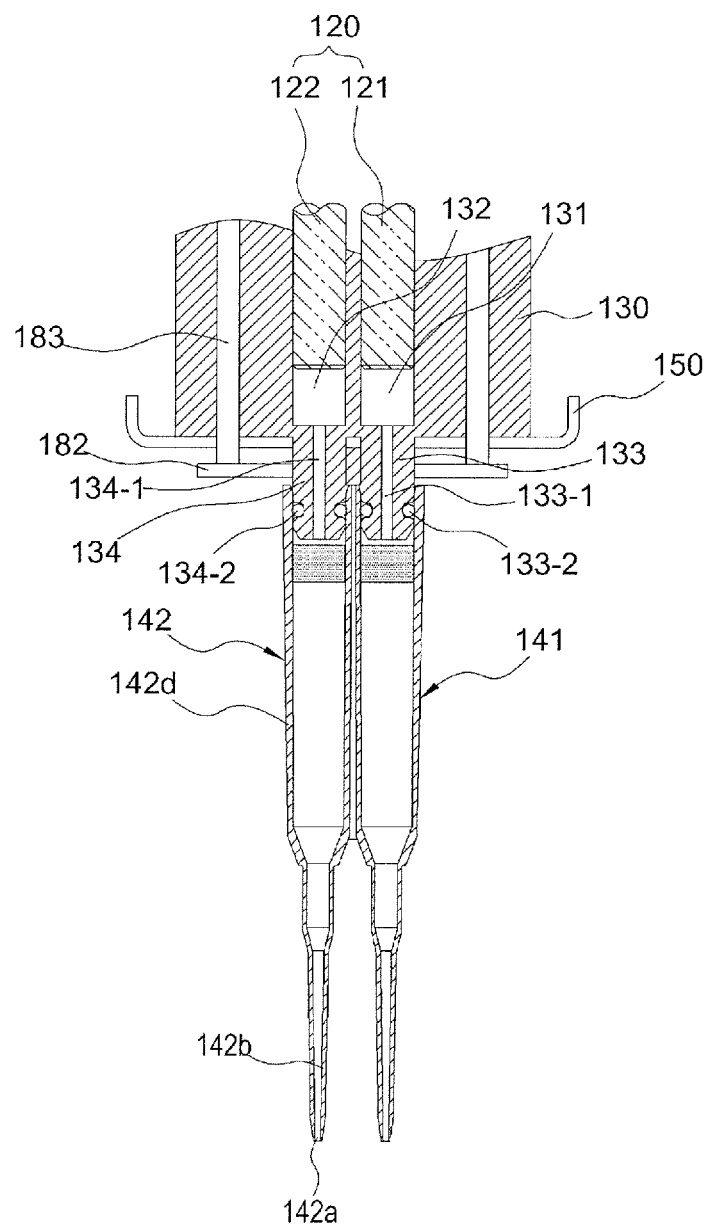
FIG. 2 is a side view of a main part of the pipette block according to the first embodiment of the present invention.
Figure 3:
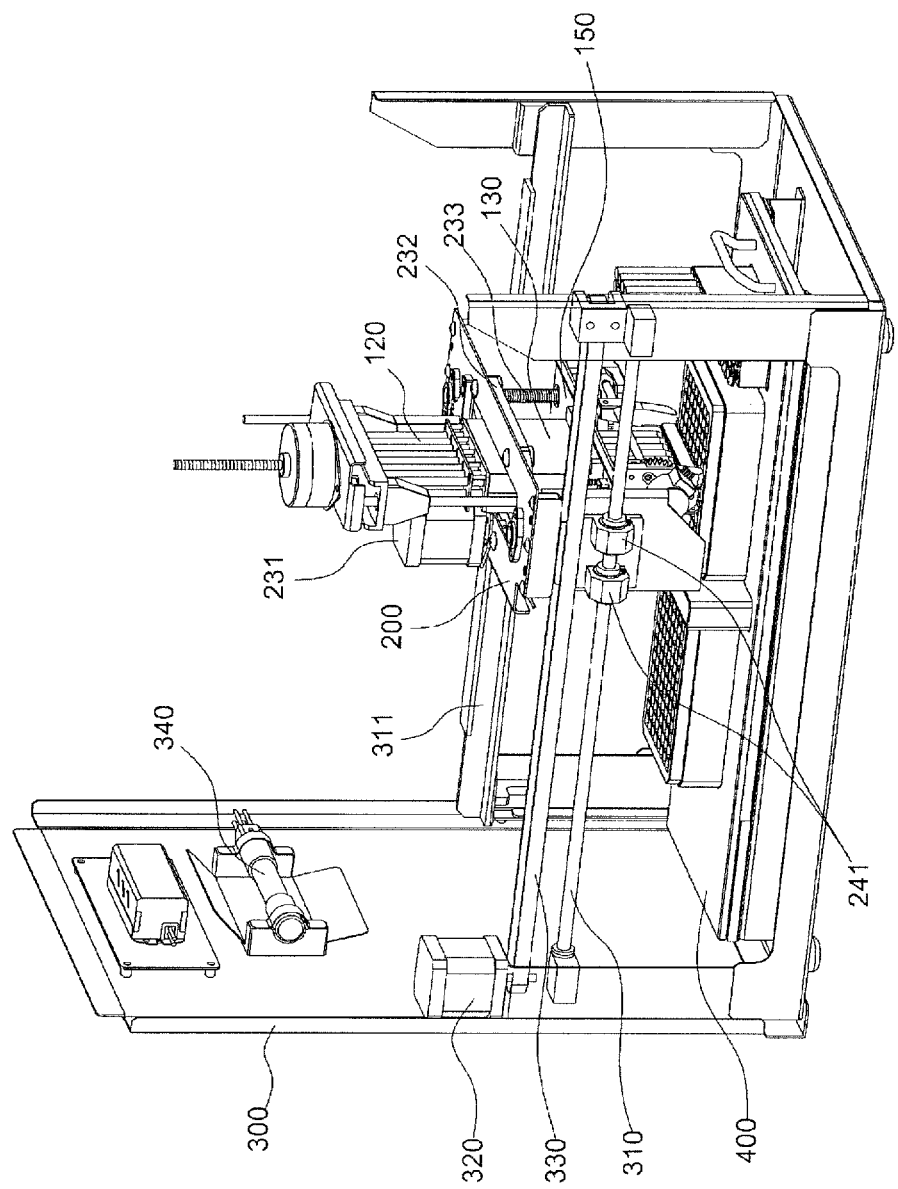
FIG. 3 is a schematic view of the first embodiment of which a casing is partially cut away.
Figure 4:
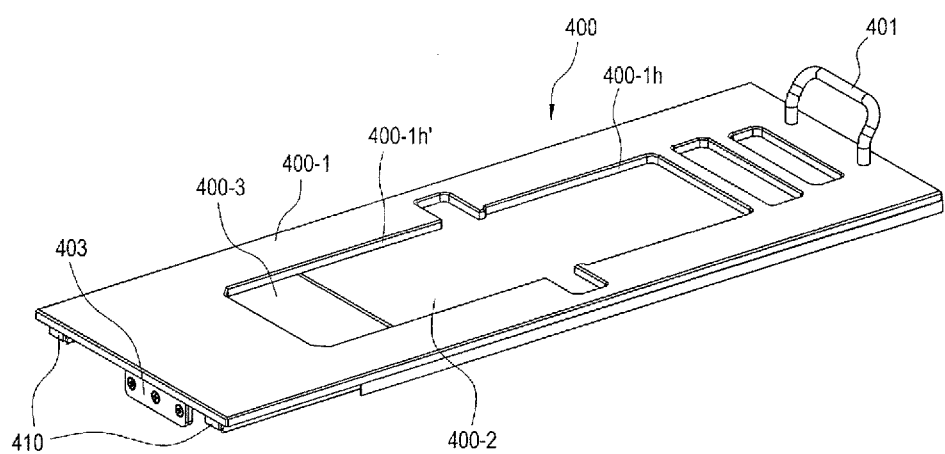
FIG. 4 is a perspective view of a base plate according to the first embodiment of the present invention.
Figure 5:
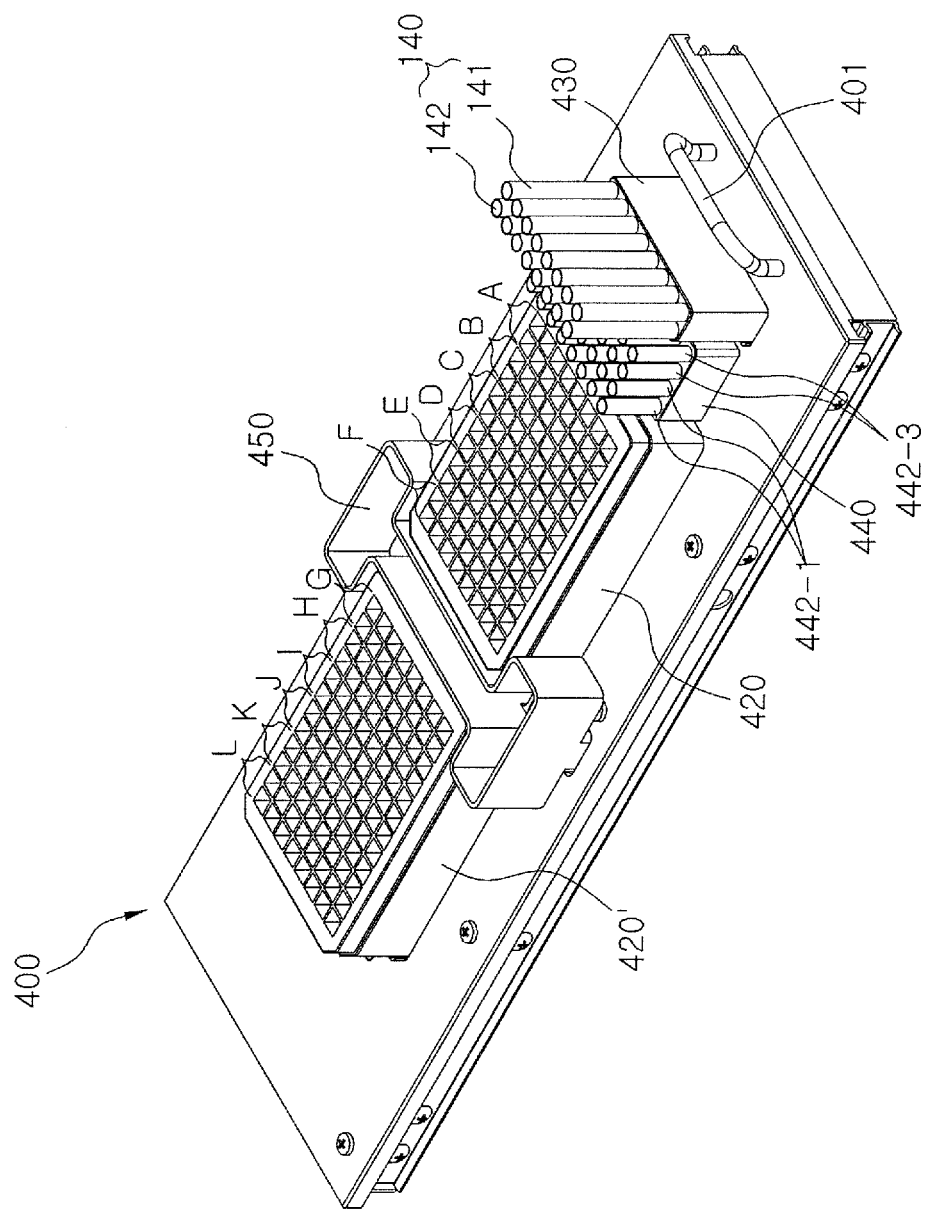
FIG. 5 is a view showing a using state of the base plate according to the first embodiment of the present invention.
Figure 6:
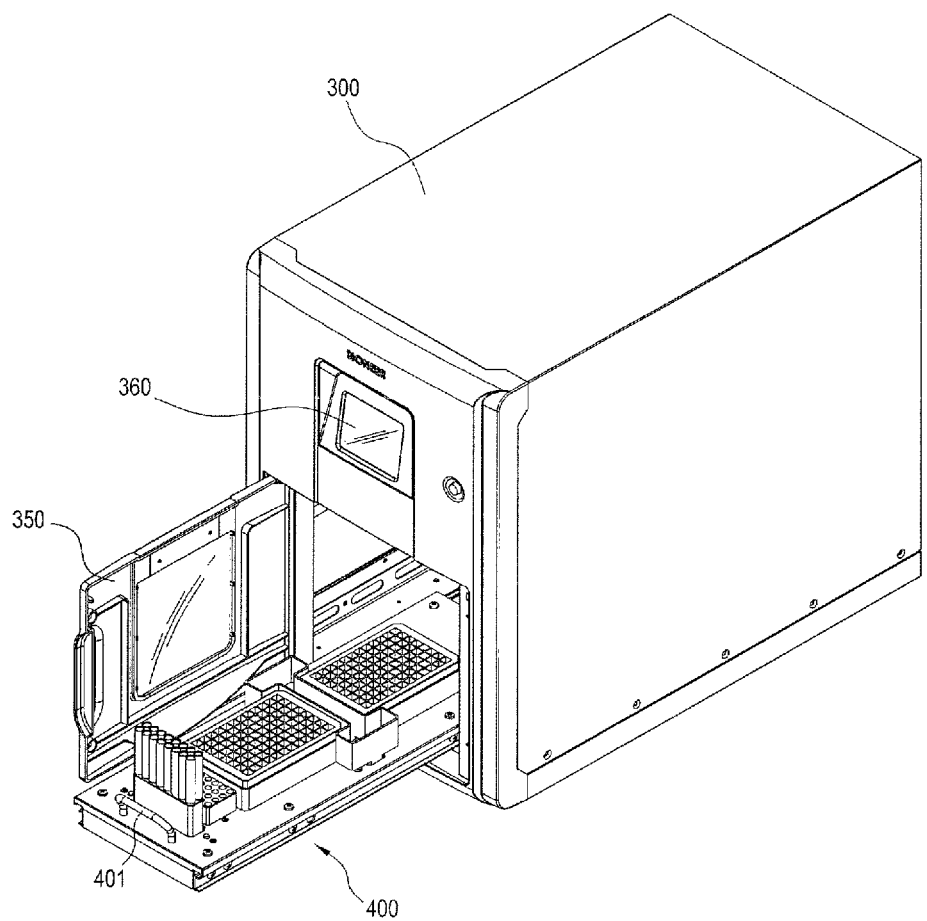
FIG. 6 is a view showing a state that the base plate is inserted into a casing according to the first embodiment of the present invention.
Figure 7:
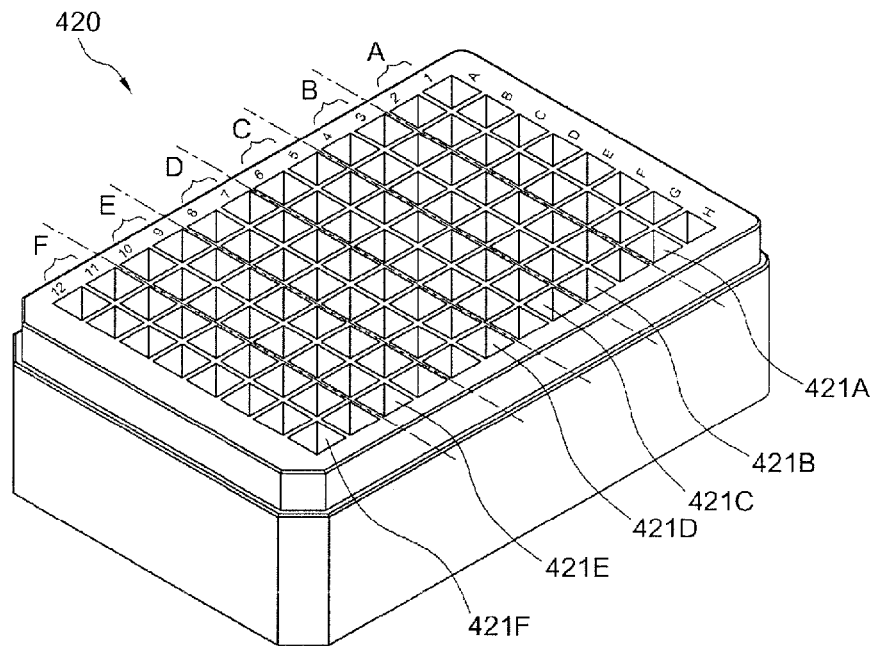
FIG. 7 is a perspective view of a multi-well plate according to the first embodiment of the present invention.
Figure 10:
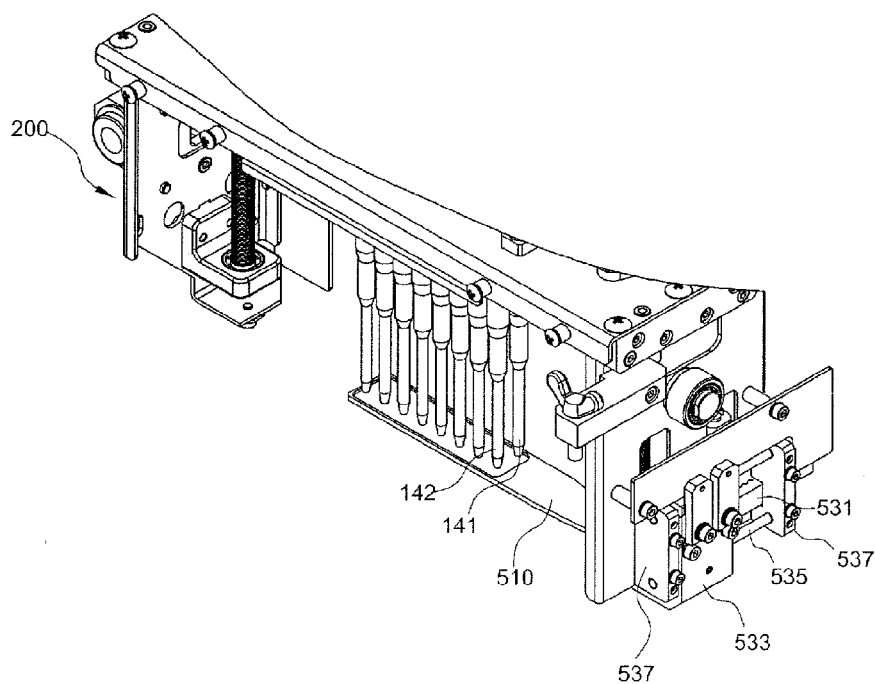
Figure 11:
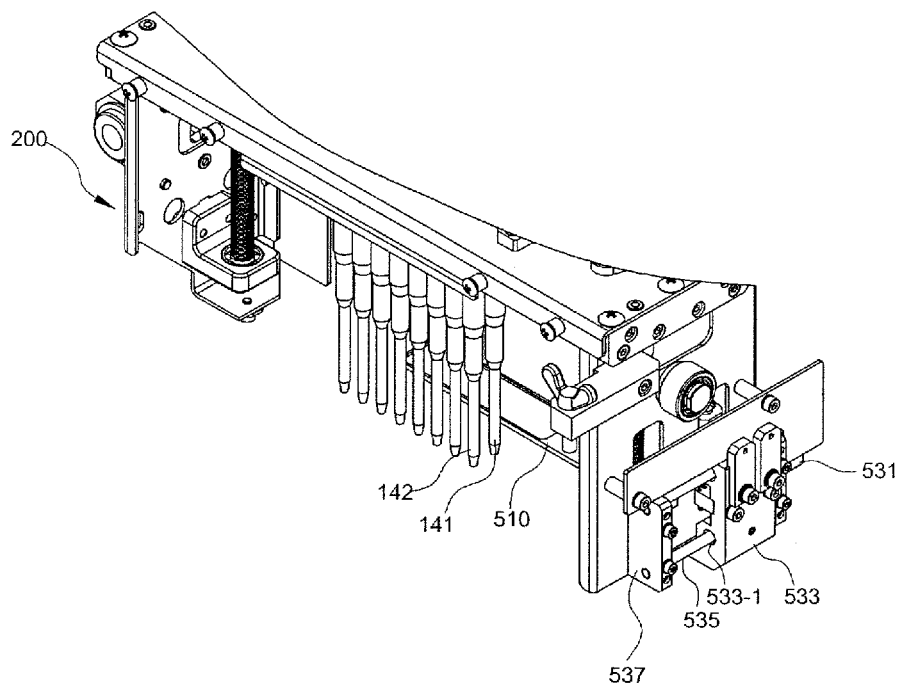
Figure 12:
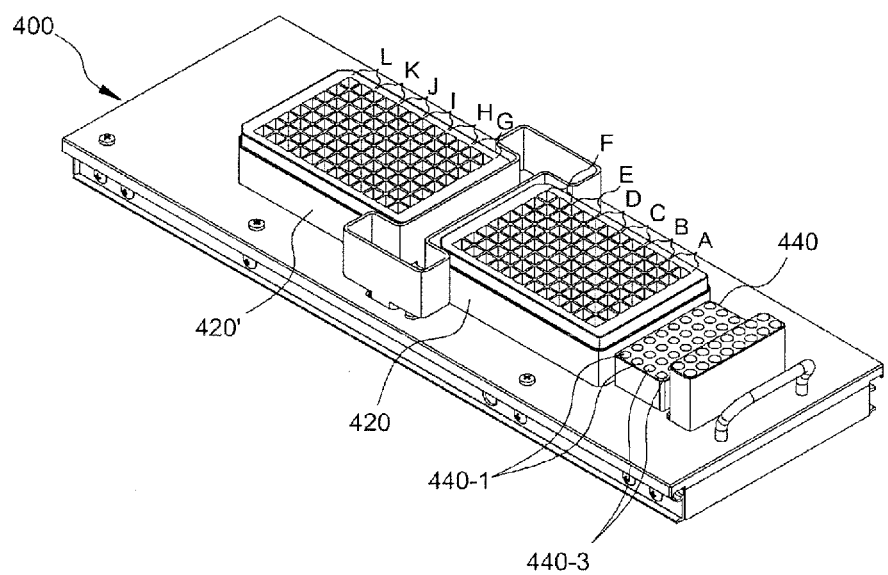
FIG. 12 is a view showing a state that a first tube rack is installed at the base plate according to the first embodiment of the present invention.
Figure 13:
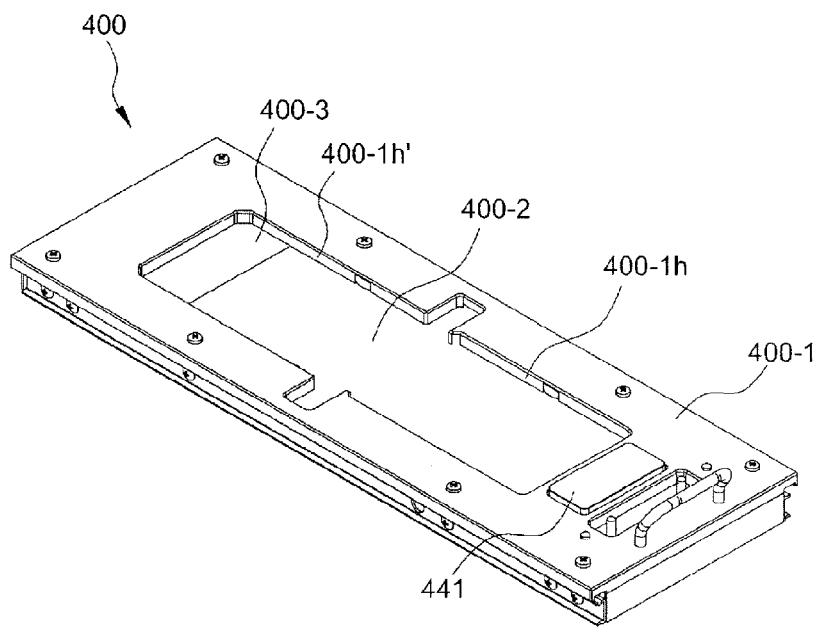
FIG. 13 is a view showing a state that a cooling block is installed at the base plate according to the first embodiment of the present invention.
Figure 14:
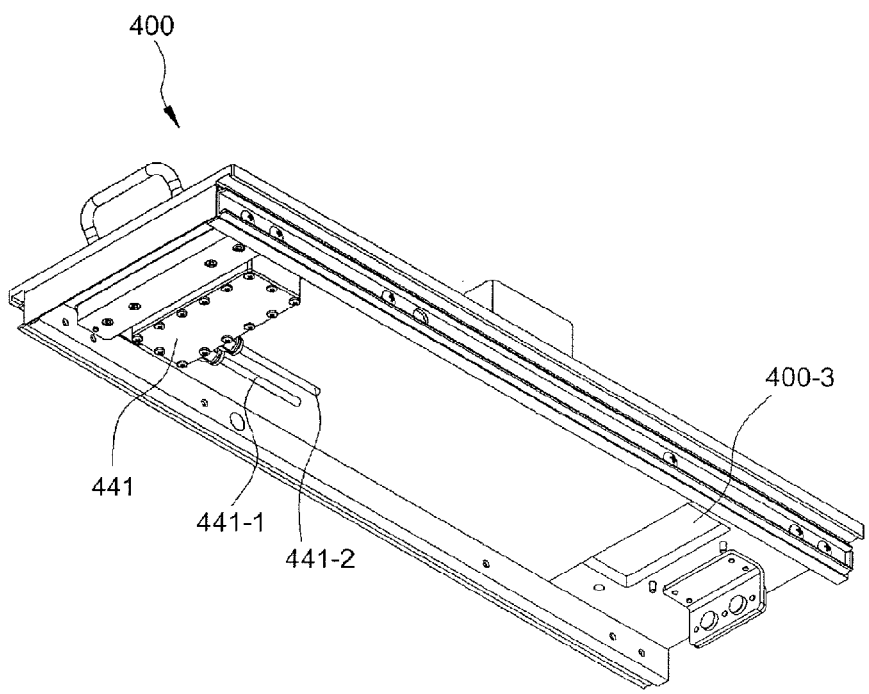
FIG. 14 is a bottom perspective view of FIG. 13.
Figure 15:
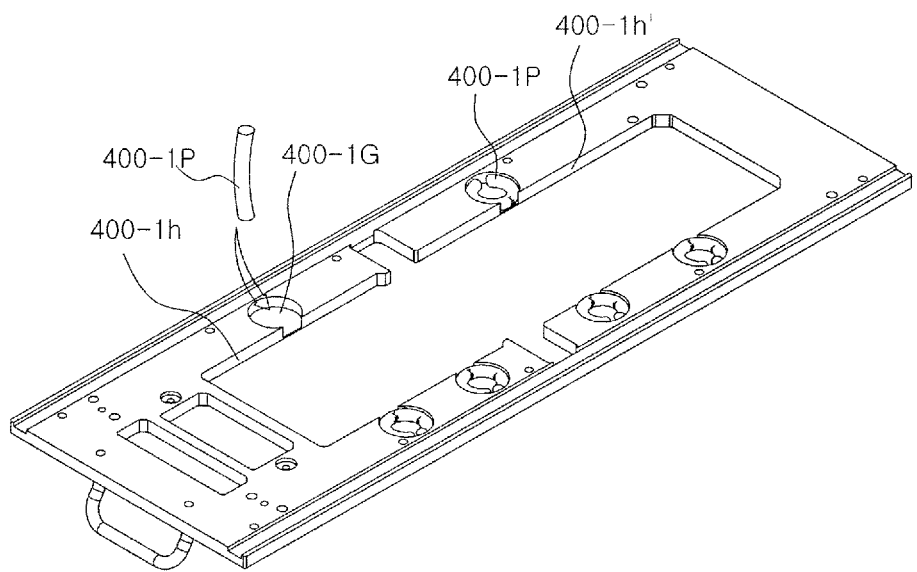
FIG. 15 is a bottom perspective view of a plate body according to the first embodiment of the present invention.
Figure 16:
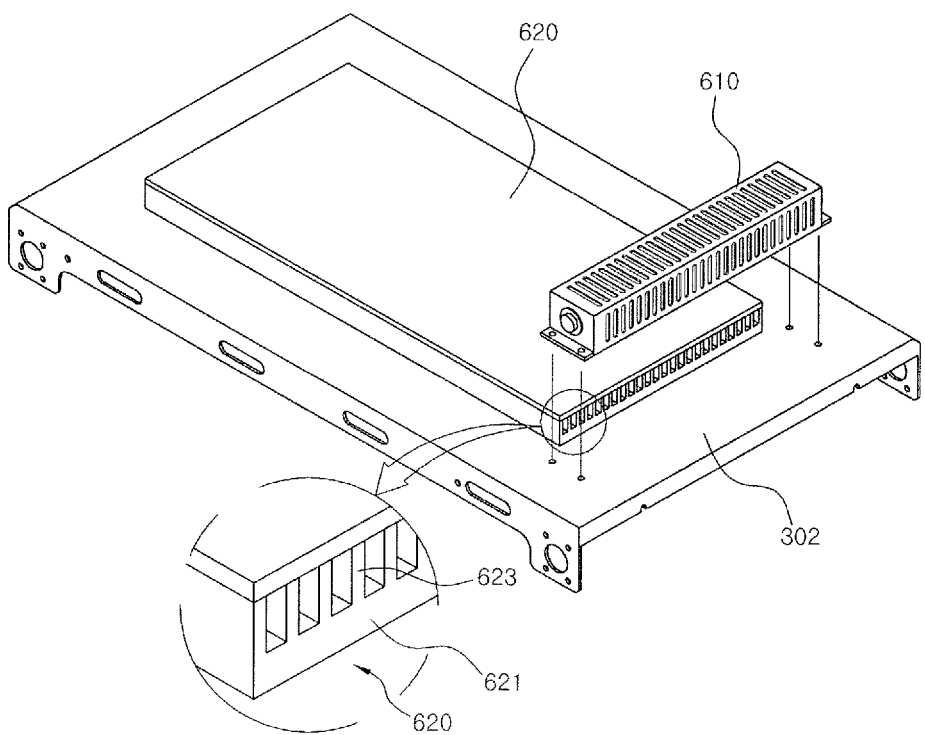
FIG. 16 is a bottom perspective view of a lower plate of the casing according to the first embodiment of the present invention.
Figure 17:
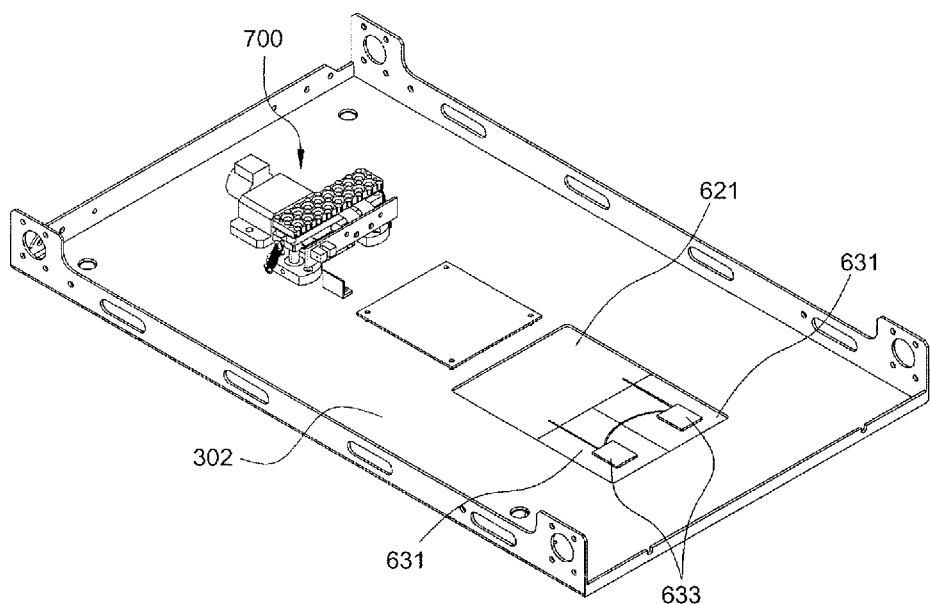
FIG. 17 is a view showing a mounting state of a peltier device according to another embodiment of the present invention.
Figure 18:
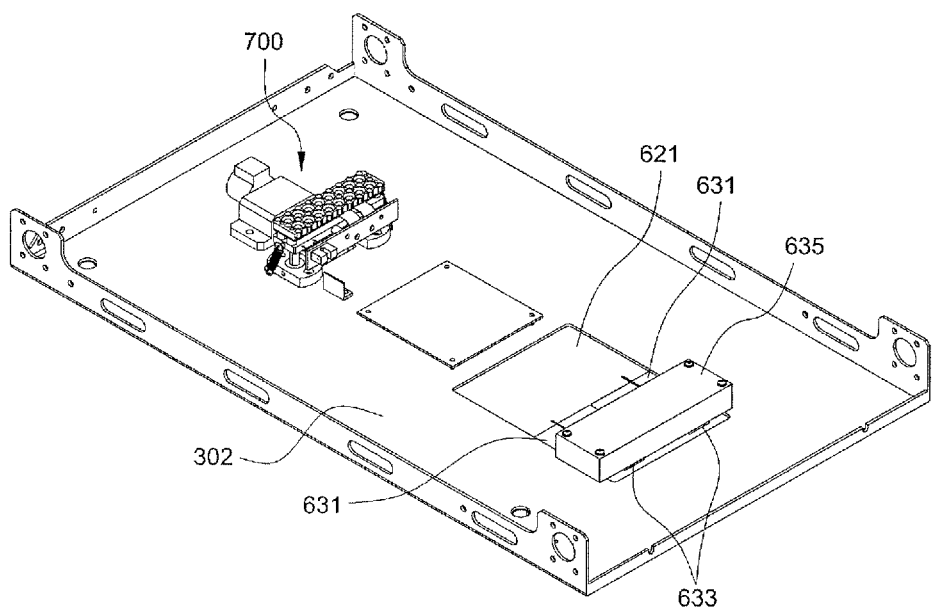
FIG. 18 is a view showing a mounting state of the cooling block according to yet another embodiment of the present invention.
Figure 19:
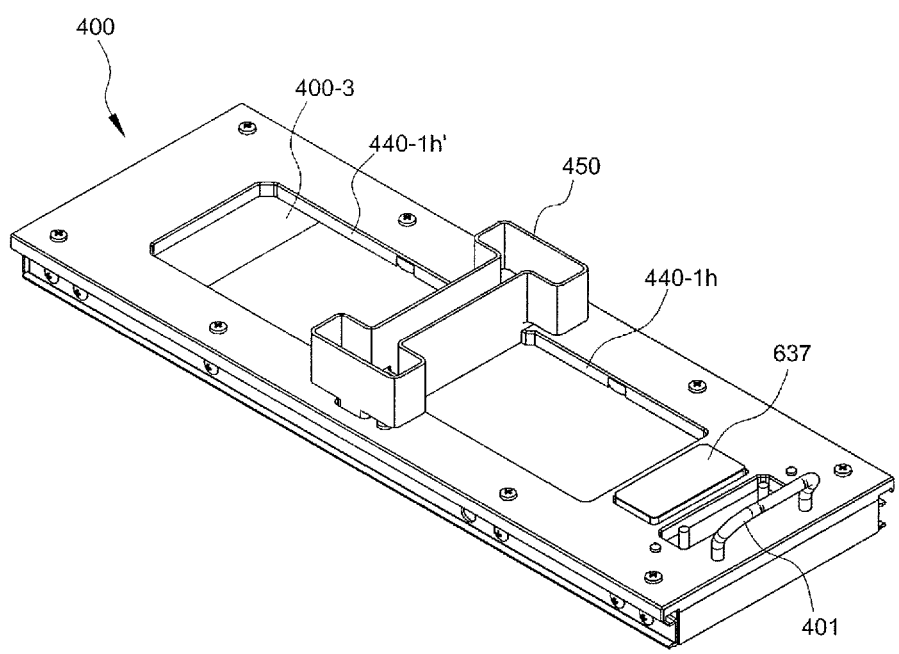
FIG. 19 is a view showing a mounting state of a heat transferring block according to yet another embodiment of the present invention.
Figure 20:
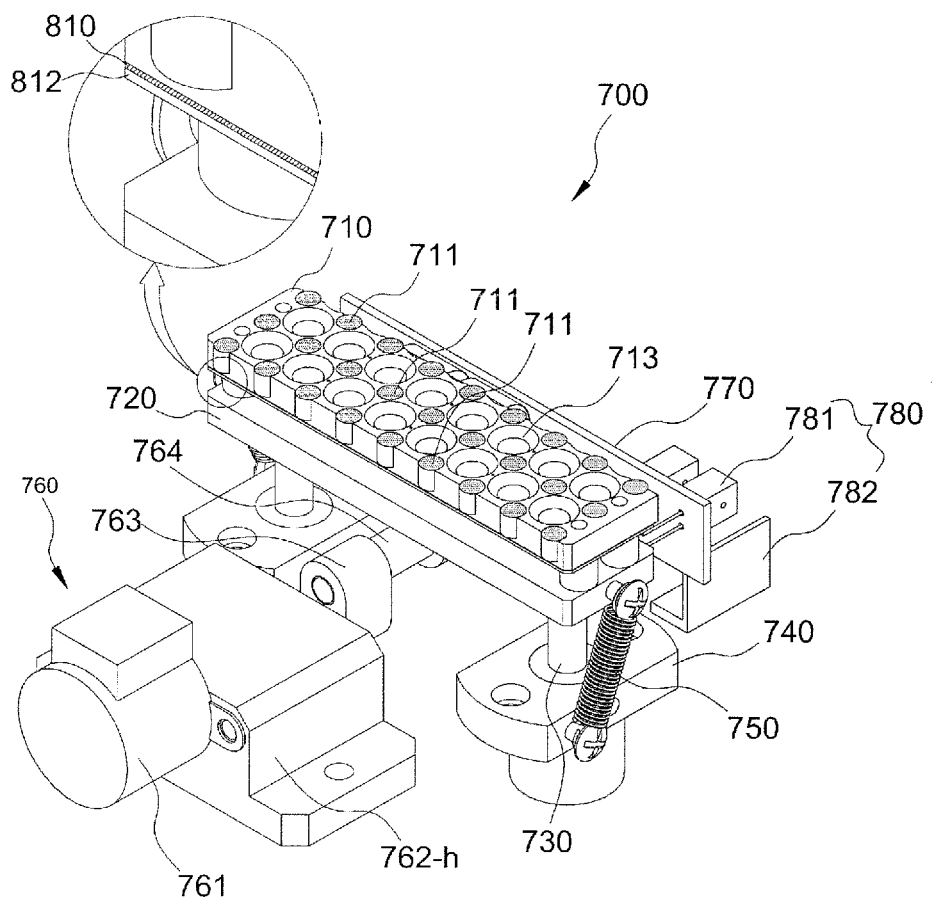
FIGS. 20 and 21 are perspective views of the magnet mounting part and a lifting part according to the first embodiment of the present invention.
Figure 21:
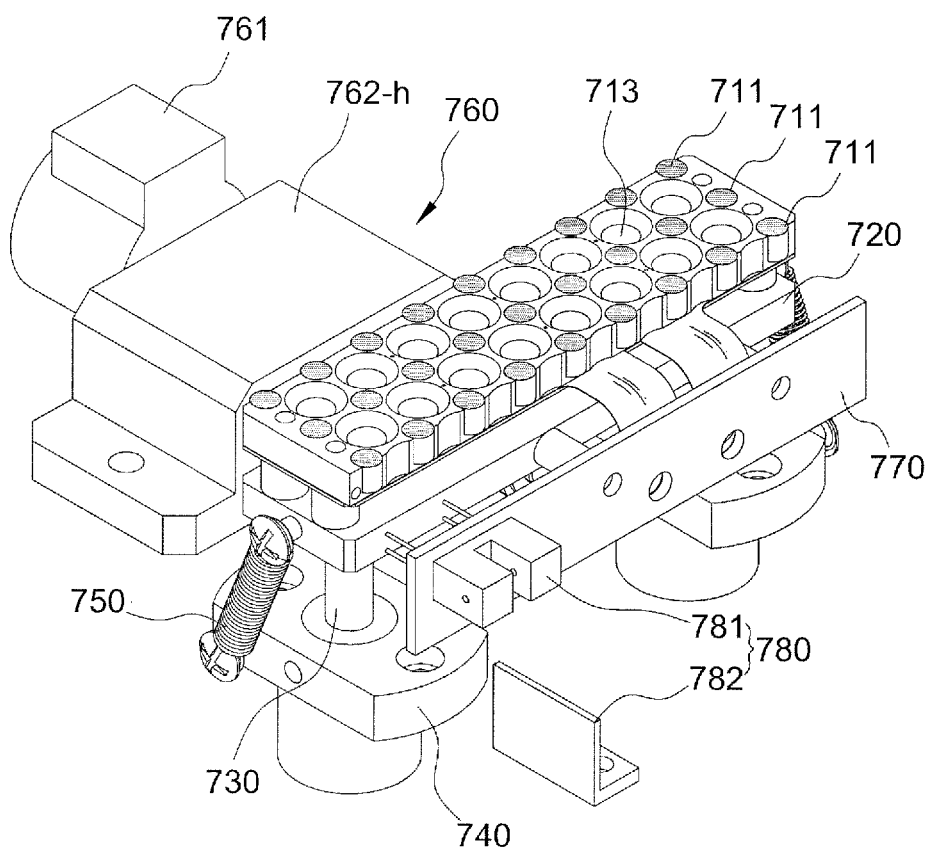
Figure 22:
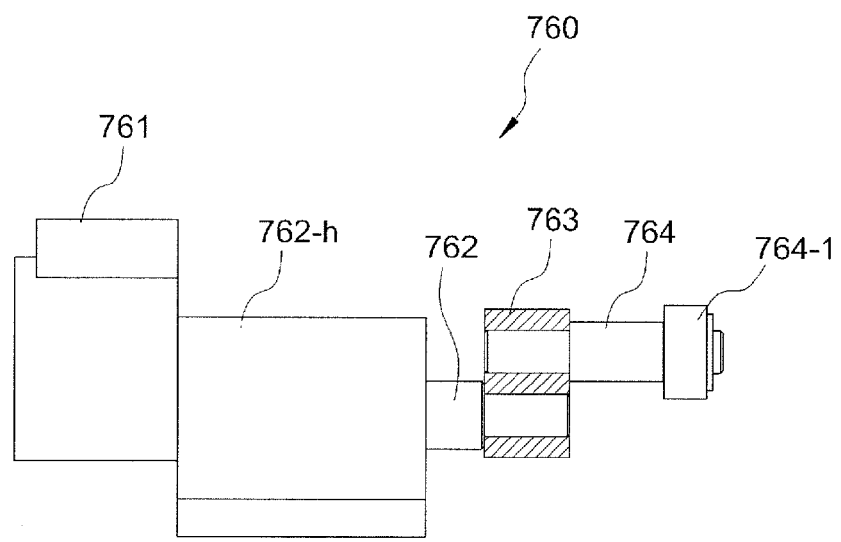
FIG. 22 is a side view of the lifting part according to the first embodiment of the present invention.
Figure 23:
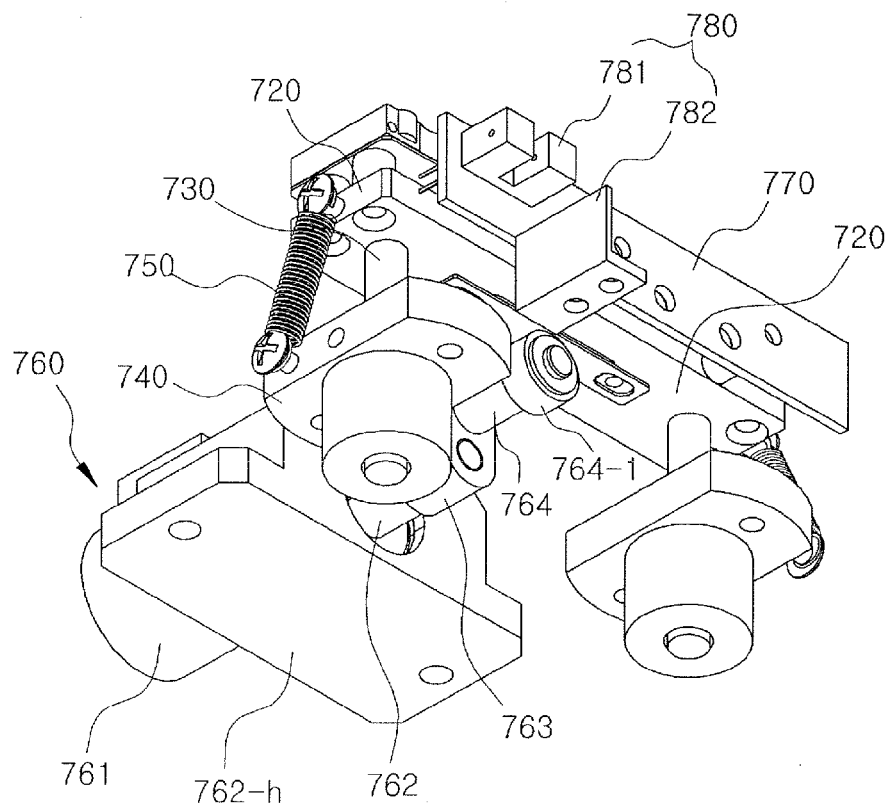
FIG. 23 is a bottom perspective view of the magnet mounting part and the lifting part according to the first embodiment of the present invention.
Figure 24:
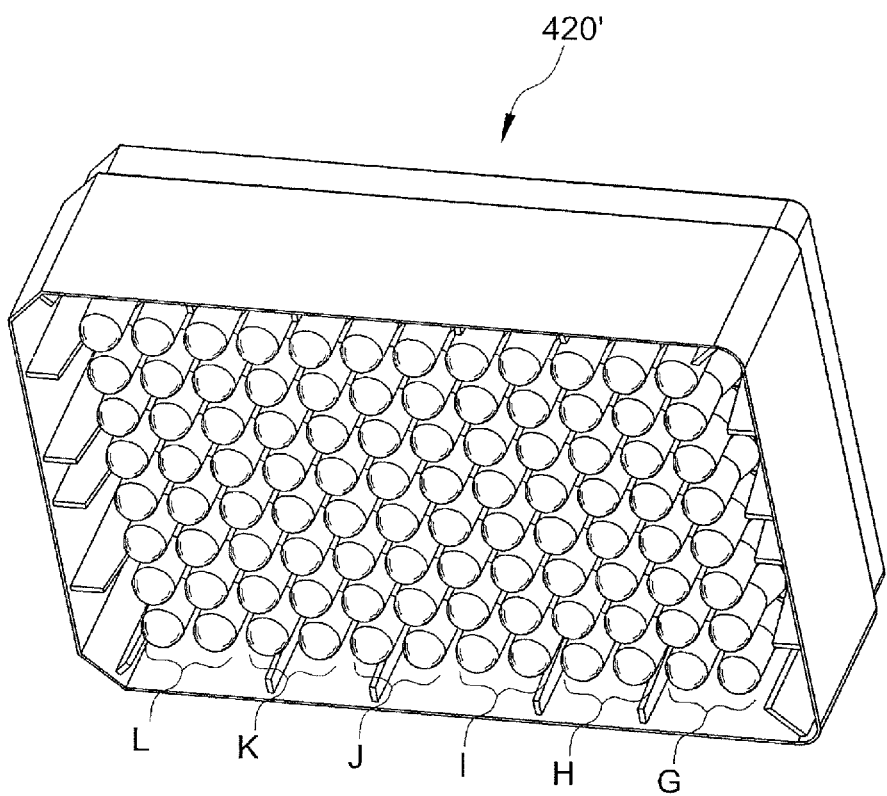
FIG. 24 is a bottom perspective view of the multi-well plate according to the first embodiment of the present invention.

FIG. 1 is a schematic view of a pipette block according to a first embodiment of the present invention, FIG. 2 is a side view of a main part of the pipette block according to the first embodiment of the present invention, FIG. 3 is a schematic view of the first embodiment of which a casing is partially cut away, FIG. 4 is a perspective view of a base plate according to the first embodiment of the present invention, FIG. 5 is a view showing a using state of the base plate according to the first embodiment of the present invention, FIG. 6 is a view showing a state that the base plate is inserted into a casing according to the first embodiment of the present invention, FIG. 7 is a perspective view of a multi-well plate according to the first embodiment of the present invention, FIGS. 8 to 11 are views showing operation states of a solution drip tray and a solution drip tray moving means according to the first embodiment of the present invention, FIG. 12 is a view showing a state that a first tube rack is installed at the base plate according to the first embodiment of the present invention, FIG. 13 is a view showing a state that a cooling block is installed at the base plate according to the first embodiment of the present invention, FIG. 14 is a bottom perspective view of FIG. 13, FIG. 15 is a bottom perspective view of a plate body according to the first embodiment of the present invention, FIG. 16 is a bottom perspective view of a lower plate of the casing according to the first embodiment of the present invention, FIG. 17 is a view showing a mounting state of a peltier device according to another embodiment of the present invention, FIG. 18 is a view showing a mounting state of the cooling block according to yet another embodiment of the present invention, FIG. 19 is a view showing a mounting state of a heat transferring block according to yet another embodiment of the present invention, FIGS. 20 and 21 are perspective views of the magnet mounting part and a lifting part according to the first embodiment of the present invention, FIG. 22 is a side view of the lifting part according to the first embodiment of the present invention, FIG. 23 is a bottom perspective view of the magnet mounting part and the lifting part according to the first embodiment of the present invention, and FIG. 24 is a bottom perspective view of the multi-well plate according to the first embodiment of the present invention.

The automatic purification apparatus of the first embodiment includes a pipette block 100, a fixed body 200, an up and down moving means (not designated by a reference numeral) for pipette block, a front and rear moving means (not designated by a reference numeral) for pipette block, a casing 300, a base plate 400, a solution drip tray 510, a solution drip tray moving means (not designated by a reference numeral), a magnetic field applying part 700 and a heating part 810.

Referring to FIG. 1, the pipette block 100 is provided with a syringe pin holder 110. Referring to FIGS. 2 and 3, a plurality of syringe pins 120 are attached in two rows on a lower surface of the syringe holder 110. In case of other embodiments, the plurality of syringe pins 120 may be attached in one row or three or more rows. The plurality of syringe pins 120 are consists of a first row syringe pins 121 (referring to FIG. 2) and a second row syringe pins 122 (referring to FIG. 3) having the same number of syringe pins as the first row syringe pins 121. For example, the first row syringe pins 121 (referring to FIG. 2) and the second row syringe pins 122 (referring to FIG. 3) may have 8 or 12 syringe pins, respectively.

Referring to FIGS. 1 to 3, the pipette block 100 is provided with a syringe pin guiding block 130. The syringe pin guiding block 130 is formed with a syringe pin guiding hole 131, 132 for guiding up and down movements of the plurality of syringe pins 120. The syringe pin guiding hole 131, 132 may be formed from an upper end of the syringe pin guiding block 130 around a lower end thereof.

Referring to FIG. 2, a pipette mounting part 133, 134 is formed at the lower end of the syringe pin guiding block 130 to be protruded in two rows. The pipette mounting part 133, 134 is formed with a communicating hole 133-1, 134-1 communicated with the syringe pin guiding hole 131, 132. The communicating hole 133-1, 134-1 is formed from a lower end of the pipette mounting part 133, 134 toward an upper end thereof. Meanwhile, as the syringe pin guiding block 130 is moved down, the pipette mounting part 133, 134 is closely contacted with and fitted into upper ends of a plurality of pipettes 141 and 142 which are disposed in two rows at the lower side of the pipette mounting part 133, 134. A tightly-contacting ring 133-2, 134-2 may be inserted onto an outer circumferential surface of the pipette mounting part 133, 134. Thus, the pipette mounting part 133, 134 can be closely contacted with and fitted into the upper ends of the pipettes 141 and 142. The pipette mounting parts 133 and 134 are formed into the same shape so as to be fitted into the pipettes 141 and 142 to the same depth when the plurality of pipettes 141, 142 are fitted with the pipette mounting part 133, 134.

Referring to FIGS. 1 and 2, the lower end of the syringe pin guiding block 130 is fixedly supported to a supporting plate 150 for syringe pin guiding block. Referring to FIG. 2, the supporting plate 150 for syringe pin guiding block is formed with a through-hole (not designated by a reference numeral) so that the pipette mounting part 133, 134 can be passed down through the supporting plate 150 for syringe pin guiding block.

Referring to FIG. 1, an up and down moving nut 152 is fixedly attached on the supporting plate 150 for syringe pin guiding block. Meanwhile, an up and down moving screw 233 is screwed into the up and down moving nut 152 so as to be relatively rotatable.

Referring to FIG. 3, an upper end of the up and down moving screw 233 is connected to the fixed body 200 so as to be relatively rotatable with respective to the fixed body 200 but not movable up and down. Referring to FIG. 3, an up and down moving motor 231 is installed at the fixed body 200, and an up and down moving belt 232 is connected to the up and down moving motor 231. As the up and down moving belt 232 is moved, the up and down moving screw 233 is rotated, and the supporting plate 150 for syringe pin guiding block is moved up and down with respect to the fixed body 200. The up and down moving belt 232 may be a timing belt.

Referring to FIG. 1, the pipette block 100 is provided with a guiding rod 160. The guiding rod 160 is formed to be protruded on an upper surface of the supporting plate 150 for syringe pin guiding block. The guiding rod 160 is fitted into the syringe holder 110 so as to guide up and down movement of the syringe holder 110. A guide member 112 for guiding the up and down movement of the syringe holder 110 may be fixedly connected to the syringe holder 110.

Referring to FIG. 1, a supporting plate 171 for syringe pin adjusting motor is disposed on an upper end of guiding rod 160. A syringe pin adjusting motor 172 is mounted on the supporting plate 171 for syringe pin adjusting motor, and a syringe pin adjusting screw 173 is installed at the syringe pin adjusting motor 172 so as to be rotatable and movable up and down. A lower end of the syringe pin adjusting screw 173 is disposed at the syringe pin holder 110 so as to be relatively rotatable but not movable up and down.

Referring to FIG. 1, an upper detachable plate 181 is installed at the upper side of syringe pin guiding block 130. The upper detachable plate 181 is formed with through-holes (not shown) through which a plurality of syringe pins 120 can be passed.

Referring to FIG. 2, a lower detachable plate 182 is installed at the lower side of the supporting plate 150 for syringe pin guiding block 150. The lower detachable plate 182 is formed with through-holes (not designated by a reference numeral) through which the plurality of pipette mounting parts 133 and 134 can be passed. The through-holes (not designated by a reference numeral) through which the pipette mounting parts 133 and 134 are passed have a desired size that the plurality of pipette mounting parts 133 and 134 can be passed through but the plurality of pipettes 141 and 142 installed at the pipette mounting parts 133 and 134 cannot be passed through. Therefore, as the lower detachable plate 182 is moved down, the upper portions of the plurality of pipettes 141 and 142 installed at the pipette mounting parts 133 and 134 are pressed downward, and the plurality of pipettes 141 and 142 can be separated. The upper and lower detachable plates 181 and 182 are connected with each other through a connecting rod 183 so as to be spaced apart from each other in a desired distance. Meanwhile, the syringe pin guiding block 130 is formed with a through-hole (not designated by a reference numeral) through which the connecting rod 183 can be installed.

Referring to FIG. 1, a protruding rod 184 is protruded on an upper surface of the lower detachable plate 182. The protruding rod 184 is protruded to the upper side of the supporting plate 150 for syringe pin guiding block through a through-hole (not designated by a reference numeral) formed at the supporting plate 150 for syringe pin guiding block. A spring 185 is inserted onto the protruding rod 184. A lower end of the spring 185 is elastically supported on the upper surface of the supporting plate 150 for syringe pin guiding block and an upper end thereof is elastically supported to an upper end of the protruding rod 184, and thus desired elastic force is exerted so that the lower detachable plate 182 is closely contacted with the supporting plate 150 for syringe pin guiding block. Referring to FIGS. 1 and 2, in case that the syringe pin holder 110 is moved down so as to press the upper detachable plate 181 and the pressing force is larger than the elastic force of the spring 185, the lower detachable plate 182 is moved down and thus the plurality of pipettes 141 and 142 are separated.

In other words, as the pipette mounting part 133, 134 is moved down, the plurality of pipettes 141 and 142 are installed at the pipette mounting part 133, 134. And as the lower detachable plate 182 is moved down, the plurality of pipettes 141 and 142 are separated from the pipette mounting part 133, 134. Further, as the syringe pin 120 is moved up and down, a biological sample including a target substance is injected into or discharged from each of the pipettes 141 and 142.

Referring to FIG. 2, the plurality of pipettes 141 and 142 installed at the pipette mounting part 133, 134 are formed to perform four main functions. Since the pipette 141 and the pipette 142 are the same as each other, the pipette 142 will be explained representatively. An awl-shaped portion 142a is sharply formed at a lower end of the pipette 142 in order to easily punch a hole in a film (not shown) of a multi-well plate 420, 420'. A solution passage 142b is formed to be elongated and thus contacted with the bottom of a well 421A, 421B, 421C, 421D, 421E, 421F of the multi-well plate 420. Further, in order to minimize an amount of solution remained therein, the solution passage 142b is formed as thin as possible. Meanwhile, a solution storing part 142d has an adjusted inner diameter and length so as to have a maximum capacity within a range of 9 mm which is a space between wells of faced rows in an adjacent 96-well plate.

Referring to FIG. 3, a front and rear moving support rod 310 is installed at front and rear sides of the casing 300.

Referring to FIG. 3, a front and rear moving slider 241 is inserted onto the front and rear moving support rod 310. The front and rear moving slider 241 is fixed to the fixed body 200. A front and rear moving motor 320 is installed at the casing 300, and the front and rear moving motor 320 is connected with a front and rear moving belt 330. Therefore, as the front and rear moving motor 320 operates, the front and rear moving belt 330 is moved. A desired portion of the front and rear moving belt 330 is attached to the fixed body 200. Therefore, as the front and rear moving belt 330 is moved, the fixed body 200 is moved forward and backward along the front and rear moving support rod 310.

Referring to FIG. 3, a front and rear guider 311 is disposed at the opposite side of the front and rear moving support rod 310 so as to support the other side of the fixed body 200 and guide front and rear movement of the fixed body 200.

Referring to FIG. 3, a base plate 400 is located at the lower side of the fixed body 200. Referring to FIG. 4, a sliding rail 410 is installed at a lower surface of the base plate 400 so that the base plate 400 can be slid with respect to the casing 300.

Referring to FIGS. 4 and 5, on the base plate 400, there are installed the multi-well plate 420, 420', a pipette rack 430 in which the plurality of pipettes 140 to be installed at the pipette block 100 are received in two rows, a first tube rack 440 which receives a target substance tube 442-1, 442-3 for receiving an isolated target substance, and a waste liquid container 450 which receives waste liquid discharged from the plurality of pipettes 140 installed at the pipette block 100. The target substance tube 442-1, 442-3 includes a plurality of target substance receiving tubes 442-1 for receiving the isolated target substance and a plurality of target substance diagnosing tubes 442-3 for diagnosing the isolated target substance. Meanwhile, the first tube rack 440 may be provided with a separate tube (not shown) for receiving other solution. In this case, one of the target substance receiving tube 442-1 and the target substance diagnosing tube 442-3 of the target substance tube 442-1, 442-3 may be not installed.

Referring to FIG. 3, a sterilization unit such as an ultraviolet lamp 340 and an ozone unit (not shown) may be disposed in the casing 300.

FIG. 7 shows the multi-well plate 420 which is received in the casing 300 while being mounted on the base plate 400 and also located at the lower side of the pipette block 100.

Referring to 7, the multi-well plate 420 includes a plurality of unit wells A, B, C, D, E and F consisting of multiple wells 421A, 421B, 421C, 421D, 421E and 421F arranged in adjacent two rows, and a film (not shown) for sealing an upper surface of each unit well A, B, C, D, E, F. In other words, the multi-well plate 420 may be a 96-well plate. Meanwhile, unlike in FIG. 7, the multi-well plate 420 may have unit wells arranged in one row.

Referring to FIG. 5, a protease for cell lysis and protein degradation, a ribonuclease for RNA degradation, or a buffer solution for sample pretreatment may be injected and sealed in the unit well A. A cell lysis solution for dissolving a biological sample may be injected and sealed in the unit well C, and a binding solution may be injected and sealed in the unit well D, an aqueous dispersion solution in which magnetic particles are dispersed may be injected and sealed in the unit well E, and a first cleaning solution may be injected and sealed in the unit well F, and a second cleaning solution may be injected and sealed in the unit well G, and a third cleaning solution may be injected and sealed in the unit well H, and a fourth cleaning solution may be injected and sealed in the unit well I, and a target substance elution solution may be injected and sealed in the unit well K. That is, a solution for purifying the sample is received in each unit well, and the same solution may be received in the same unit well.

Meanwhile, in case that the solution received in one sealed unit well is the aqueous dispersion solution in which magnetic particles are dispersed, the magnetic particles dispersed in the aqueous dispersion solution may be spherical magnetic particles coated with silica.

Referring to FIGS. 8 to 11, a solution drip tray 510 is disposed to be moved forward and backward on the fixed body 200 by the solution drip tray moving means (not designated by a reference numeral). When the pipette block 100 is moved forward and backward, the solution drip tray 510 is located at the lower side of the pipettes 141 and 142 by the solution drip tray moving means (not designated by a reference numeral). Therefore, when the pipette block 100 is moved forward and backward, the solution drip tray 510 is also moved forward and backward together with the pipette block 100 so as to catch solution drips undesirably fallen from the plurality of pipettes 141 and 142. Thus, it is prevented that the solution drips are undesirably fallen from the plurality of pipettes 141 and 142 and then introduced into the plurality of unit wells A, B, C, D, E, F, G, H, I, J, K, L of the multi-well plate 420, 420'.

Referring to FIGS. 8 to 11, the solution drip tray moving means (not designated by a reference numeral) is installed at the fixed body 200. The solution drip tray moving means (not designated by a reference numeral) may include a pinion 521, a rack 531, a rack supporter 533 and a rack supporter guiding means (not designated by a reference numeral).

Figure 8:
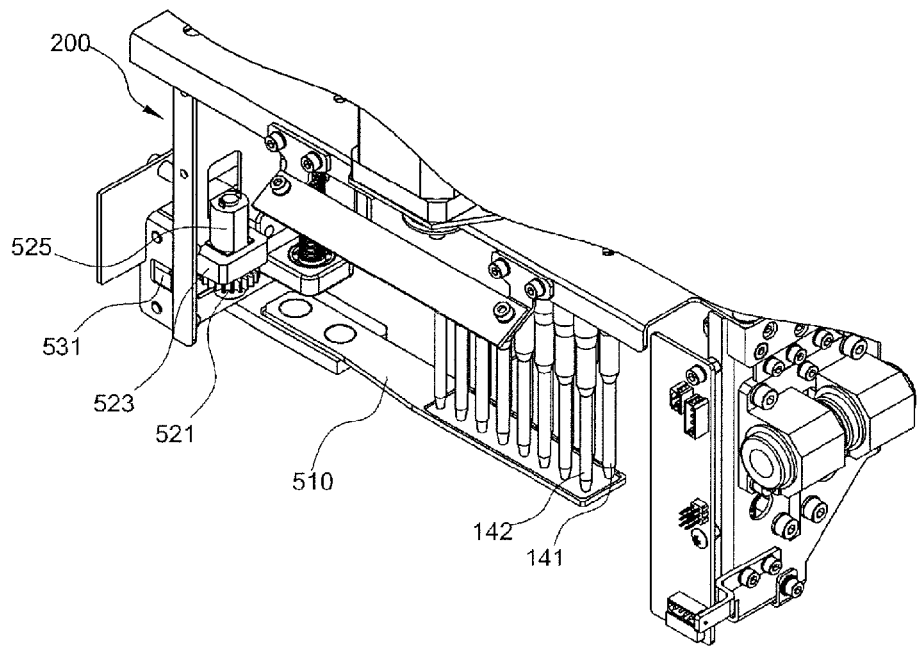
FIGS. 8 to 11 are views showing operation states of a solution drip tray and a solution drip tray moving means according to the first embodiment of the present invention.
Figure 9:
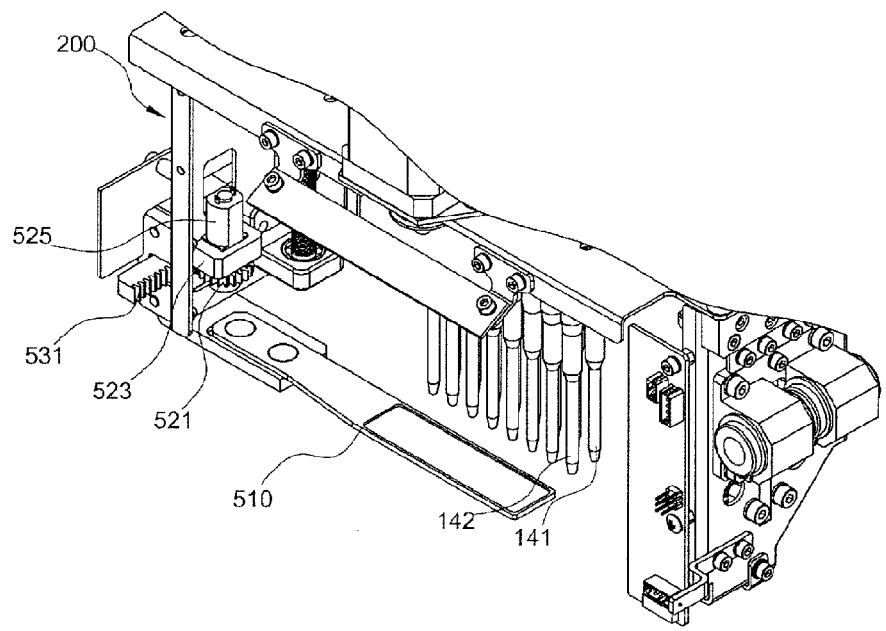

Referring to FIGS. 8 and 9, the pinion 521 is rotatably disposed at the fixed body 200. That is, a pinion block 523 is formed so as to be protruded from the fixed body 200, and the pinion 521 can be rotatably installed at the pinion block 523. Meanwhile, a pinion rotating motor 525 may be disposed on an upper surface of the pinion block 523 so as to rotate the pinion 521.

Referring to FIG. 9, the rack 531 is engaged with the pinion 521 and disposed so as to be movable forward and backward with respect to the fixed body 200.

Referring to FIGS. 10 and 11, one side of the rack supporter 533 is attached to the rack 531.

Referring to FIGS. 10 and 11, the solution drip tray 510 is attached to the other side of the rack supporter 533.

Referring to FIGS. 10 and 11, the rack supporter guiding means (not designated by a reference numeral) functions to guide the rack supporter 533 in the front and rear direction thereof, and includes a rack supporter guiding rod 535 and a fixing protrusion 537 for rack supporter guiding rod.

Referring to FIGS. 10 and 11, the fixing protrusion 537 for rack supporter guiding rod is formed to be protruded from an outer surface of the fixed body 200.

Referring to FIGS. 10 and 11, both side ends of the rack supporter guiding rod 535 are fixed to the fixing protrusion 537 for rack supporter guiding rod. The rack supporter 533 is formed with a rack supporter guiding hole 533-1 formed in the front and rear direction thereof. The rack supporter guiding rod 535 is inserted into the rack supporter guiding hole 533-1. Therefore, when the rack 531 is moved forward and backward, the rack supporter 533 is guided by the rack supporter guiding rod 535 so as to be slid forward and backward with respect to the fixed body 200.

Referring to FIG. 12, inserting holes 440-1 for target substance receiving tube and inserting holes 440-3 for target substance diagnosing tube are formed at the first tube rack 440 of the base plate 400 in two rows, respectively. The inserting holes 440-1 for target substance receiving tube are to receive the plurality of target substance receiving tubes 442-1 for receiving a purified target substance, and the inserting holes 440-3 for target substance diagnosing tube are to receive the target substance diagnosing tubes 442-3 in which a diagnostic kit or a diagnostic reagent to be mixed with the purified target substance is injected.

Referring to FIG. 13, a cooling block 441 for cooling the first tube rack 440 is mounted on the base plate 400.

Referring to FIG. 14, a cooling water line (not shown), of which one side end is connected with a cooling water inlet line 441-1 and the other side end is connected with a cooling water outlet line 441-2, is installed in the cooling block 441. While the cooling water introduced through the cooling water inlet line 441-1 is passed through the cooling water line (not shown) and then discharged through the cooling water outlet line 441-2, the cooling block 441 is cooled, and thus the first tube rack 440 contacted with an upper surface of the cooling block 441 is also cooled.

Referring to FIG. 13, the base plate 400 includes a plate body 400-1 and a plate supporting part 400-2. The plate body 400-1 is coupled to an upper surface of the plate supporting part 400-2. The plate body 400-1 is formed with a multi-well plate mounting hole 400-1*h*, 400-1*h*' which allows the multi-well plate 420, 420' to be settled on the plate supporting part 400-2. Meanwhile, the base plate 400 is formed with a unit well exposing hole 400-3 through which a lower portion of a particular unit well L of the multi-well plate 420, 420' can be exposed downward.

Referring to FIG. 15, a lower surface of the plate body 400-1 is formed with an elastic body inserting groove 400-1G communicated with the multi-well plate mounting hole 400-1*h*, 400-1*h*'.

Referring to FIG. 15, a separation preventing elastic body 400-1P is fitted into the elastic body inserting groove 400-1G. The separation preventing elastic body 400-1P is a rod-shaped elastic body formed of a soft material. When being deformed into a ring shape, the separation preventing elastic body 400-1P is fitted into the elastic body inserting groove 400-1G, a desired portion thereof is protruded to the multi-well plate mounting hole 400-1*h*, 400-1*h*'. Therefore, the separation preventing elastic body 400-1P is elastically contacted with the side surface of the multi-well plate 420, 420' settled on the plate supporting part 400-2, and thus it is prevented that the multi-well plate 420, 420' is separated upward.

Referring to FIG. 16, in other embodiment of the present invention, an air blower 610 and an air guiding part 620 may be attached to a lower surface of the lower plate 302 of the casing 300.

Referring to FIG. 16, an upper surface of the air guiding part 620 attached to the lower plate 302 of the casing 300 is formed of a heat sinking plane 621. Both side ends of the air guiding part 620 are opened so that air generated by the air blower 610 is introduced through one side end thereof and then discharged through the other side end thereof. Meanwhile, a plurality of straight guide plates 623 for guiding the air introduced by the air blower 610 are disposed in the air guiding part 620 so as to be spaced apart from each other.

Referring to FIG. 17, a desired portion of an upper surface of the heat sinking plane 621 is exposed to the inside of the casing 300 through a through portion (not designated by a reference numeral) formed in the lower plate 302 of the casing 300. Meanwhile, a heat pipe 631 is installed at the desired portion of the upper surface of the heat sinking plane 621, which is exposed to the inside of the casing 300.

Referring to FIG. 17, a peltier device 633 is mounted on the heat pipe 631. Referring to FIG. 18, a cooling block 635 is mounted on the peltier device 633. Thus, the cooling block 635 mounted on the peltier device 633 is cooled. Meanwhile, a lower surface of the peltier device is cooled by the heat pipe 631 and the heat sinking plane 621.

Referring to FIG. 19, a heat transferring block 637 is mounted on the base plate 400. A lower surface of the heat transferring block 637 is contacted with an upper surface of the cooling block 635 according to a moved state of the base plate 400, and thus the heat transferring block 637 is cooled. The upper surface of the cooling block 635 is contacted with the first tube rack 440, thereby cooling the first tube rack 440.

Referring to FIG. 17, a magnetic field applying part 700 is mounted on the lower plate of the casing 300. Referring to FIG. 5, the magnetic field applying part 700 is to apply and release the magnetic field to the particular unit well L of the multi-well plate 420, 420'.

Referring to FIGS. 20 and 21, the magnetic field applying part 700 includes a magnet mounting part 710 on which a magnet is mounted and a lifting part 760 which lifts up and down the magnet mounting part 710.

Referring to FIGS. 20 and 21, a plurality of unit well inserting grooves 713 are formed at an upper surface of the magnet mounting part 710 so as to be spaced apart from each other in two rows. The unit well inserting groove 713 allows the lower portion of the particular unit well L of the multi-well plate 420, 420' to be introduced therein when the magnet mounting part 710 is lifted up. In other words, as the upper surface of the magnet mounting part 710 is lifted up through the unit well exposing hole 400-3, the lower portion of the particular unit well L is introduced into the unit well inserting groove 713.

Referring to FIG. 24, the lower portion of the particular unit well L of the multi-well plate 420, 420' is spaced apart from a lower portion of other unit well adjacent to the particular unit well L in a desired distance so as to be inserted into the unit well inserting groove 713. Further, the plurality of wells of the particular unit well L are spaced apart from each other in regular intervals.

FIGS. 20 and 21, magnets 711 are fixedly disposed around the unit well inserting grooves 713. The magnets 711 are disposed to apply the same magnetic field to each well forming the particular unit well L. The magnets 711 may be cylindrical permanent magnets, preferably, powerful magnets formed of neodymium, samarium/cobalt, alnico or the like.

Referring to FIG. 20, the first embodiment is provided with a heating part 810 for heating the particular unit well L. The heating part 810 may be a heat generating film which is contacted with a lower surface of the magnet mounting part 710 by a heating part fixing plate 812. In this case, the magnet mounting part 710 is formed of a metal material having a high heat transfer rate.

Referring to FIGS. 20 and 21, a magnet mounting part supporter 720 for supporting the magnet mounting part 710 is disposed at the lower side of the magnet mounting part 710.

Referring to FIGS. 22 and 23, the lifting part 760 includes a lifting motor 761, a first lifting shaft 762, a lifting cam 763 and a second lifting shaft 764.

Referring to FIGS. 22 and 23, the first lifting shaft 762 is rotatably installed at a first lifting shaft housing 262-h, and one end of the first lifting shaft 762 is connected to the lifting motor 761 so that the first lifting shaft 762 may be rotated by driving force of the lifting motor 761. The lifting cam 763 is integrally connected with the other end of the first lifting shaft 762. One end of the second lifting shaft 764 is connected to the lifting cam 763 so as to be moved circularly, such that the second lifting shaft 764 may be movable up and down upon rotation of the lifting cam 763. That is, the second lifting shaft 764 is disposed to be spaced apart from a rotational shaft of the lifting cam 763. The other end of the second lifting shaft 764 is disposed to be contacted with a lower surface of the magnet mounting part supporter 720. A rotational cylinder 764-1 which can be rotated with respect to the second lifting shaft 764 may be fitted on the other end of the second lifting shaft 764.

Referring to FIGS. 20 and 21, a guide rod 730 is disposed at the lower surface of the magnet mounting part supporter 720. A guide block 740 is disposed at the lower side of the magnet mounting part supporter 720, and the guide block 740 is formed with a guide hole in which the guiding rod 730 is inserted so as to be slid up and down.

Referring to FIGS. 20 and 21, an upper end of a tension spring 750 is connected to the magnet mounting part supporter 720, and a lower end thereof is connected to the guide block 740. If the second lifting shaft 764 is moved down while performing the circular movement, the magnet mounting part supporter 720 is contacted and supported to the rotational cylinder 764-1 by elastic force of the tension spring 750, and thus the magnet mounting part supporter 720 can be rapidly lifted down.

Referring to FIGS. 20 and 21, the first embodiment is provided with a height detecting sensor 780. The height detecting sensor 780 includes a sensing part 781 and a sensing target part 782. A sensing part mounting plate 770 on which the sensing part 781 is mounted may be installed at the magnet mounting part supporter 720.

Hereinafter, the operation of the first embodiment will be described.

Referring to FIGS. 4 and 5, the 96-well plate as the multi-well plate 420, 420' is installed at the base plate 400 when being used. Since the sliding rail 410 is installed at the lower surface of the base plate 400, the base plate 400 can be dragged out of the casing 300 using a handle 401, as shown in FIG. 6, and then other necessary parts can be installed thereon. In order to operate the first embodiment, the multi-well plate 420, 420', waste liquid container 450 and the like are installed at the base plate 400. More detailedly, in order to operate the first embodiment, first of all, the number of biological samples containing the target substance has to be determined. In the first embodiment, it is possible to purify 1 to 16 biological samples. FIG. 5 shows a process of preparing 16 samples, as a special example of the first embodiment. The magnetic particles and various solutions are injected in the multi-well plate 420, 420'. Further, since the multi-well plate 420, 420' functions as a plate in which the biological samples are injected and installed, holes corresponding to the necessary number of biological samples are punched in the film sealed on the unit well A of the multi-well plate 420 using tips of the pipettes 141 and 142, and each of the biological samples is injected into each well 421A. After that, the multi-well plate 420 is installed at the base plate 400, and then other multi-well plate 420' receiving other solutions is also installed at the base plate 400. In order to collect waste liquid generated in the purification process, the waste liquid container 450 is also installed. When the pipette 141, 142 is put into the pipette rack 430, the position of the biological sample injected into the multi-well plate 420 is checked first, and then the pipette 140 installed at the pipette mounting part 133, 134 is put therein so as to be located at the upper side of the position that the biological sample is injected. The same number of target substance receiving tubes 442-1 are put into the first tube rack 440 and then installed therein. Herein, the target substance receiving tube 442-1 is a standard product used in the 96-well plate, such as an 8-strip tube for PCR (in FIG. 5, all of the 16 target substance receiving tubes 442-1 are installed). In case that only part of the wells, which are less than 16, is used, it is important that the pipettes 140, the target substance receiving tubes 442-1, the target substance diagnosing tubes 442-3 are located at the same positions when they are moved forward and backward. To this end, preferably, the pipette rack 430 and the first tube rack 440 are arranged to be parallel with each other, and then the pipettes 140, the target substance receiving tubes 442-1, the target substance diagnosing tubes 442-3 are put therein so as be located at the same positions when they are moved forward and backward.

After the installation, the base plate 400 is pushed in the casing 300 until it is contacted with a stopper 403, and a door 350 of the casing 300 is closed, and then the automatic purification is performed by operating a touch screen 360. If a high-temperature reaction treatment is needed during the automatic purification, the heating part 810 (referring to FIG. 20) is operated. If the automatic purification for about 30 minutes is finished, the door 350 is opened and the base plate 400 is dragged out again, and the first tube rack 440 in which the purified target substance is received is taken out in order to collect the purified target substance, and the used pipette 140 is picked out, and the target substance receiving tube 442-1 is closed by a cap and then used in a necessary test or stored in a freezer of −20 degrees Celsius. Further, in the first embodiment, there is an advantage in that it is possible to inject the purified target substance into the target substance diagnosing tube 442-3 and then carry out the necessary test. All of the 96-well plate, pipettes and waste liquid container and the like are taken out and then discarded from the base plate 400, and the base plate 400 is pushed again until it is contacted with the stopper 403, and the door 350 of the casing 300 is closed, and then the inside of the apparatus is sterilized by the ultraviolet lamp 340. If all of the 16 wells of the 96-well plate are used, the 96-well plate is removed, and if some unused wells are remained, it will be used again.

The purification process except the preparation and post-treatment can be carried out by automatic equipment and computer circuit of the automatic purification apparatus.

Meanwhile, the up and down movement of the pipette block 100 is performed by the up and down moving screw 233, and the front and rear movement thereof is performed by the front and rear moving belt 330. The operation can be carried out at a desirable place by using the up and down moving screw 233 and the front and rear moving belt 330.

In the first embodiment, there is an advantage in that the target substance diagnosing tube 442-3 can be installed in the first tube rack 440 of the base plate 400, and the purified target substance can be stored in the target substance receiving tube 442-1 or automatically mixed with the diagnostic kit or the diagnostic reagent received in the target substance diagnosing tubes 442-3 using the plurality of pipettes 141 and 142.

In the first embodiment or other embodiment, there is another advantage in that the first tube rack 440 can be cooled by the cooling block 441, 635 and thus the target substance received in the target substance receiving tube 442-1 and the diagnostic kit or the diagnostic reagent received in the target substance diagnosing tubes 442-3 can be maintained at a temperature of 3~5° C.

Since the first embodiment is provided with the solution drip tray 510, it is prevented that the solution drips are undesirably fallen from the plurality of pipettes 141 and 142 and then introduced into the plurality of unit wells of the multi-well plate 420, 420'.

In the first embodiment, the separation preventing elastic body 400-1P is fitted into the elastic body inserting groove 400-1G and elastically contacted with the side surface of the multi-well plate 420, 420' settled on the multi-well plate mounting hole 400-1h, 400-1h'. Thus, it is prevented that the multi-well plate 420, 420' is separated upward from the base plate 400.

According to the first embodiment, in a state that the magnetic particles on which the target substance is attached are injected into the particular unit well L, the magnetic field can be applied to the particular unit well L, and other solutions except the magnetic particles on which the target substance is attached can be removed using the pipette 140, or in a state that the magnetic particles and the target substance elution solution including the target substance isolated from the magnetic particles are injected into the particular unit well L, the magnetic field can be applied to the particular unit well L, and the solutions except the magnetic particles can be separated using the pipette 140. Therefore, it is possible to provided higher removing and separating efficiency.

Second Embodiment

A second embodiment relates to a method of expressing and purifying protein as a target substance from a biological sample using the first embodiment.

Figure 25:
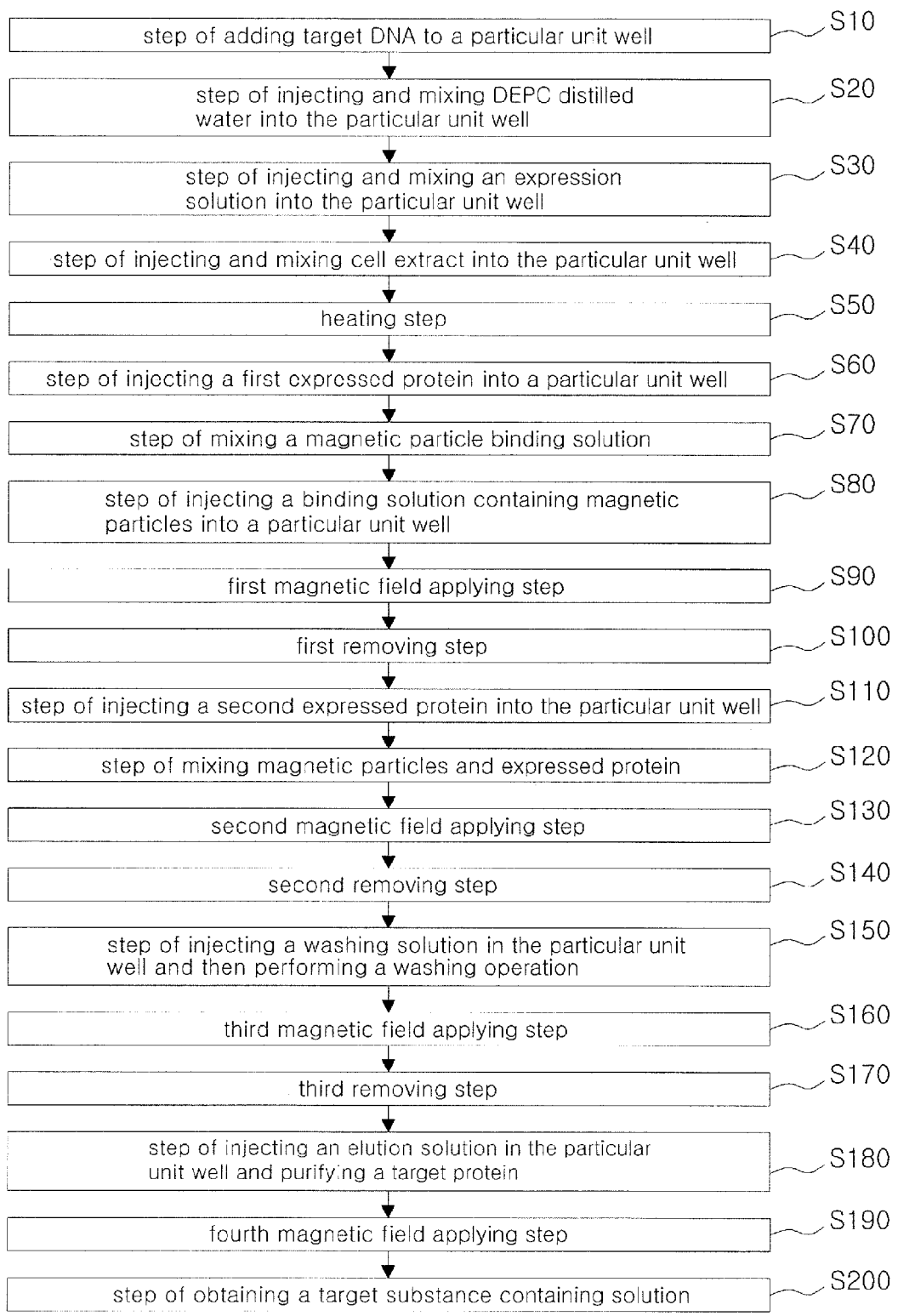
FIG. 25 is a flow chart according to a second embodiment of the present invention.

FIG. 25 is a flow chart according to a second embodiment of the present invention.

In order to carry out the second embodiment, a preparing process has to be performed firstly.

Referring to FIG. 5, in the preparing process, the two multi-well plates 420 and 420', the pipette rack 430 in which the plurality of pipettes 140 installed in the pipette block 100 are installed in two rows, the first tube rack 440 in which the plurality of target substance receiving tubes 442-1 for receiving isolated protein and separate tubes (not shown) for receiving cell extract used in protein expression are respectively installed in two rows, the waste liquid container 450 for collecting waste liquid discharged from the plurality of pipettes 140 installed in the pipette block 100, and the like are mounted on the base plate 400. Preferably, the separate tubes (not shown) may be installed at a place in which the target substance diagnosing tube 442-3 of example 1 maintained in a refrigerated state is installed. Referring to FIG. 6, the base plate 400 is mounted in the casing 300.

Referring to FIG. 25, the second embodiment includes a step S10 of adding target DNA to a particular unit well.

Referring to FIG. 5, in the step S10 of adding target DNA to the particular unit well, the target DNA is added in a particular unit well L of the multi-well plate 420'. This step is carried out before the base plate 400 is mounted in the casing 300.

Referring to FIG. 25, the second embodiment includes a step S20 of injecting and mixing DEPC distilled water into the particular unit well.

Referring to FIG. 5, in the step S20 of injecting and mixing the DEPC distilled water into the particular unit well, the DEPC distilled water injected into a unit well H of the multi-well plate 420' is injected into the particular unit well L using the pipette 141, 142 (referring to FIG. 2). Thus, the target DNA is mixed with the DEPC distilled water in the particular unit well L. Therefore, a mixture of the DEPC distilled water is produced.

Referring to FIG. 25, the second embodiment includes a step S30 of injecting and mixing an expression solution (5× master mix containing amino acid, dNTP and creatine phosphate) into the particular unit well L.

Referring to FIG. 5, in the step S30 of injecting and mixing a expression solution into the particular unit well, the expression solution injected into a unit well G of the multi-well plate 420' is injected into the particular unit well L using the pipette 141, 142 (referring to FIG. 2). Therefore, the expression solution is mixed with the mixture of the DEPC distilled water in the particular unit well L, and thus a mixture of the expression solution is produced.

Referring to FIG. 25, the second embodiment includes a step S40 of injecting and mixing cell extract into the particular unit well.

Referring to FIG. 5, in the step S40 of injecting and mixing the cell extract into the particular unit well, the cell extract injected into the separate tube (not shown) is injected into the particular unit well L using the pipette 141, 142 (referring to FIG. 2). Therefore, the cell extract is mixed with the mixture of the expression solution in the particular unit well L, and thus a mixture of the cell extract is produced.

Referring to FIG. 25, the second embodiment includes a heating step S50.

Referring to FIGS. 20 and 24, in the heating step S50, the magnet mounting part 710 is lifted up so that the lower portion of the particular unit well L is in a state of being put into the unit well inserting groove 713. Then, the heating part 720 is operated in order to heat the lower portion of the particular unit well L, thereby promoting the protein expression in the mixture of the cell extract. In the heating step S50, a reaction by an enzyme (T7 RNA polymerase) is activated in the mixture of the cell extract, thereby achieving RNA synthesis and protein expression from the target DNA. Thus, a mixture in which protein is expressed is produced. The lower portion of the particular unit well L may be heated for 3 hours at 30~40 degrees Celsius using the heating part 720.

Referring to FIG. 25, the second embodiment includes a step S60 of injecting a first expressed protein into the particular unit well.

Referring to FIG. 5, in the step S60 of injecting the first expressed protein into the particular unit well, a mixture in which protein is expressed is injected into a unit well J of the multi-well plate 420' using the pipette 141, 142 (referring to FIG. 2).

Referring to FIG. 25, the second embodiment includes a step S70 of mixing a magnetic particle binding solution.

Referring to FIG. 5, in the step S70 of mixing the magnetic particle combining solution, the magnetic particle combining solution (binding buffer containing imidazole of 10 mM) injected into a unit well B of the multi-well plate 420 is injected in a unit well F of the multi-well plate 420 using the pipette 141, 142 (referring to FIG. 2) so as to be mixed with magnetic particles. Thus, the expressed protein can be easily bound on the surface of the magnetic particle.

Referring to FIG. 25, the second embodiment includes a step S80 of injecting a binding solution containing magnetic particles into the particular unit well.

Referring to FIGS. 5 and 20, in the step S80 of injecting the binding solution containing magnetic particles into the particular unit well, a mixture of the magnetic particle binding solution and the magnetic particles in the unit well F is injected into the particular unit well L using the pipette 141, 142 (referring to FIG. 2), while the magnet mounting part 710 is lifted down.

Referring to FIG. 25, the second embodiment includes a first magnetic field applying step S90.

Referring to FIGS. 20 and 24, in the first magnetic field applying step S90, the magnet mounting part 710 is lifted up so that the lower portion of the particular unit well L is put into the unit well inserting groove 713. Thus, the magnetic field is applied from the magnet 711 installed at the magnet mounting part 710 to the lower portion of the particular unit well L.

Referring to FIG. 25, the second embodiment includes a first removing step S100. The first removing step S100 is performed in a state that the magnetic field is applied to the lower portion of the particular unit well L through the first magnetic field applying step S90. Therefore, referring to FIG. 24, while the first removing step S100 is performed, the magnetic particles in the mixture of the magnetic particle binding solution and the magnetic particles are maintained in a state of being attached to a lower inner surface of the particular unit well L by the magnetic field.

Referring to FIG. 5, in the first removing step S100, the magnetic particle binding solution is removed from the mixture of the magnetic particle binding solution and the magnetic particles by using the pipette 141, 142 (referring to FIG. 2). The magnetic particle binding solution removed in the first removing step S100 is discharged to the waste liquid container 450. As the first removing step S100 is carried out, the magnetic particles are remained in the particular unit well L.

Referring to FIG. 25, the second embodiment includes a step S110 of injecting a second expressed protein into the particular unit well.

Referring to FIG. 5, in the step S110 of injecting the second expressed protein into the particular unit well, a mixture in which protein is expressed in the unit well J is injected into the particular unit well L using the pipette 141, 142 (referring to FIG. 2).

Referring to FIG. 25, the second embodiment includes a step S120 of mixing magnetic particles and expressed protein.

Referring to FIG. 5, in the step S120 of mixing the magnetic particles and the expressed protein, the mixture in which protein is expressed and injected into the particular unit well L and the magnetic particles are mixed using the pipette 141, 142 (referring to FIG. 2). Therefore, a mixture of the magnetic particles is produced, and thus protein in the mixture in which protein is expressed is bound on the surface of the magnetic particle.

Referring to FIG. 25, the second embodiment includes a second magnetic field applying step S130.

Referring to FIGS. 20 and 24, in the second magnetic field applying step S130, the magnetic mounting part 710 is lifted up so that the lower portion of the particular unit well L is put into the unit well inserting groove 713. Therefore, the magnetic field is applied from the magnet 711 installed at the magnetic mounting part 710 to the lower portion of the particular unit well L.

Referring to FIG. 25, the second embodiment includes a second removing step S140. The second removing step S140 is performed in a state that the magnetic field is applied to the lower portion of the particular unit well L through the second magnetic field applying step S130. Therefore, referring to FIG. 24, while the second removing step S140 is performed, the magnetic particles and the protein bound on the magnetic particles in the mixture of the magnetic particles are maintained in a state of being attached to the lower inner surface of the particular unit well L by the magnetic field.

Referring to FIG. 5, in the second removing step S140, the mixture except the magnetic particles and the protein bound on the magnetic particles is removed from the mixture of the magnetic particles by using the pipette 141, 142 (referring to FIG. 2). The mixture removed in the second removing step S140 can be discharged to the waste liquid container 450 or a unit well K of the multi-well plate 420'. As the second removing step S140 is carried out, the magnetic particles and the protein bound on the magnetic particles are remained in the particular unit well L.

Referring to FIG. 25, the second embodiment includes a step S150 of injecting a washing solution (washing buffer containing Tris-Cl, NaCl and imidazole of 50 mM) in the particular unit well and then performing a washing operation.

Referring to FIGS. 5 and 20, in the step S150 of injecting the washing solution in the particular unit well and then performing the washing operation, while the magnet mounting part 710 is lifted down, a first washing solution injected in a unit well C of the multi-well plate 420 is injected and mixed in the particular unit well L using the pipette 141, 142 (referring to FIG. 2), and then impurities except the protein as the target substance are isolated from the magnetic particles.

Referring to FIG. 25, the second embodiment includes a third magnetic field applying step S160.

Referring to FIGS. 20 and 24, in the third magnetic field applying step S160, the magnetic mounting part 710 is lifted up so that the lower portion of the particular unit well L is put into the unit well inserting groove 713. Therefore, the magnetic field is applied from the magnet 711 installed at the magnetic mounting part 710 to the lower portion of the particular unit well L.

Referring to FIG. 25, the second embodiment includes a third removing step S170. The third removing step S170 is performed in a state that the magnetic field is applied to the lower portion of the particular unit well L through the third magnetic field applying step S160. Therefore, referring to FIG. 24, while the third removing step S170 is performed, the magnetic particles, on which the protein is attached, in the mixture of the first washing solution are maintained in a state of being attached to the lower inner surface of the particular unit well L by the magnetic field.

Referring to FIG. 5, in the third removing step S170, the mixture except the magnetic particles on which the protein is attached is removed from the mixture of the first washing solution by using the pipette 141, 142 (referring to FIG. 2). The mixture removed in the third removing step S170 can be discharged to the waste liquid container 450 or a unit well I of the multi-well plate 420'. As the third removing step S170 is carried out, the magnetic particles on which protein is attached are remained in the particular unit well L.

In the second embodiment, the step S150 of injecting the washing solution in the particular unit well and then performing the washing operation, the third magnetic field applying step S160 and the third removing step S170 may be repeatedly carried out in turn. In this case, in the step S150 of injecting the washing solution in the particular unit well and then performing the washing operation, the first washing solution injected into a unit well C of the multi-well plate 420 (referring to FIG. 5) and a second washing solution injected into a unit well D of the multi-well plate 420 (referring to FIG. 5) are injected into the particular unit well L by the same manner. The third magnetic field applying step S160 is carried out in the same manner, and the third removing step S170 is also carried out in the same manner.

Referring to FIG. 25, the second embodiment includes a step S180 of injecting an elution solution (elution buffer containing imidazole of 500 ml) in the particular unit well and purifying a target protein.

Referring to FIGS. 5 and 20, in the step S180 of injecting the elution solution in the particular unit well and purifying the target protein, while the magnet mounting part 710 is lifted down, a protein elution solution injected into a unit well E of the multi-well plate 420 is injected and mixed into the particular unit well L using the pipette 141, 142 (referring to FIG. 2), and the protein is isolated from the magnetic particles. Therefore, a mixture of the protein elution solution is produced.

Referring to FIG. 25, the second embodiment includes a fourth magnetic field applying step S190. The fourth magnetic field applying step S190 is carried out when a desired time passes after the step S180 of injecting the elution solution in the particular unit well and purifying the target protein.

Referring to FIGS. 20 and 24, in the fourth magnetic field applying step S190, the magnetic mounting part 710 is lifted up so that the lower portion of the particular unit well L is put into the unit well inserting groove 713. Therefore, the magnetic field is applied from the magnet 711 installed at the magnetic mounting part 710 to the lower portion of the particular unit well L.

Referring to FIG. 25, the second embodiment includes a step S200 of obtaining a target substance containing solution. The step S200 of obtaining the target substance containing solution is carried out in a state that the magnetic field is applied to the lower portion of the particular unit well L through the fourth magnetic field applying step S190. Therefore, referring to FIG. 24, while the step S200 of obtaining the target substance containing solution is carried out, the magnetic particles in the mixture of the protein elution solution are maintained in a state of being attached to the lower inner surface of the particular unit well L by the magnetic field.

Referring to FIG. 5, in the step S200 of obtaining the target substance containing solution, the target substance containing solution, a mixture except the magnetic particles in the mixture of the protein elution solution, is injected and stored in the target substance receiving tube 442-1 installed at the base plate 400 using the pipette 141, 142 (referring to FIG. 2).

Third Embodiment

A third embodiment relates to an automatic biological sample purification apparatus equipped with a magnetic field applying part according to the present invention, which can isolate a target substance reversibly bound with magnetic particles from a plurality of biological samples using the magnetic particles.

Since the third embodiment is similar to the first embodiment, the same reference numerals and technical terms are used for the same elements, and the description thereof will be omitted.

Figure 26:
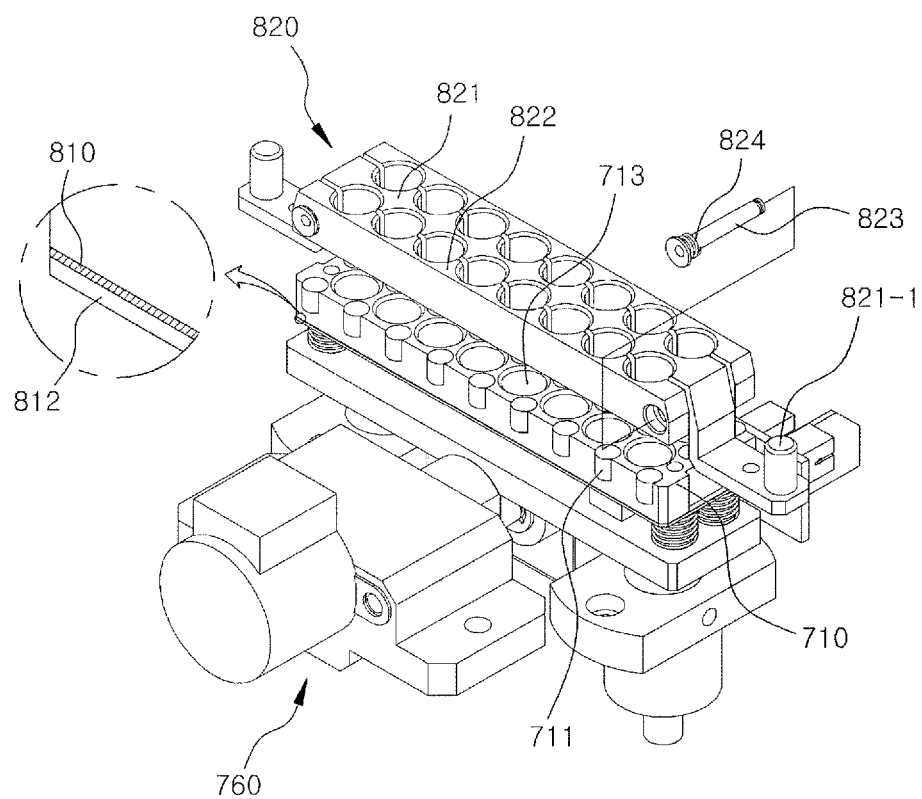
FIG. 26 is a perspective view of a magnet mounting part, a lifting part and an auxiliary heating part according to a third embodiment of the present invention.
Figure 27:
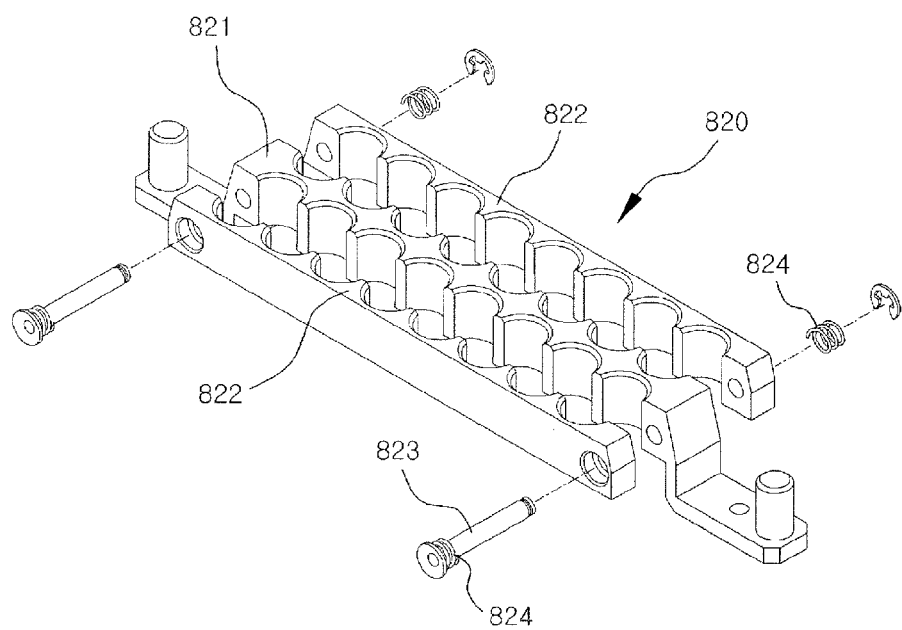
FIG. 27 is an exploded perspective view of the auxiliary heating part according to the third embodiment of the present invention.
Figure 28:
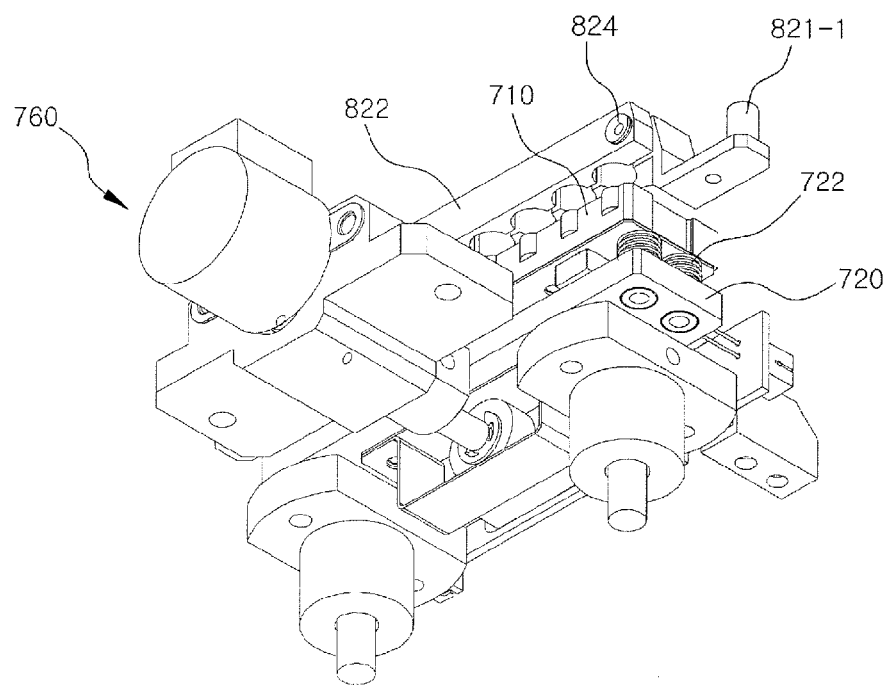
FIG. 28 is a bottom perspective view when the magnet mounting part is lifted down according to the third embodiment of the present invention.
Figure 29:
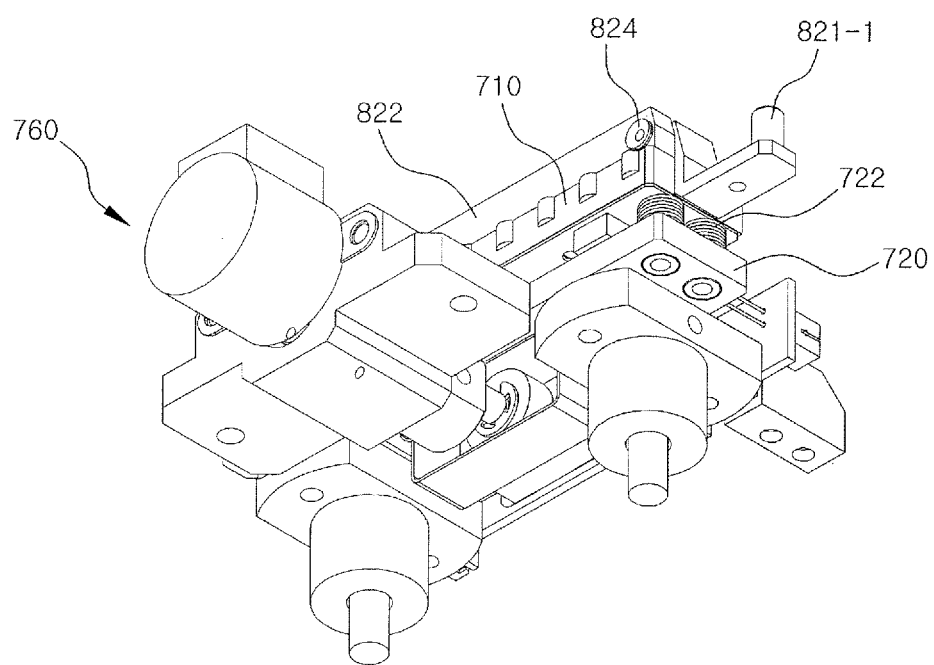
FIG. 29 is a bottom perspective view when the magnet mounting part is lifted up according to the third embodiment of the present invention.
Figure 30:
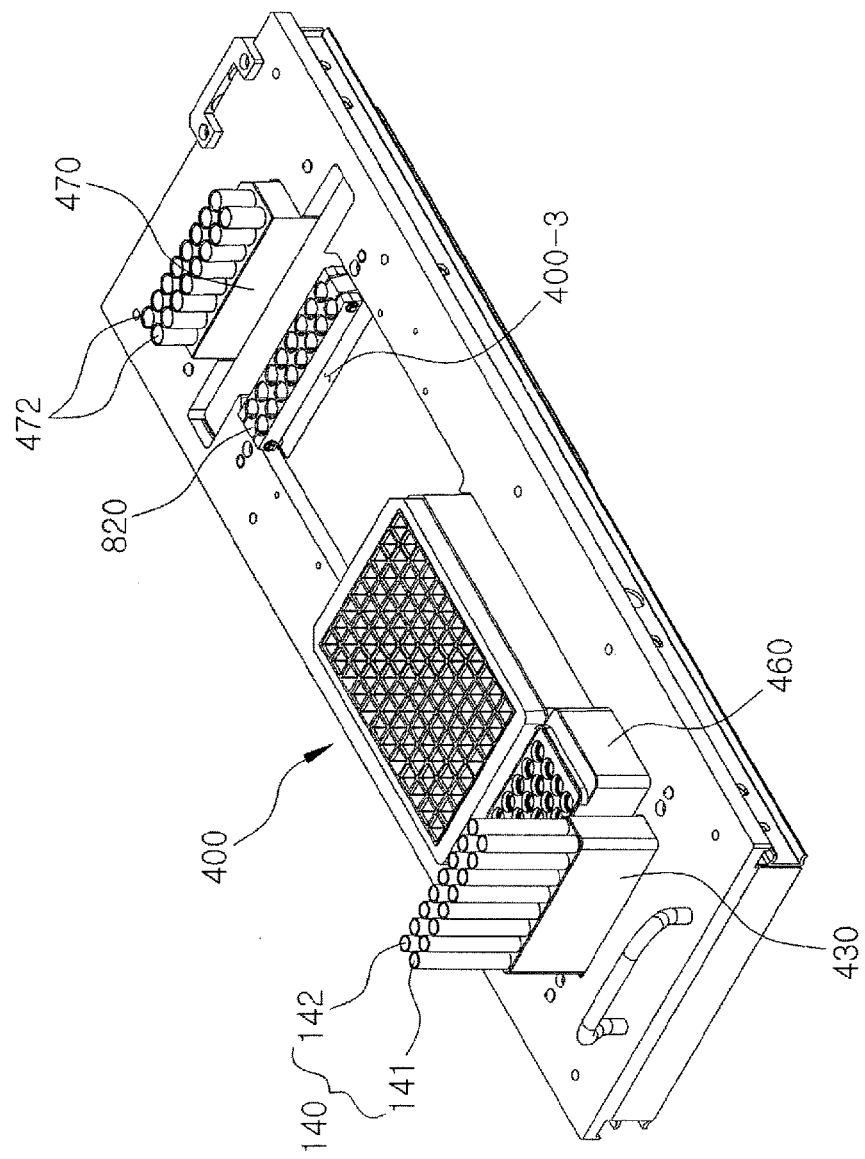
FIG. 30 is a view showing a state that the auxiliary heating part is installed at the base plate according to the third embodiment of the present invention.
Figure 31:
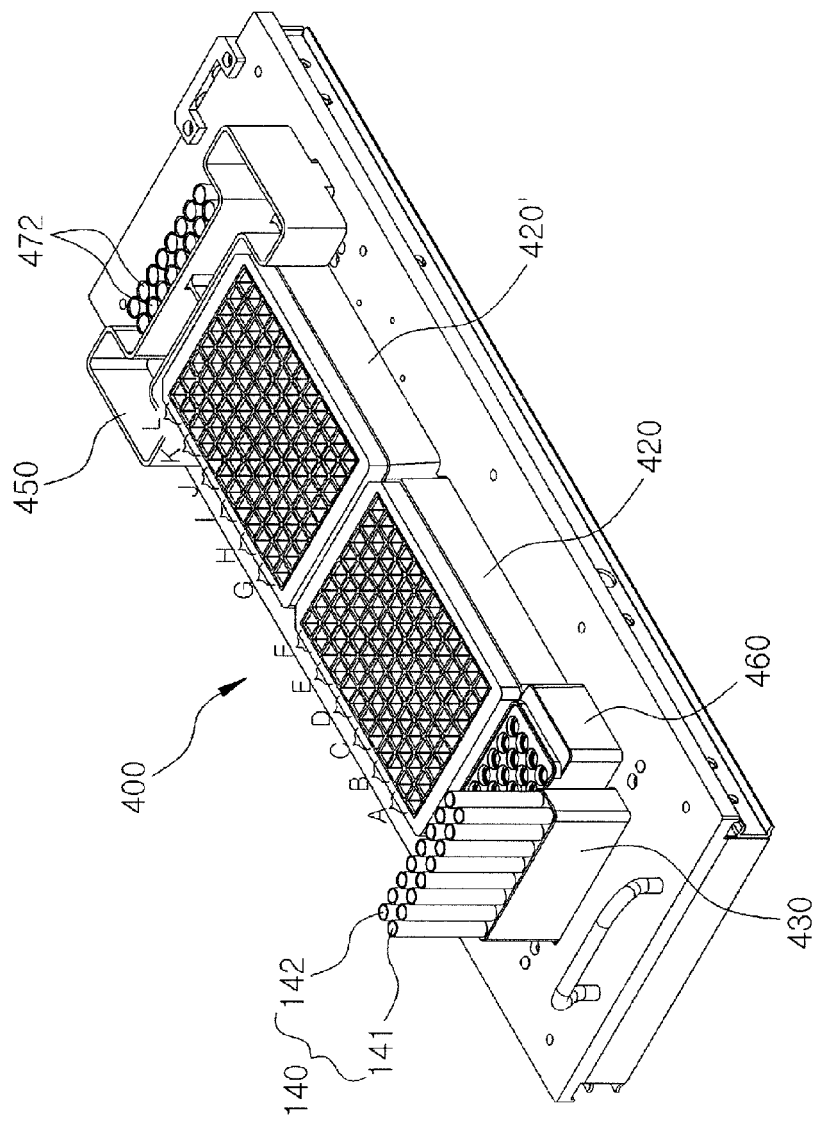
FIG. 31 is a view showing a using state of the base plate according to the third embodiment of the present invention.
Figure 32:
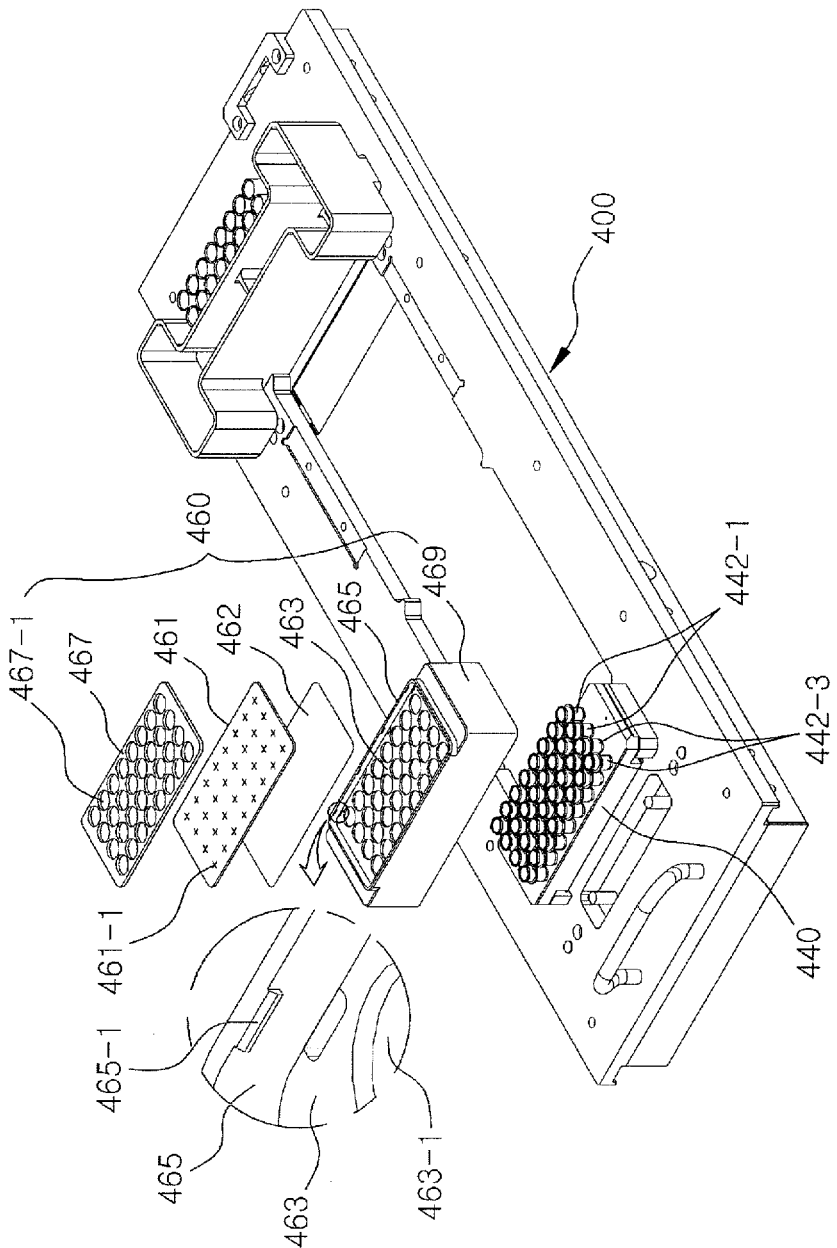
FIG. 32 is a view showing a state of the base plate before a contamination preventing device is installed according to the third embodiment of the present invention.
Figure 33:
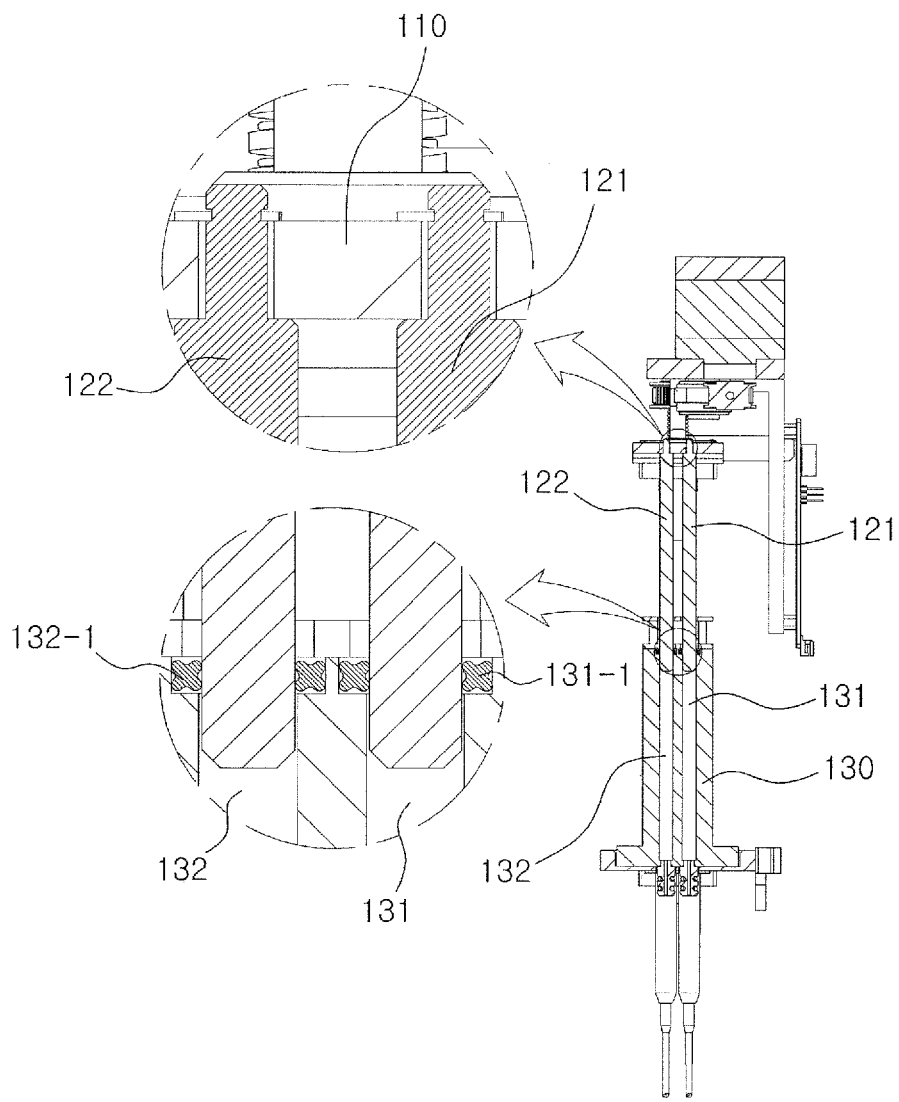
FIG. 33 is a view showing an installation state of a syringe pin and an X-ring according to the third embodiment of the present invention.
Figure 34:
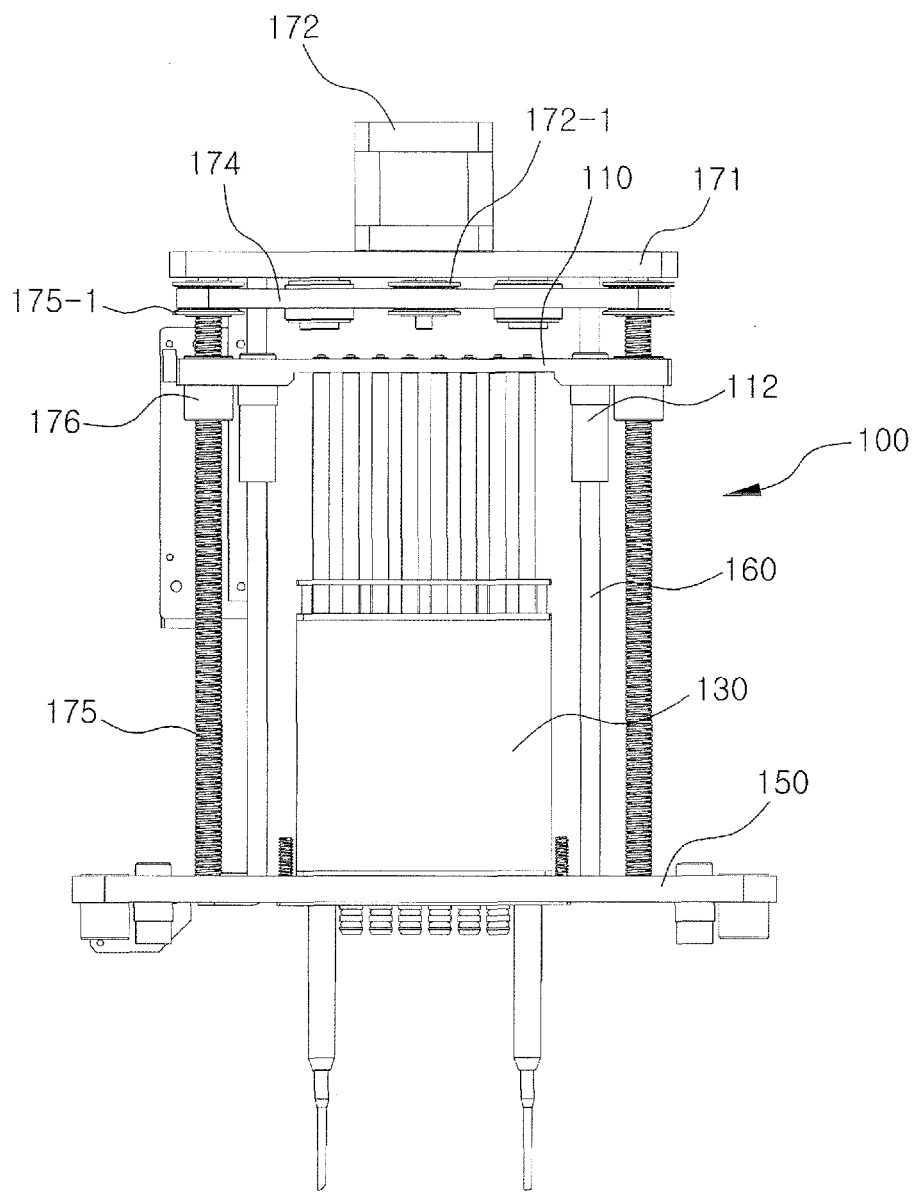
FIG. 34 is a schematic view of a pipette block according to the third embodiment of the present invention.

FIG. 26 is a perspective view of a magnet mounting part, a lifting part and an auxiliary heating part according to a third embodiment of the present invention, FIG. 27 is an exploded perspective view of the auxiliary heating part according to the third embodiment of the present invention, FIG. 28 is a bottom perspective view when the magnet mounting part is lifted down according to the third embodiment of the present invention, FIG. 29 is a bottom perspective view when the magnet mounting part is lifted up according to the third embodiment of the present invention, FIG. 30 is a view showing a state that the auxiliary heating part is installed at the base plate according to the third embodiment of the present invention, FIG. 31 is a view showing a using state of the base plate according to the third embodiment of the present invention, FIG. 32 is a view showing a state of the base plate before a contamination preventing device is installed according to the third embodiment of the present invention, FIG. 33 is a view showing an installation state of a syringe pin and an X-ring according to the third embodiment of the present invention, and FIG. 34 is a schematic view of a pipette block according to the third embodiment of the present invention.

Referring to FIG. 30, the third embodiment includes an auxiliary heating part 820 fixed to the base plate 400. Referring to FIGS. 28 and 29, the auxiliary heating part 820 is installed at the base plate 400 so that a lower surface of the auxiliary heating part 820 is contacted with an upper surface of the magnet mounting part 710 when the magnet mounting part 710 is move up. Therefore, as the heating part 810 is operated, heat transfer from the magnet mounting part 710 to the auxiliary heating part 820 is facilely occurred.

Referring to FIGS. 26 and 27, the auxiliary heating part 820 includes a first body 821, a second body 822 and a tightly-contacting spring 824.

Referring to FIGS. 26 and 27, a first body inserting groove (not designated by a reference numeral) corresponding to an outer surface of one side of the particular unit well L of the multi-well plate 420' is formed at a side surface of the first body 821. Therefore, if the multi-well plate 420' is installed at the base plate 400, the outer surface of the one side of the particular unit well L of the multi-well plate 420' is contacted with the first body inserting groove (not designated by a reference numeral).

Referring to FIGS. 26 and 27, a second body inserting groove (not designated by a reference numeral) corresponding to an outer surface of the other side of the particular unit well L of the multi-well plate 420' is formed at a side surface of the second body 822. Therefore, if the multi-well plate 420' is installed at the base plate 400, the outer surface of the other side of the particular unit well L of the multi-well plate 420' is contacted with the second body inserting groove (not designated by a reference numeral).

Referring to FIGS. 26 and 27, a sliding rod 823 is protruded at the side surface of the first body 821. The second body 822 is formed with a sliding hole (not designated by a reference numeral). The second body 822 is inserted onto the sliding rod 823 through the sliding hole (not designated by a reference numeral), and thus the second body 822 is slidably installed at the sliding rod 823. Meanwhile, the second body 822 is formed with a spring mounting hole (not designated by a reference numeral). The spring mounting hole (not designated by a reference numeral) is communicated with the sliding hole (not designated by a reference numeral) and also has a larger diameter than the sliding hole (not designated by a reference numeral). The tightly-contacting spring 824 is installed in the spring mounting hole (not designated by a reference numeral). The tightly-contacting spring 824 is inserted on the sliding rod 823 and installed in the spring mounting hole (not designated by a reference numeral). One end of the tightly-contacting spring 824 is elastically supported to a ring-shaped boundary surface between the spring mounting hole (not designated by a reference numeral) and the sliding hole (not designated by a reference numeral). The other end of the tightly-contacting spring 824 is elastically supported to a head portion of the sliding rod which is formed at a protruded end of the sliding rod 823 or a washer which is fitted onto a protruded end of the sliding rod 823. Therefore, if the particular unit well L of the multi-well plate 420, 420' is inserted into a space formed by the first body inserting groove (not designated by a reference numeral) and the second body inserting groove (not designated by a reference numeral) while overcoming the elastic force of the tightly-contacting spring 824, the circumferential surface of the particular unit well L is tightly contacted with the first and second bodies 821 and 822 by the elastic force of the tightly-contacting spring 824. Therefore, heat transfer from the auxiliary heating part 820 to the particular unit well L is facilely occurred. Meanwhile, the first body 821 is formed with a fixing part 821-1 for fixing the auxiliary heating part 820 to the base plate 400.

Referring to FIGS. 28 and 29, the magnet mounting part 710 is elastically supported by a buffer spring 722 and also mounted on the magnet mounting part supporter 720 so as to be movable up and down. Therefore, a guiding rod (not shown) for magnet mounting part, which guides up and down movement of the magnet mounting part 710 is formed at the magnet mounting part supporter 720, and the buffer spring 722 may be inserted onto the guiding rod (not shown) for magnet mounting part. When the upper surface of the magnet mounting part 710 is contacted with a lower surface of the auxiliary heating part 820, shock is relieved by the buffer spring 722 and they are contacted slowly with each other.

Referring to FIGS. 30 and 31, besides the multi-well plate 420, 420', there are mounted a pipette rack 430, a contamination preventing device 460, a waste liquid container 450 and a second tube rack 470 on the base plate 400.

Referring to FIG. 32, a first tube rack 440 for receiving tubes 442-1 and 442-3 for target substance is mounted on the base plate 400. The tubes 442-1 and 442-3 for target substance includes a plurality of target substance receiving tubes 442-1 for receiving a purified target substance and a plurality of target substance diagnosing tubes 442-3 for diagnosing the purified target substance. The contamination preventing device 460 is to block upper ends of the tubes 442-1 and 442-3 for target substance and thus to prevent aerosol generated from the purified target substance from being diffused to the outside of the tubes 442-1 and 442-3 for target substance when the purified target substance is discharged from a plurality of pipettes 141 and 142.

Referring to FIG. 32, the contamination preventing device 460 includes a cover film 461 and a film supporter (not designated by a reference numeral). The cover film 461 is formed with a cut line 461-1 which is gaped by pressing force of the plurality of pipettes 141 and 142 so as to allow the lower portions of the pipettes 141 and 142 to be passed therethrough. The cover film 461 is formed of an elastic material so that the cut line 461-1 can be recovered to its original state when the plurality of pipettes 141 and 142 are moved up and separated from the cut line 461-1.

Referring to FIG. 32, the film supporter (not designated by a reference numeral) functions to support the cover film 461 so that the cut line 461-1 is located at the upper side of the tubes 442-1 and 442-3 for target substance. The film supporter (not designated by a reference numeral) includes a settle plate 463, a horizontal movement preventing plate 465, a vertical movement preventing plate 467 and a settle plate supporter 469.

Referring to FIG. 32, the settle plate 463 is formed into a flat plate in order to support a lower surface of the cover film 461. The settle plate 463 is formed with a through-hole 463-1 in which an upper end of the tube 442-1, 442-3 for target substance is inserted.

Referring to FIG. 32, the horizontal movement preventing plate 465 is mounted on an upper surface of the settle plate 463 so as to be contacted with an outer surface of the cover film 461, thereby preventing a horizontal movement of the cover film 461.

Referring to FIG. 32, the vertical movement preventing plate 467 is mounted on an upper surface of the cover film 461 so as to prevent a vertical movement of the cover film 461. The vertical movement preventing plate 467 is formed into a flat plate and also formed with an exposing hole 467-1 which exposes the cut line 461-1 of the cover film 461. Meanwhile, the horizontal movement preventing plate 465 is formed with a prevention protrusion 465-1 which is contacted with an upper surface of the vertical movement preventing plate 467 in order to prevent the vertical movement preventing plate 467 from being separated upward.

Referring to FIG. 32, the settle plate supporter 469 is inserted onto the first tube rack 440 so that a lower end of the settle plate supporter 469 is installed at the base plate 400. An upper end of the settle plate supporter 469 is connected with the settle plate 463 so as to support the settle plate 463.

Referring to FIG. 32, a foil 462 which can be punched by pressing force of the pipettes 141 and 142 may be disposed between the settle plate 463 and the cover film 461.

Referring to FIG. 30, the waste liquid container 450 is mounted on the base plate 400 so as to be adjacent to a unit well exposing hole 400-3.

Referring to FIGS. 30 and 31, a biological sample tube 472 in which a biological sample is injected is received in the second tube rack 470. The biological sample tube 472 is disposed so as to be opposed to the unit well exposing hole 400-3 with the waste liquid container 450 in the center.

Referring to FIG. 33, a closed curve-shaped X ring 131-1, 132-1 having an X shape in transverse section is installed in a syringe pin guiding hole 131, 132. The X ring 131-1, 132-1 is disposed at an upper end of the syringe pin guiding hole 131, 132. Since upper and lower portions of the X ring 131-1, 132-1 are simultaneously contacted with a syringe pin 121, 122, it has an effect of using two O-rings, and thus air tightness between the syringe pin 121, 122 and the syringe pin guiding hole 131, 132 is enhanced. Further, since the upper and lower portions of the X ring 131-1, 132-1, except a middle portion thereof, are contacted with the syringe pin 121, 122, it is possible to further reduce frictional force generated when the syringe pin 121, 122 is moved up and down along the syringe pin guiding hole 131, 132, comparing with the O-ring having the same thickness.

Referring to FIG. 33, a syringe pin fixing hole (not designated by a reference numeral) in which an upper end of the syringe pin 121, 122 is fitted is formed in a syringe pin holder 110. The syringe pin fixing hole (not designated by a reference numeral) is formed to maintain a gap with the upper end of the syringe pin 121, 122 when the upper end of the syringe pin 121, 122 is fitted in the syringe pin fixing hole (not designated by a reference numeral). In case that the upper end of the syringe pin 121, 122 is fitted in the syringe pin fixing hole (not designated by a reference numeral), the syringe pin 121, 122 can be somewhat moved horizontally due to the gap. Therefore, even through some errors are occurred in the forming of the syringe pin guiding hole 131, 132 and the syringe pin fixing hole (not designated by a reference numeral), the syringe pin 120 can be facilely fitted to the syringe pin guiding hole 131, 132 and also can be smoothly moved up and down along the syringe pin guiding hole 131, 132.

Referring to FIG. 34, a first driving pulley 172-1 for syringe pin is connected to a syringe pin adjusting motor 172. An upper end of an up and down moving screw 175 for syringe pin is connected with a supporting plate 171 for syringe pin adjusting motor, and a lower end thereof is connected with a supporting plate 150 for syringe pin guiding block. The up and down moving screw 175 for syringe pin is rotatably disposed at the supporting plate 171 for syringe pin adjusting motor and the supporting plate 150 for syringe pin guiding block.

Referring to FIG. 34, an up and down moving nut 176 for syringe pin is inserted onto the up and down moving screw 175 for syringe pin. The up and down moving nut 176 for syringe pin is fixed to a syringe pin holder 110. A second driving pulley 175-1 for syringe pin is installed at the upper end of the up and down moving screw 175 for syringe pin.

Referring to FIG. 34, a driving belt 174 for syringe pin is wound on the first and second driving pulleys 172-1 and 175-1 for syringe pin. Therefore, as the driving belt 174 for syringe pin is moved, the syringe pin holder 110 is moved up and down.

Fourth Embodiment

Figure 35:
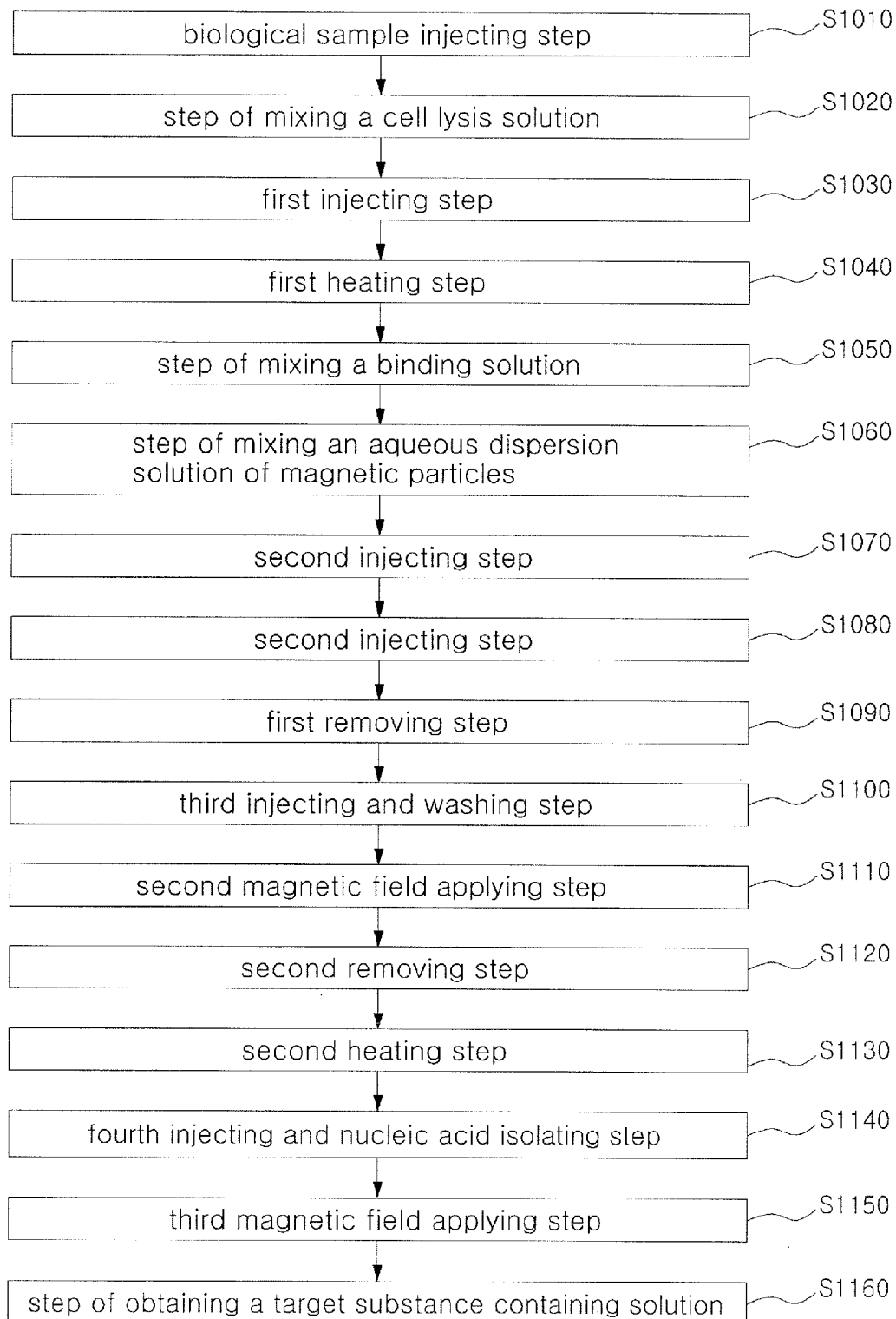
FIG. 35 is a flow chart according to a fourth embodiment of the present invention.

A fourth embodiment relates to a method of extracting nucleic acid as a target substance from a biological sample using the third embodiment.
FIG. 35 is a flow chart according to a fourth embodiment of the present invention. In order to carry out the fourth embodiment, a preparing process has to be performed firstly.

Referring to FIGS. 30 to 32, in the preparing process, the second tube rack 470 in which the biological sample tube 472 is installed is mounted on the backmost side of the base plate 400. The waste liquid container 450 for receiving the waste liquid used in the extraction of target substance is sequentially mounted on the base plate 400. Then, the two multi-well plates 420 and 420' used in the extraction of target substance, the first tube rack 440 in which the plurality of target substance receiving tubes 442-1 for receiving the extracted target substance and the plurality of target substance diagnosing tubes 442-3 for receiving a diagnostic kit or a diagnostic reagent are respectively installed in two rows, and the pipette rack 430 in which the plurality of pipettes 140 are received in two rows are mounted on the base plate 400. Referring to FIG. 6, the base plate 400 is mounted into the casing 300.

Referring to FIG. 35, the fourth embodiment includes a biological sample injecting step S1010.

Referring to FIGS. 30 and 31, in the biological sample injecting step S1010, a biological sample is injected into each of the biological sample tube 472 using a micro-pipette. The biological sample injecting step S1010 is carried out before the base plate 400 is mounted into the casing 300.

Referring to FIG. 35, the fourth embodiment includes a step S1020 of mixing a cell lysis solution.

Referring to FIG. 31, in the step S1020 of mixing the cell lysis solution, the cell lysis solution injected into a unit well K of the multi-well plate 420 is injected into a unit well J of the multi-well plate 420' using the pipette 141, 142 (referring to FIG. 2). Then, a protease in the unit well J of the multi-well plate 420' is completely mixed with the cell lysis solution injected into the unit well J of the multi-well plate 420' using the pipette 141, 142 (referring to FIG. 2). Therefore, a mixture of the cell lysis solution is produced in the unit well J. Then, the mixture of the cell lysis solution is injected into the biological sample tube 472 using the pipette 141, 142 (referring to FIG. 2). And the mixture of the cell lysis solution is mixed with the biological sample using the pipette 141, 142 (refer-ring to FIG. 2). Therefore, a mixture of the biological sample is produced in the biological sample tube 472.

Referring to FIG. 35, the fourth embodiment includes a first injecting step S1030.

Referring to FIG. 31, in the first injecting step S1030, the mixture of the biological sample is injected into a particular unit well L of the multi-well plate 420' using the pipette 141, 142 (referring to FIG. 2).

Referring to FIG. 35, the fourth embodiment includes a first heating step S1040.

Referring to FIG. 24, FIG. 26 and FIG. 28, in the first heating step S1040, the magnet mounting part 710 is lifted up so that the lower portion of the particular unit well L is in a state of being put into the unit well inserting groove 713. Then, the heating part 720 is operated in order to heat the lower portion of the particular unit well L, thereby promoting the cell lysis of the biological sample mixed with the cell lysis solution. A protease for cell lysis and protein degradation may be injected and sealed in the unit well J of the multi-well plate 420' (referring to FIG. 31) according to the biological samples. In the first heating step S1040, a reaction by the protease is activated, thereby rapidly and completely performing the cell lysis of the biological sample. The lower portion of the particular unit well L may be heated for 10 minutes at 65 degrees Celsius using the heating part 720.

Referring to FIG. 35, the fourth embodiment includes a step S1050 of mixing a binding solution.

Referring to FIG. 31, in the step S1050 of mixing the binding solution, the cell lysis solution and the biological sample of which the cell lysis is performed are mixed with the binding solution injected into a unit well I of the multi-well plate 420' using the pipette 141, 142 (referring to FIG. 2). That is, in the step S1050 of mixing the binding solution, the mixture in which the enzyme reaction is performed in the particular unit well L is injected into the unit well I of the multi-well plate 420'. The binding solution may be alcohol (isopropyl alcohol, ethyl alcohol) for enhancing binding force between nucleic acid as the target substance and magnetic particles.

Referring to FIG. 35, the fourth embodiment includes a step S1060 of mixing an aqueous dispersion solution of magnetic particles.

Referring to FIG. 31, in the step S1060 of mixing the aqueous dispersion solution of magnetic particles, the mixture mixed with the binding solution is mixed with the aqueous dispersion solution of magnetic particles injected into a unit well H of the multi-well plate 420' using the pipette 141, 142 (referring to FIG. 2). Therefore, the nucleic acid is attached on the surface of the magnetic particles. That is, as the step S1060 of mixing the aqueous dispersion solution of magnetic particles is carried out, the mixture mixed with the binding solution is injected into the unit well H of the multi-well plate 420'.

Referring to FIG. 35, the fourth embodiment includes a second injecting step S1070.

Referring to FIGS. 24, 26 and 28, in the second injecting step S1070, while the magnet mounting part 710 is lifted down, the mixture mixed with the aqueous dispersion solution of magnetic particles is injected into the particular unit well L using the pipette 141, 142 (referring to FIG. 2). Since the second injecting step S1070 is carried out in the state that the magnet mounting part 710 is lifted down, the nucleic acid as the target substance is moved from the unit well H of the multi-well plate 420' to the particular unit well L in a state of being attached to the surface of the magnetic particle.

Referring to FIG. 35, the fourth embodiment includes a first magnetic field applying step S1080. The first magnetic field applying step S1080 is carried out when a desired time passes after the second injecting step S1070.

Referring to FIGS. 24 and 26, in the first magnetic field applying step S1080, the magnet mounting part 710 is lifted up so that the lower portion of the particular unit well L is put into the unit well inserting groove 713. Thus, the magnetic field is applied from the magnet 711 installed at the magnet mounting part 710 to the lower portion of the particular unit well L.

Referring to FIG. 35, the fourth embodiment includes a first removing step S1090. The first removing step S1090 is performed in a state that the magnetic field is applied to the lower portion of the particular unit well L through the first magnetic field applying step S1080. Therefore, referring to FIG. 24, while the first removing step S1090 is performed, the magnetic particles and the substance attached to the magnetic particles in the mixture mixed with the aqueous dispersion solution of magnetic particles are maintained in a state of being attached to a lower inner surface of the particular unit well L by the magnetic field.

Referring to FIG. 31, in the first removing step S1090, the mixture except the magnetic particles and the substance attached to the magnetic particles is removed from the mixture mixed with the aqueous dispersion solution of magnetic particles by using the pipette 141, 142 (referring to FIG. 2). The mixture removed in the first removing step S1090 is discharged to the waste liquid container 450 or the unit well H of the multi-well plate 420'. As the first removing step S1090 is carried out, the magnetic particles and the substance attached to the magnetic particles are remained in the particular unit well L.

Referring to FIG. 35, the fourth embodiment includes a third injecting and washing step S1100.

Referring to FIGS. 26 and 31, in the third injecting and washing step S1100, while the magnet mounting part 710 is lifted down, a first washing solution injected into a unit well G of the multi-well plate 420' is injected into the particular unit well L using the pipette 141, 142 (referring to FIG. 2). Then, the mixture in the particular unit well L is transferred to the inside of the pipette 141, 142 (referring to FIG. 2) and then discharged. This process is repeatedly performed in order to wash impurities in the substance attached to the surface of the magnetic particle, except the nucleic acid.

Referring to FIG. 35, the fourth embodiment includes a second magnetic field applying step S1110.

Referring to FIGS. 24 and 26, in the second magnetic field applying step S1110, the magnet mounting part 710 is lifted up so that the lower portion of the particular unit well L is put into the unit well inserting groove 713. Therefore, the magnetic field is applied from the magnet 711 installed at the magnetic mounting part 710 to the lower portion of the particular unit well L.

Referring to FIG. 35, the fourth embodiment includes a second removing step S1120. The second removing step S1120 is performed in a state that the magnetic field is applied to the lower portion of the particular unit well L through the second magnetic field applying step S1110. Therefore, referring to FIG. 24, while the second removing step S1120 is performed, the magnetic particles, on which the nucleic acid is attached, in the mixture mixed with the washing solution are maintained in a state of being attached to the lower inner surface of the particular unit well L by the magnetic field.

Referring to FIG. 31, in the second removing step S1120, the mixture except the magnetic particles on which the nucleic acid is attached is removed from the mixture mixed with the washing solution by using the pipette 141, 142 (referring to FIG. 2). The mixture removed in the second removing step S1120 can be discharged to the waste liquid container 450 or a unit well G of the multi-well plate 420'. As the second removing step S1120 is carried out, the magnetic particles on which the nucleic acid is attached are remained in the particular unit well L.

In the fourth embodiment, the third injecting and washing step S1100, the second magnetic field applying step S1110 and the second removing step S1120 may be repeatedly carried out in turn. In this case, in the third injecting and washing step S1100, a second washing solution injected into a unit well F of the multi-well plate 420 (referring to FIG. 31), a third washing solution injected into a unit well E of the multi-well plate 420 (referring to FIG. 31) and a fourth washing solution injected into a unit well D of the multi-well plate 420 (referring to FIG. 31) are injected into the particular unit well L by the same manner. The second magnetic field applying step S1110 is carried out in the same manner. The second removing step S1120 is carried out in the same manner. Herein, the removed mixture may be discharged to each of the unit well F of the multi-well plate 420 (referring to FIG. 31), the unit well E of the multi-well plate 420 (referring to FIG. 31) and the unit well D of the multi-well plate 420 (referring to FIG. 31) or the waste liquid container 450. Meanwhile, the third and fourth washing solutions may contain alcohol.

Referring to FIG. 35, the fourth embodiment includes a second heating step S1130.

Referring to FIGS. 24 and 26, in the second heating step S1130, the magnet mounting part 710 is lifted up so that the lower portion of the particular unit well L is in a state of being put into the unit well inserting groove 713. Then, the heating part 720 is operated in order to heat the lower portion of the particular unit well L, thereby removing the alcohol contained in the third and fourth washing solutions remained on the magnetic particles.

Referring to FIG. 35, the fourth embodiment includes a fourth injecting and nucleic acid isolating step S1140.

Referring to FIGS. 26 and 31, in the fourth injecting and nucleic acid isolating step S1140, while the magnet mounting part 710 is lifted down, a nucleic acid elution solution injected into a unit well B of the multi-well plate 420 is injected into the particular unit well L, thereby isolating the nucleic acid from the magnetic particles.

Referring to FIG. 35, the fourth embodiment includes a third magnetic field applying step S1150. The third magnetic field applying step S1150 is carried out when a desired time passes after the fourth injecting and nucleic acid isolating step S1140.

Referring to FIGS. 24 and 26, in the third magnetic field applying step S1150, the magnetic mounting part 710 is lifted up so that the lower portion of the particular unit well L is put into the unit well inserting groove 713. Therefore, the magnetic field is applied from the magnet 711 installed at the magnetic mounting part 710 to the lower portion of the particular unit well L.

Referring to FIG. 35, the fourth embodiment includes a step S1160 of obtaining a target substance containing solution. The step S1160 of obtaining the target substance containing solution is carried out in a state that the magnetic field is applied to the lower portion of the particular unit well L through the third magnetic field applying step S1150. Therefore, referring to FIG. 24, while the step S1160 of obtaining the target substance containing solution is carried out, the magnetic particles in the nucleic acid elution solution containing the isolated nucleic acid are maintained in a state of being attached to the lower inner surface of the particular unit well L by the magnetic field.

Referring to FIG. 31, in the step S1160 of obtaining the target substance containing solution, the target substance containing solution, a mixture except the magnetic particles in the nucleic acid elution solution containing the isolated nucleic acid is injected and stored in the target substance receiving tube 442-1 installed at the base plate 400 using the pipette 141, 142 (referring to FIG. 2).

Referring to FIG. 31, in the step S1160 of obtaining the target substance containing solution, the target substance containing solution may be injected into the target substance diagnosing tube 442-3 installed at the base plate 400 using the pipette 141, 142 (referring to FIG. 2) and then a necessary test may be performed immediately.

Fifth Embodiment

A fifth embodiment relates to an automatic biological sample purification apparatus equipped with a magnetic field applying part according to the present invention, which can isolate the target substance reversibly bound with magnetic particles from a plurality of biological samples using the magnetic particles.

Since the fifth embodiment is similar to the first and third embodiments, the same reference numerals and technical terms are used for the same elements, and the description thereof will be omitted.

Figure 36:
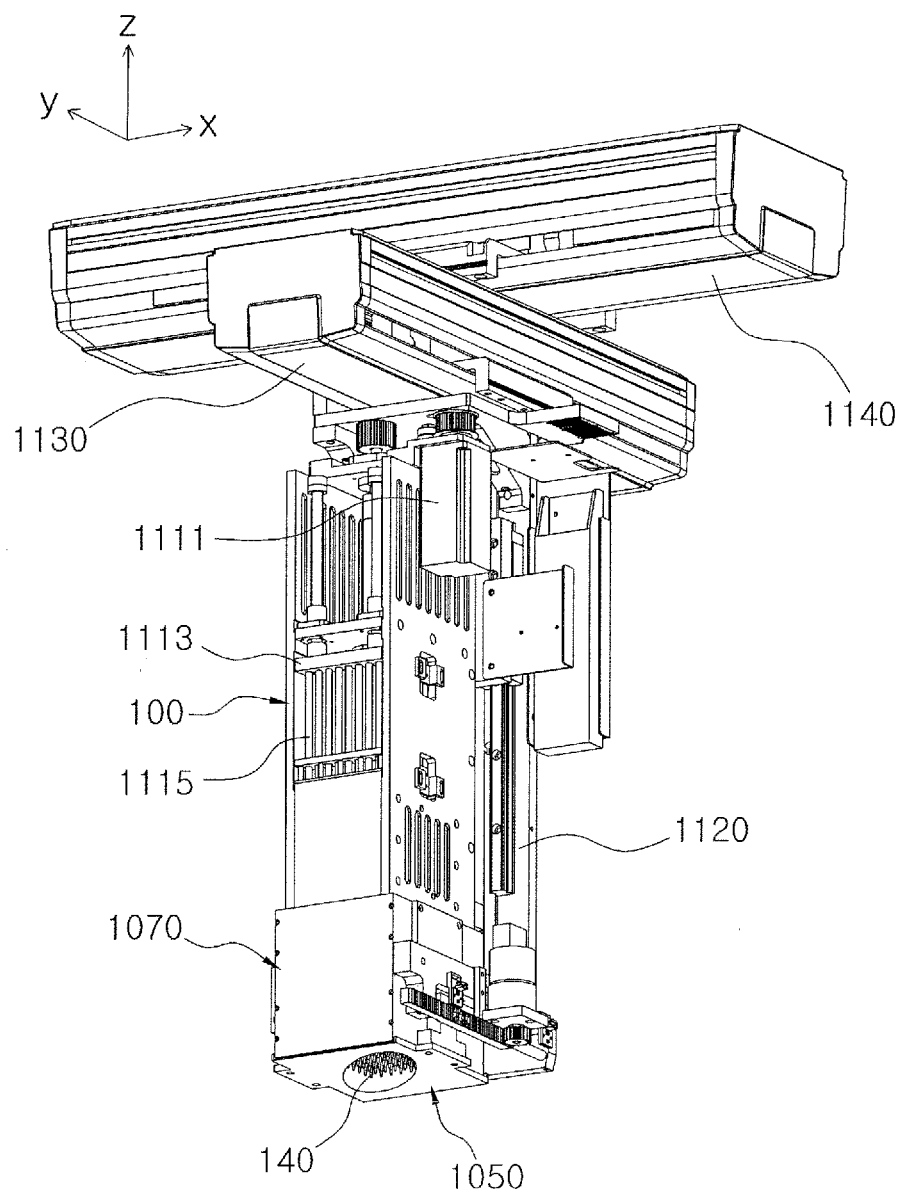
FIGS. 36, 37 and 38 are perspective views showing a fifth embodiment of the present invention.
Figure 37:
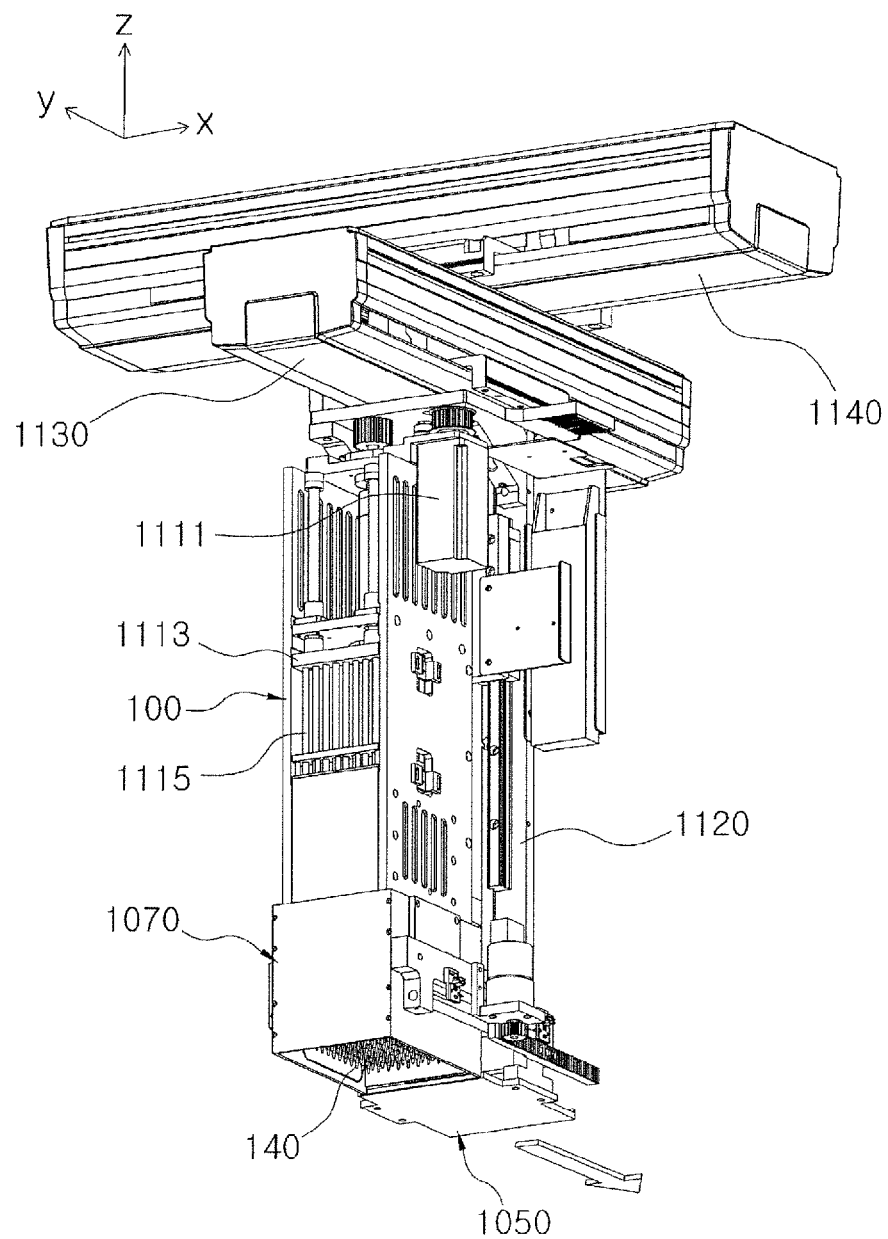
Figure 38:
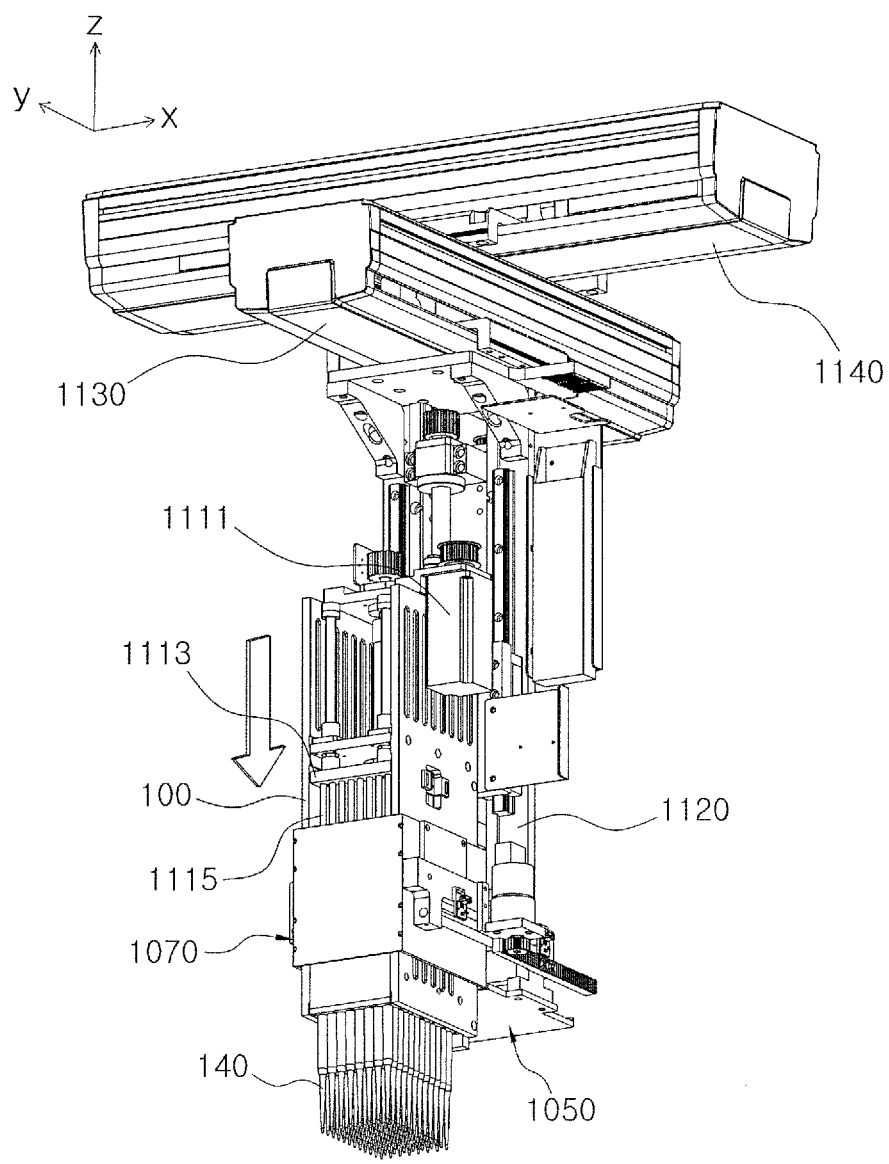
Figure 39:
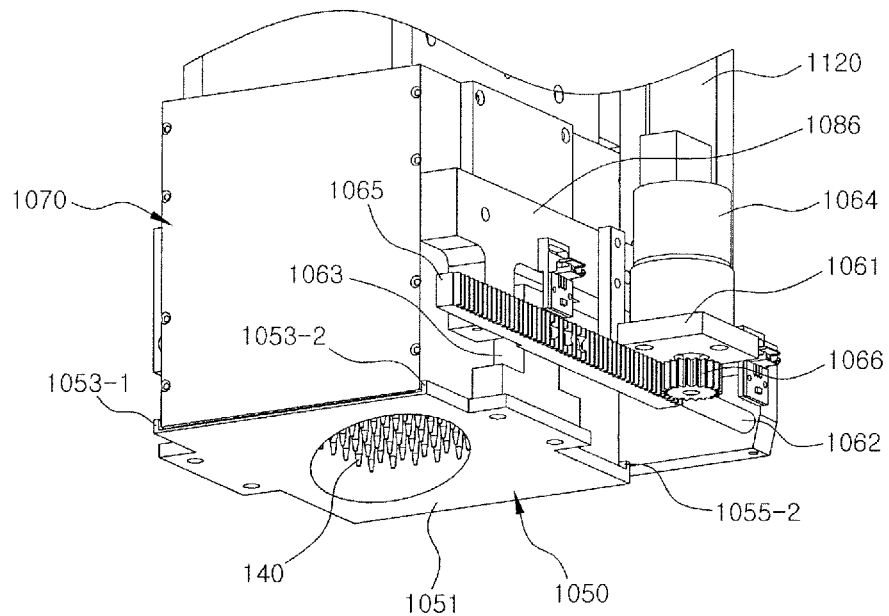
FIGS. 39 and 40 are perspective views of main parts of FIGS. 36 and 37.
Figure 40:
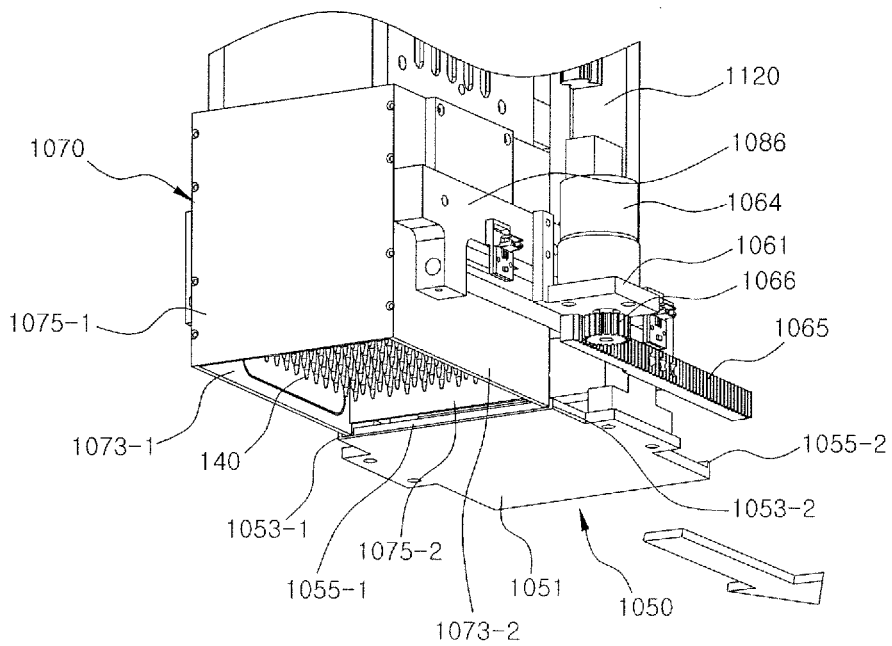

FIGS. 36, 37 and 38 are perspective views showing a fifth embodiment of the present invention, and FIGS. 39 and 40 are perspective views of main parts of FIGS. 36 and 37.

Referring to FIGS. 36 to 38, the fifth embodiment includes a pipette block 100 for isolating a target substance from a plurality of biological samples. The pipette block 100 is disposed at a pipette block supporter 1120 so as to be slid up and down.

Although not shown in FIGS. 36 to 38, a pipette block lifting motor 1151 (referring to FIG. 42) is installed at the pipette block supporter 1120 in order to move the pipette block 100 up and down.

Referring to FIGS. 36 to 38, the pipette block supporter 1120 is disposed at a first horizontal guider 1130 for pipette block so as to be horizontally slid in a y-axial direction. The first horizontal guider 1130 for pipette block is disposed at a second horizontal guider 1140 for pipette block so as to be horizontally slid in an x-axial direction. The x-axial direction is at right angles to the y-axial direction. A moving means for moving the pipette block supporter 1120 and the first horizontal guider 1130 for pipette block in the x-axial direction and the y-axial direction is not shown in the drawings.

Referring to FIGS. 36 to 38, a syringe pin holder 1113 is disposed at the pipette block 100 so as to be slid up and down. A plurality of syringe pins 1115 are fixed to the syringe pin holder 1113. Meanwhile, a syringe pin moving motor 1111 for moving the syringe pin holder 1113 up and down is fixed to the pipette block 100.

Referring to FIGS. 36 to 38, a plurality of pipettes 140 are installed at a lower end of the pipette block 100.

Referring to FIGS. 36 to 40, the fifth embodiment includes a solution drip tray 1050. The solution drip tray 1050 is disposed so as to be spaced apart from lower ends of the plurality of pipettes 140 and also to be movable to a position where the solution drip tray 1050 can receive solution drips from the plurality of pipettes 140. Further, the solution drip tray 1050 is also movable to another position where the solution drip tray 1050 can avoid in contact with plurality of pipettes 140 when the pipette block 100 is moved down. A solution drip tray moving means for moving the solution drip tray 1050 between the above-mentioned positions will be described later.

Referring to FIG. 40, the solution drip tray 1050 is provided with a lower plate 1051 for solution drip tray. The lower plate 1051 for solution drip tray has a sufficient surface area in order to receive all of the solution drips from the plurality of pipettes 140.

Referring to FIG. 40, along edge portions of an upper surface of the lower plate 1051 for solution drip tray, there are uprightly disposed a first tightly-contacting plate 1053-1 for solution drip tray, a second tightly-contacting plate 1055-1 for solution drip tray, a third tightly-contacting plate 1053-2 for solution drip tray and a fourth tightly-contacting plate 1055-2 for solution drip tray.

Referring to FIGS. 39 and 40, the first tightly-contacting plate 1053-1 for solution drip tray is formed so that an inner surface thereof can be tightly contacted with an outer surface of a first side plate 1073-1 for aerosol prevention part. The second tightly-contacting plate 1055-1 for solution drip tray is formed so that an outer surface thereof can be tightly contacted with an inner surface of a second side plate 1075-1 for aerosol prevention part. The third tightly-contacting plate 1053-2 for solution drip tray is formed so that an inner surface thereof can be tightly contacted with an outer surface of a third side plate 1073-2 for aerosol prevention part. The fourth tightly-contacting plate 1055-2 for solution drip tray is formed so that an inner surface thereof can be tightly contacted with an outer surface of a fourth side plate 1075-2 for aerosol prevention part.

Referring to FIGS. 36 to 40, the fifth embodiment includes a box-shaped aerosol prevention part 1070 which is fixedly installed at a desired vertical position so that an inner surface of an upper end of the aerosol prevention part 1070 is tightly contacted with an outer surface of the pipette block 100 and a lower end thereof is tightly contacted with the solution drip tray 1050, when the pipette block 100 is moved upward. The aerosol prevention part 1070 is closely contacted with the solution drip tray 1050 which is moved to a position for receiving the solution drips, such that portions of the pipettes 140, which are wetted with the solution containing the target substance, can be blocked from the outside. Since the aerosol prevention part 1070 is closely contacted with the solution drip tray 1050 so that the portions of the pipettes 140 wetted with the solution containing the target substance are blocked from the outside, air flow passing through the pipette 140 when the pipette block 100 is moved horizontally is not generated. Therefore, it is prevented that aerosol is generated from the solution containing the target substance stained on the outer surface of one of the pipettes 140 when the pipette block 100 is moved horizontally and thus attached on outer surfaces of the rest pipettes 140.

Referring to FIGS. 39 and 40, the aerosol prevention part 1070 includes a first side plate 1073-1 for aerosol prevention part, a second side plate 1075-1 for aerosol prevention part, a third side plate 1073-2 for aerosol prevention part and a fourth side plate 1075-2 for aerosol prevention part. Typically, the aerosol prevention part 1070 is formed into a quadrangular box shape.

Referring to FIGS. 39 and 40, a fixing block 1086 for aerosol prevention part is fixed to the pipette block supporter 1120. As the third side plate 1073-2 for aerosol prevention part is fixed to the fixing block 1086 for aerosol prevention part, the aerosol prevention part 1070 is fixedly disposed at a desired vertical position. Meanwhile, the first side plate 1073-1 for aerosol prevention part is disposed to be faced with the third side plate 1073-2 for aerosol prevention part, and the second side plate 1075-1 for aerosol prevention part is disposed to be faced with the fourth side plate 1075-2 for aerosol prevention part. The fourth side plate 1075-2 for aerosol prevention part is disposed so that a lower end thereof is located at an upper side than a lower end of the second side plate 1075-1 for aerosol prevention part. Meanwhile, an outer side surface of the first side plate 1073-1 for aerosol prevention part is tightly contacted with an inner side surface of the first tightly-contacting plate 1053-1 for solution drip tray, an inner side surface of the second side plate 1075-1 for aerosol prevention part is tightly contacted with an outer side surface of the second tightly-contacting plate 1055-1 for solution drip tray, an outer side surface of the third side plate 1073-2 for aerosol prevention part is tightly contacted with an inner side surface of the third tightly-contacting plate 1053-2 for solution drip tray, and an outer side surface of the fourth side plate 1075-2 for aerosol prevention part is tightly contacted with an inner side surface of the fourth tightly-contacting plate 1055-2 for solution drip tray, thereby enhancing air tightness between the solution drip tray 1050 and the aerosol prevention part 1070.

Hereinafter, the solution drip tray moving means will be described.

Referring to FIGS. 39 and 40, a solution drip tray supporter 1061 is connected to the fixing block 1086 for aerosol prevention part.

Referring to FIGS. 39 and 40, a guiding rod 1062 for solution drip tray is disposed between the fixing block 1086 for aerosol prevention part and the pipette block supporter 1120. A solution drip tray slider 1063 is installed at the guiding rod 1062 for solution drip tray so as to be horizontally moved along the guiding rod 1062 for solution drip tray.

Referring to FIGS. 39 and 40, a solution drip tray moving motor 1064 is fixed to the solution drip tray supporter 1061. A pinion 1066 is rotatably connected to the solution drip tray moving motor 1064. Meanwhile, a rack 1065 engaged with the pinion 1066 is fixed to the solution drip tray slider 1063. Therefore, if the pinion 1066 is rotated by the solution drip tray moving motor 1064, the solution drip tray slider 1063 is horizontally moved along the guiding rod 1062 for solution drip tray.

Referring to FIGS. 39 and 40, the lower plate 1051 for solution drip tray is fixed to the solution drip tray slider 1063. Therefore, as the solution drip tray slider 1063 is horizontally moved, the solution drip tray 1050 is also moved horizontally. Meanwhile, the solution drip tray 1050 is installed so that the lower plate 1051 for solution drip tray is moved along the same horizontal plane when the solution drip tray slider 1063 is moved. Since the lower plate 1051 for solution drip tray is moved along the same horizontal plane, the air flow generated by the movement of the lower plate 1051 for solution drip tray is minimized.

Sixth Embodiment

A sixth embodiment relates to another automatic purification apparatus for isolating a target substance from a plurality of biological samples.

Figure 41:
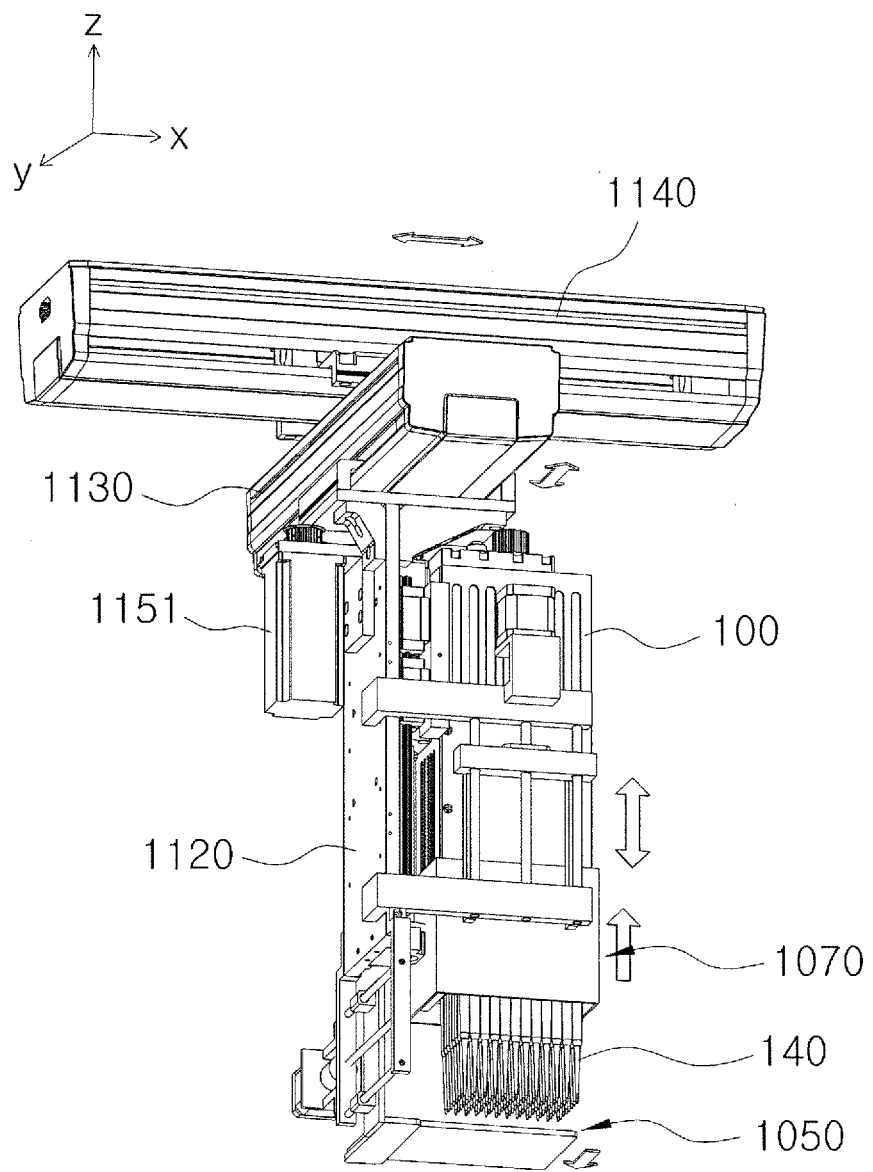
FIGS. 41 and 42 are perspective views showing a sixth embodiment of the present invention.
Figure 42:
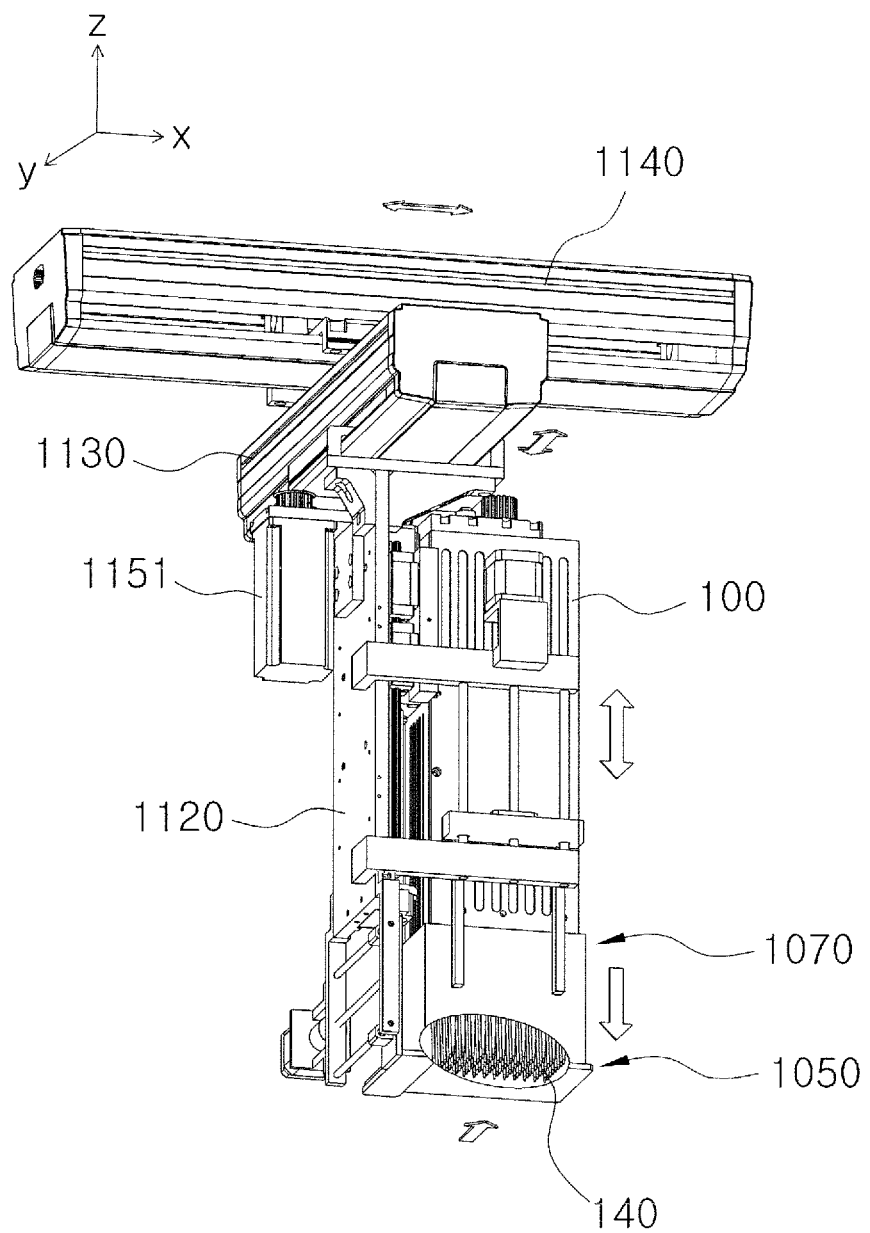
Figure 43:
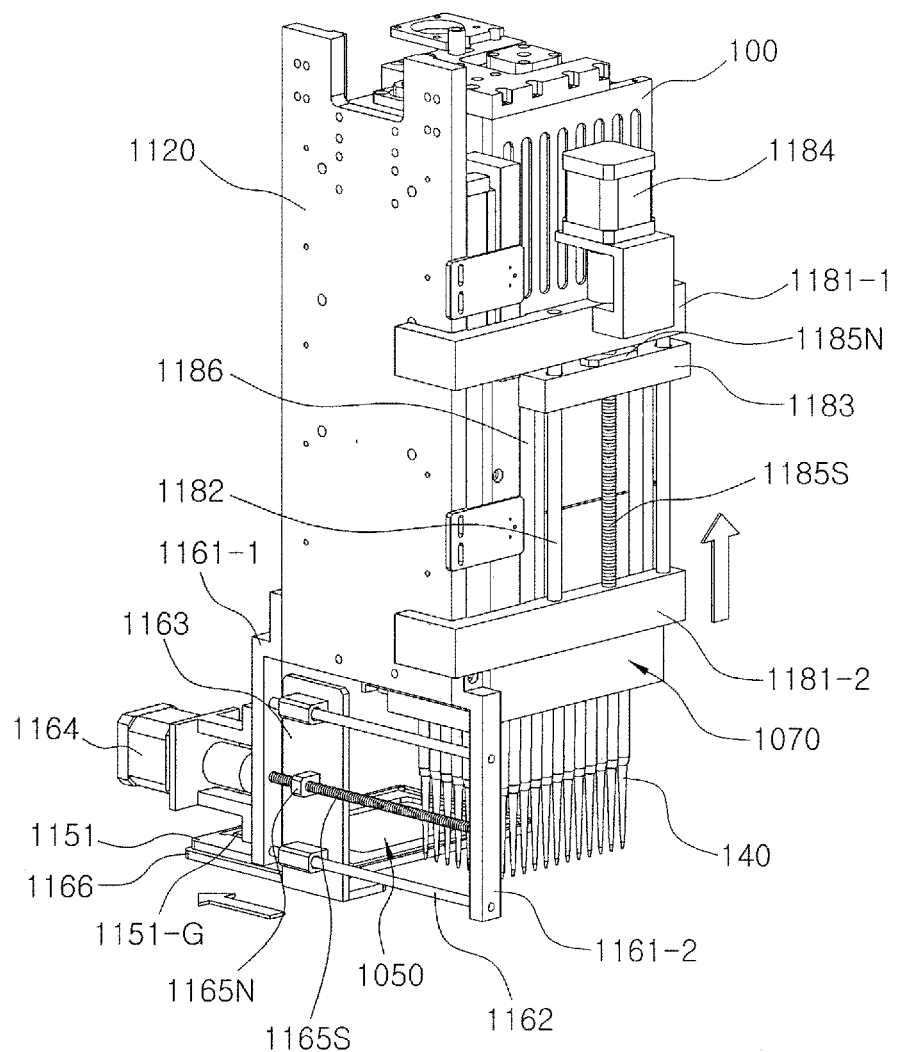
FIGS. 43 and 44 are perspective views of main parts according to the sixth embodiment of the present invention.
Figure 44:
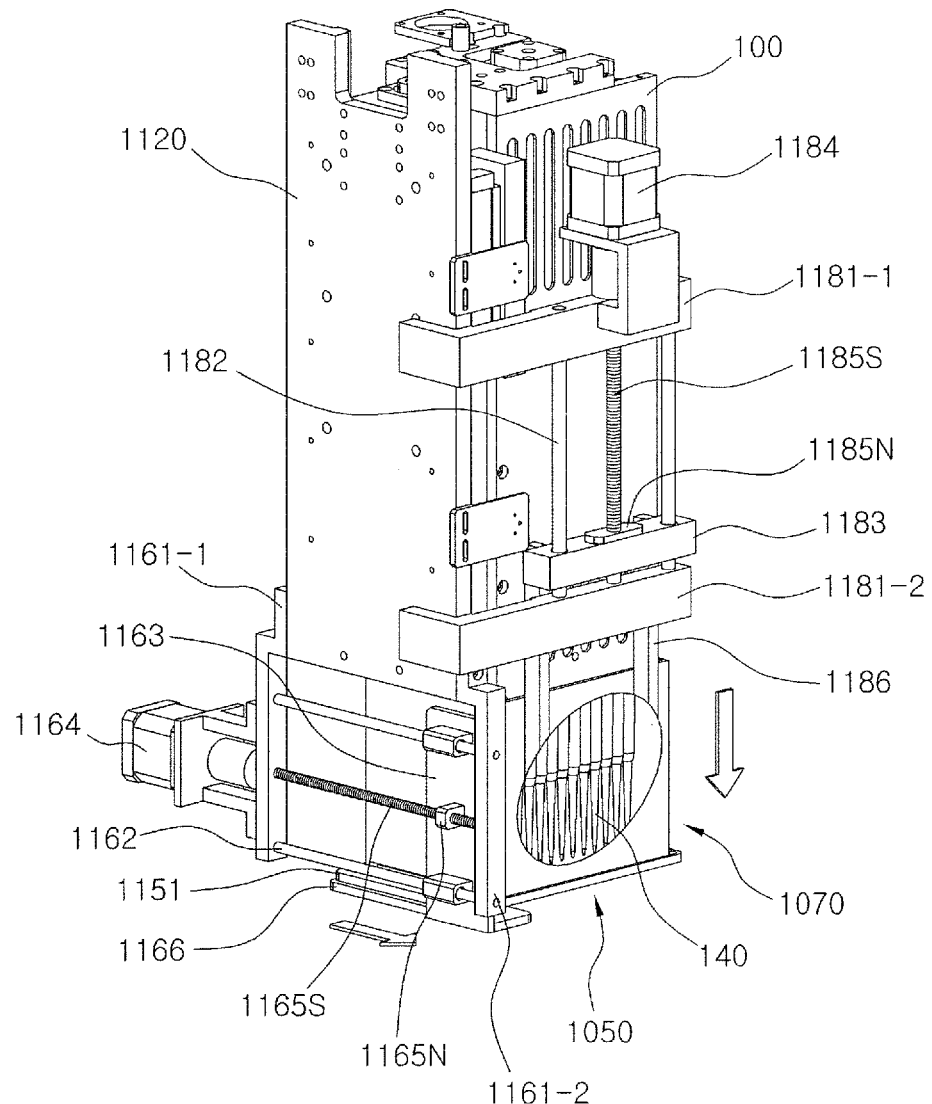

FIGS. 41 and 42 are perspective views showing a sixth embodiment of the present invention, and FIGS. 43 and 44 are perspective views of main parts according to the sixth embodiment of the present invention.

Referring to FIGS. 41 and 42, the sixth embodiment includes a pipette block 100 for isolating a target substance from a plurality of biological samples. The pipette block 100 is installed at a pipette block supporter 1120 so as to be slid upward.

Referring to FIGS. 41 and 42, a pipette block lifting motor 1151 for moving the pipette block 100 up and down is installed at the pipette block supporter 1120.

Referring to FIGS. 41 and 42, the pipette block supporter 1120 is disposed at a first horizontal guider 1130 for pipette block so as to be horizontally slid in a y-axial direction. The first horizontal guider 1130 for pipette block is disposed at a second horizontal guider 1140 for pipette block so as to be horizontally slid in an x-axial direction. The x-axial direction is at right angles to the y-axial direction. A moving means for moving the pipette block supporter 1120 and the first horizontal guider 1130 for pipette block in the x-axial direction and the y-axial direction is not shown in the drawings.

Referring to FIGS. 41 and 42, a plurality of pipettes 140 are installed at a lower portion of the pipette block 100.

Referring to FIGS. 41 to 44, the sixth embodiment includes a solution drip tray 1050. The solution drip tray 1050 is disposed so as to be spaced apart from lower ends of the plurality of pipettes 140 and also to be movable to a position where the solution drip tray 1050 can receive solution drips from the plurality of pipettes 140. Further, the solution drip tray 1050 is also movable to another position where the solution drip tray 1050 can avoid in contact with plurality of pipettes 140 when the pipette block 100 is moved down. A solution drip tray moving means for moving the solution drip tray 1050 between the above-mentioned positions will be described later.

Referring to FIG. 43, the solution drip tray 1050 is provided with a lower plate 1151 for solution drip tray. The lower plate 1151 for solution drip tray has a sufficient surface area in order to receive all of the solution drips from the plurality of pipettes 140. An insertion groove 1151-G formed in a closed curve is formed in an edge portion of an upper surface of the lower plate 1151 for solution drip tray.

Referring to FIGS. 41 and 42, the sixth embodiment includes an aerosol prevention part 1070 which is disposed to be movable in an up and down direction of the pipette block 100. The aerosol prevention part 1070 is closely contacted with the solution drip tray 1050 which is moved to a position where the solution drip tray 1050 can receive the solution drips, such that portions of the pipettes 140, which are wetted with the solution containing the target substance, can be blocked from the outside. Since the aerosol prevention part 1070 is closely contacted with the solution drip tray 1050 so that the portions of the pipettes 140 wetted with the solution containing the target substance are blocked from the outside, air flow passing through the pipettes 140 when the pipette block 100 is moved horizontally is not generated. Therefore, it is prevented that aerosol is generated from the solution containing the target substance stained on the outer surface of one of the pipette 140 when the pipette block 100 is moved horizontally and thus attached on outer surfaces of the rest pipettes 140. An aerosol prevention part moving means for moving the aerosol prevention part 1070 with respect to the pipette block 100 will be described later.

Referring to FIGS. 41 and 43, the aerosol prevention part 1070 is formed into a box shape, such that an inner surface of an upper end of the aerosol prevention part 1070 is tightly contacted with an outer surface of the pipette block 100, and a lower end thereof is tightly contacted with an upper surface of the solution drip tray 1050 when the aerosol prevention part 1070 is moved down. That is, the aerosol prevention part 1070 may be formed into the box shape which encloses outer surfaces of the pipette block 100 so as to be movable up and down. Meanwhile, the aerosol prevention part 1070 is formed so that a lower end thereof can be inserted into an insertion groove 1151-G (referring to FIG. 43) of the solution drip tray 1050. Since the lower end of the aerosol prevention part 1070 is inserted into the insertion groove 1151-G (referring to FIG. 43) of the solution drip tray 1050, air tightness between the solution drip tray 1050 and the aerosol prevention part 1070 is enhanced.

Hereinafter, the solution drip tray moving means will be described.

Referring to FIGS. 43 and 44, two first supporting parts 1161-1 and 1161-2 for solution drip tray, which are spaced apart from each other, are installed at the lower end of the pipette block supporter 1120.

Referring to FIGS. 43 and 44, a guiding rod 1162 for solution drip tray is disposed between the first supporting parts 1161-1 and 1161-2 for solution drip tray. A solution drip tray slider (not designated by a reference numeral) is installed at the guiding rod 1162 for solution drip tray so as to be horizontally moved along the guiding rod 1162 for solution drip tray.

Referring to FIGS. 43 and 44, the solution drip tray slider (not designated by a reference numeral) is fixed to a moving plate 1163 for solution drip tray disposed between the first supporting parts 1161-1 and 1161-2 for solution drip tray.

Referring to FIGS. 43 and 44, a moving motor 1164 for solution drip tray is fixed to the first supporting part 1161-1 for solution drip tray. A ball screw 1165S for solution drip tray is rotatably connected to the moving motor 1164 for solution drip tray. The ball screw 1165S for solution drip tray is rotatably supported to the first supporting parts 1161-1 and 1161-2 for solution drip tray.

Referring to FIGS. 43 and 44, a ball nut 1165N for solution drip tray is inserted onto the ball screw 1165S for solution drip tray. The ball nut 1165N for solution drip tray is formed with a female thread corresponding to a male thread of the ball screw 1165S for solution drip tray. Meanwhile, the ball nut 1165N for solution drip tray is fixed to the moving plate 1163 for solution drip tray. Therefore, if the ball screw 1165S for solution drip tray is rotated by the solution drip tray moving motor 1164, the moving plate 1163 for solution drip tray is horizontally moved along the guiding rod 1162 for solution drip tray.

Referring to FIGS. 43 and 44, a second supporting part 1166 for solution drip tray is fixed to the moving plate 1163 for solution drip tray. The solution drip tray 1050 is fixed to an upper side surface of the second supporting part 1166 for solution drip tray. Therefore, as the moving plate 1163 for solution drip tray is horizontally moved, the solution drip tray 1050 is also moved horizontally. Meanwhile, the solution drip tray 1050 is installed so that the lower plate 1151 for solution drip tray is moved along the same horizontal plane when the moving plate 1163 for solution drip tray is moved. Since the lower plate 1151 for solution drip tray is moved along the same horizontal plane, the air flow generated by the movement of the lower plate 1151 for solution drip tray is minimized.

Hereinafter, the aerosol prevention part moving means will be described.

Referring to FIGS. 43 and 44, two first supporting parts 1181-1 and 1181-2 for aerosol prevention part are connected to a side surface of the pipette block supporting part 1120 so as to be spaced apart from each other in an up and down direction.

Referring to FIGS. 43 and 44, a guiding rod 1182 for aerosol prevention part is disposed between the first supporting parts 1181-1 and 1181-2 for aerosol prevention part. A moving block 1183 for aerosol prevention part is installed at the guiding rod 1182 for aerosol prevention part so as to be moved up and down along the guiding rod 1182 for aerosol prevention part.

Referring to FIGS. 43 and 44, an aerosol prevention part moving motor 1184 is fixed to the first supporting part 1181-1 for aerosol prevention part, and a ball screw 1185S for aerosol prevention part is rotatably connected to the aerosol prevention part moving motor 1184. The ball screw 1185S for aerosol prevention part is rotatably supported by the first supporting parts 1181-1 and 1181-2 for aerosol prevention part.

Referring to FIGS. 43 and 44, a ball nut 1185N for aerosol prevention part is inserted onto the ball screw 1185S for aerosol prevention part. The ball nut 1185N for aerosol prevention part is formed with a female thread corresponding to a male thread of the ball screw 1185S for aerosol prevention part. Meanwhile, the ball nut 1185N for aerosol prevention part is fixed to the moving block 1183 for aerosol prevention part. Therefore, if the ball screw 1185S for aerosol prevention part is rotated by the aerosol prevention part moving motor 1184, the moving block 1183 for aerosol prevention part is moved up and down along the guiding rod 1182 for aerosol prevention part.

Referring to FIGS. 43 and 44, an upper end of a second supporting part 1186 for aerosol prevention part is fixed to the moving block 1183 for aerosol prevention part, and the aerosol prevention part 1070 is fixed to a lower end of the second supporting part 1186 for aerosol prevention part. Therefore, as the moving block 1183 for aerosol prevention part is moved down, the aerosol prevention part 1070 is also moved down. Meanwhile, the aerosol prevention part 1070 is installed so that the four side plates for aerosol prevention part of the aerosol prevention part 1070 are respectively moved along the same vertical surfaces when the moving block 1183 for aerosol prevention part is moved. Since the four side plates for aerosol prevent part are respectively moved along the same vertical surfaces, the air flow generated by the movement of the four side plates for aerosol prevent part is minimized.

Seventh Embodiment

A seventh embodiment relates to yet another automatic purification apparatus for isolating a target substance from a plurality of biological samples.

Figure 45:
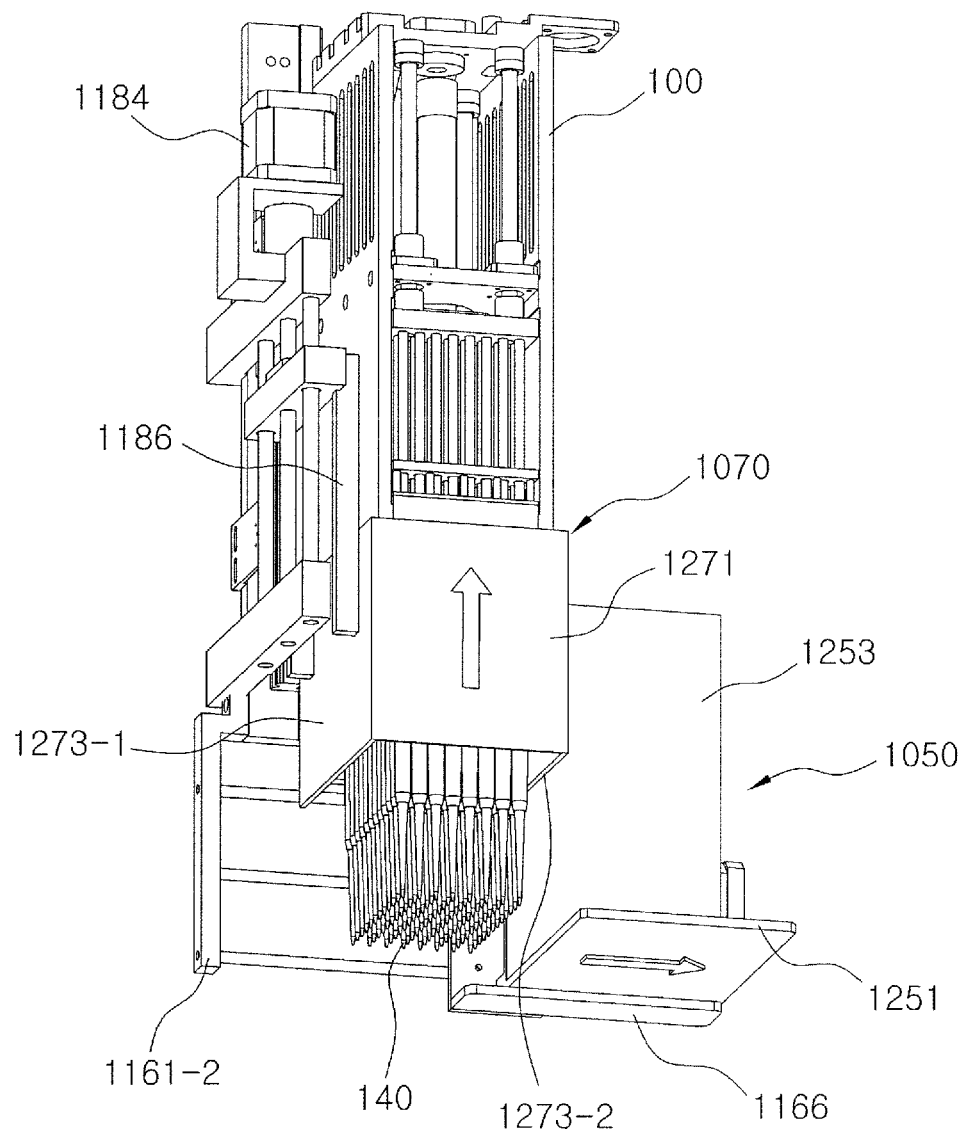
FIGS. 45 and 46 are perspective views of main parts according to a seventh embodiment of the present invention.
Figure 46:
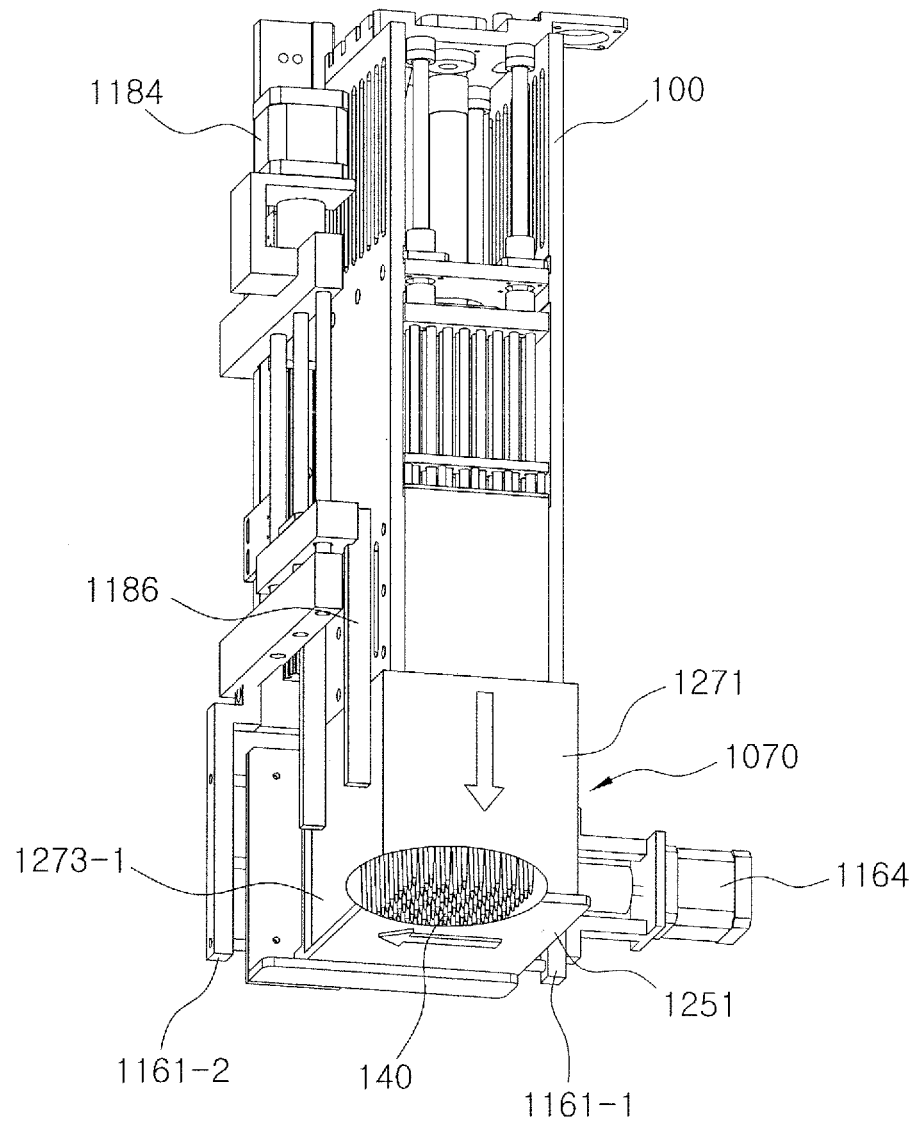

FIGS. 45 and 46 are perspective views of main parts according to the seventh embodiment of the present invention.

The seventh embodiment is the same as the sixth embodiment except the solution drip tray 1050 and the aerosol prevention part 1070. Therefore, the same reference numerals and technical terms are used for the same elements.

Referring to FIG. 45, the solution drip tray 1050 has a lower plate 1251 for solution drip tray and a side plate 1253 for solution drip tray.

Referring to FIGS. 45 and 46, the lower plate 1251 for solution drip tray is formed into a flat plate and disposed horizontally. The lower plate 1251 for solution drip tray is fixed to the second supporting part 1166 for solution drip tray. The lower plate 1251 for solution drip tray is disposed to be moved along the same horizontal plane when the second supporting part 1166 for solution drip tray is moved. Therefore, the air flow generated by the movement of the lower plate 1251 for solution drip tray is minimized. Like in the sixth embodiment, the lower plate 1251 for solution drip tray has a sufficient surface area in order to receive all of the solution drips from the plurality of pipettes 140. Meanwhile, although not shown in the drawings, an edge portion of an upper surface of the lower plate 1251 for solution drip tray is formed with an insertion groove (not shown) in which a lower end of the aerosol prevention part 1070 is inserted.

Referring to FIGS. 45 and 46, the side plate 1253 for solution drip tray is formed into a flat plate and uprightly disposed at an edge portion of the lower plate 1251 for solution drip tray. The side plate 1253 for solution drip tray is disposed to be moved along the same vertical surface when the second supporting part 1166 for solution drip tray is moved, and thus the air flow generated by the movement of the side plate 1253 for solution drip tray is minimized. Accordingly, the solution drip tray 1050 has an "L"-shaped longitudinal cross section. The side plate 1253 for solution drip tray is disposed so that an upper end thereof is tightly contacted with a side surface of the pipette block 100 when the solution drip tray 1050 is moved.

Referring to FIG. 45, the aerosol prevention part 1070 has three side plates 1271, 1273-1 and 1273-2 for aerosol prevention part. The three side plates 1271, 1273-1 and 1273-2 for aerosol prevention part are connected with each other so as to provide a "U"-shaped transverse cross section. The side plate 1273-1 for aerosol prevention part is fixedly connected to a lower portion of the second supporting part 1186 for aerosol prevention part. Meanwhile, the aerosol prevention part 1070 is disposed so that the three side plates 1271, 1273-1 and 1273-2 for aerosol prevention part are respectively moved along the same vertical surfaces when the aerosol prevention part 1070 is moved down. Since the three side plates 1271, 1273-1 and 1273-2 for aerosol prevention part are respectively moved along the same vertical surfaces, the air flow generated by the movement of the three side plates 1271, 1273-1 and 1273-2 for aerosol prevention part is minimized.

Referring to FIG. 46, the aerosol prevention part 1070 is installed so that an upper inner surface thereof is tightly contacted with the outer surface of the pipette block 100 and a lower end thereof is inserted into the insertion groove (not shown) of the lower plate 1251 for solution drip tray when the aerosol prevention part 1070 is moved down. Further, the aerosol prevention part 1070 is also installed so that both side ends of opened outer surface thereof, i.e., exposed side ends of the two side plates 1273-1 and 1273-2 for aerosol prevention part are tightly contacted with the side plate 1253 for solution drip tray when the aerosol prevention part 1070 is moved down.

Eighth Embodiment

An eighth embodiment relates to yet another automatic purification apparatus for isolating a target substance from a plurality of biological samples.

Referring to FIGS. 45 and 46, a solution drip tray and an aerosol prevention part of the eighth embodiment are the same as the solution drip tray 1050 and the aerosol prevention part 1070 of the seventh embodiment. Therefore, the same reference numerals and technical terms are used for the same elements. In the eighth embodiment, the aerosol prevention part 1070 is fixedly installed at a vertical position in which an upper inner surface thereof can be tightly contacted with an outer surface of the pipette block 100 when the purification block 110 is moved upward. Therefore, the eighth embodiment does not include the aerosol prevention part moving means for moving up and down the aerosol prevention part 1070. Further, unlike in the seventh embodiment, an edge portion of an upper surface of the lower plate 1251 for solution drip tray is not formed with the insertion groove (not shown) in which the lower end of the aerosol prevention part 1070 is inserted. Thus, the lower plate 1251 for solution drip tray of the eighth embodiment may be formed with a tightly-contacting plate equivalent to the tightly-contacting plates 1053-1, 1053-2, 1055-1 and 1055-2 for solution drip tray (referring to FIG. 40) of the fifth embodiment. The other matters are the same as in the seventh embodiment.

Ninth Embodiment

A ninth embodiment relates to yet another automatic purification apparatus for isolating a target substance from a plurality of biological samples.

Figure 47:
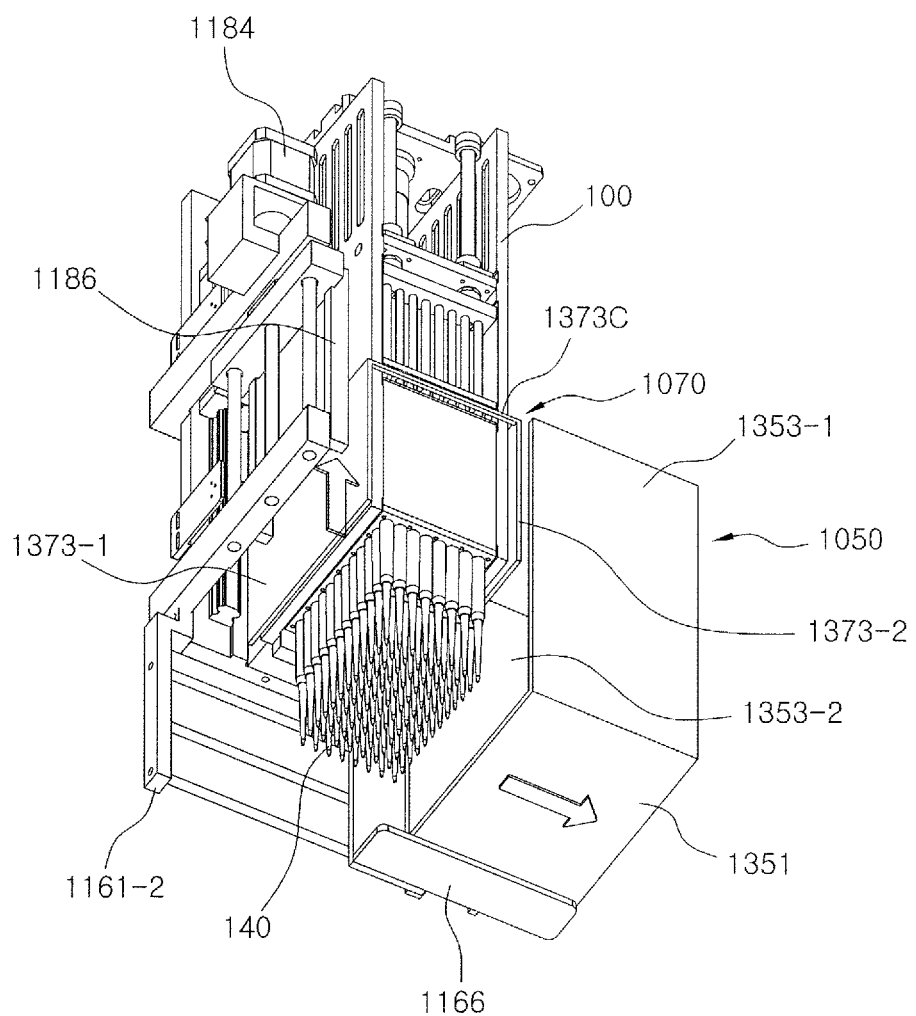
FIGS. 47 and 48 are perspective views of main parts according to a ninth embodiment of the present invention.
Figure 48:
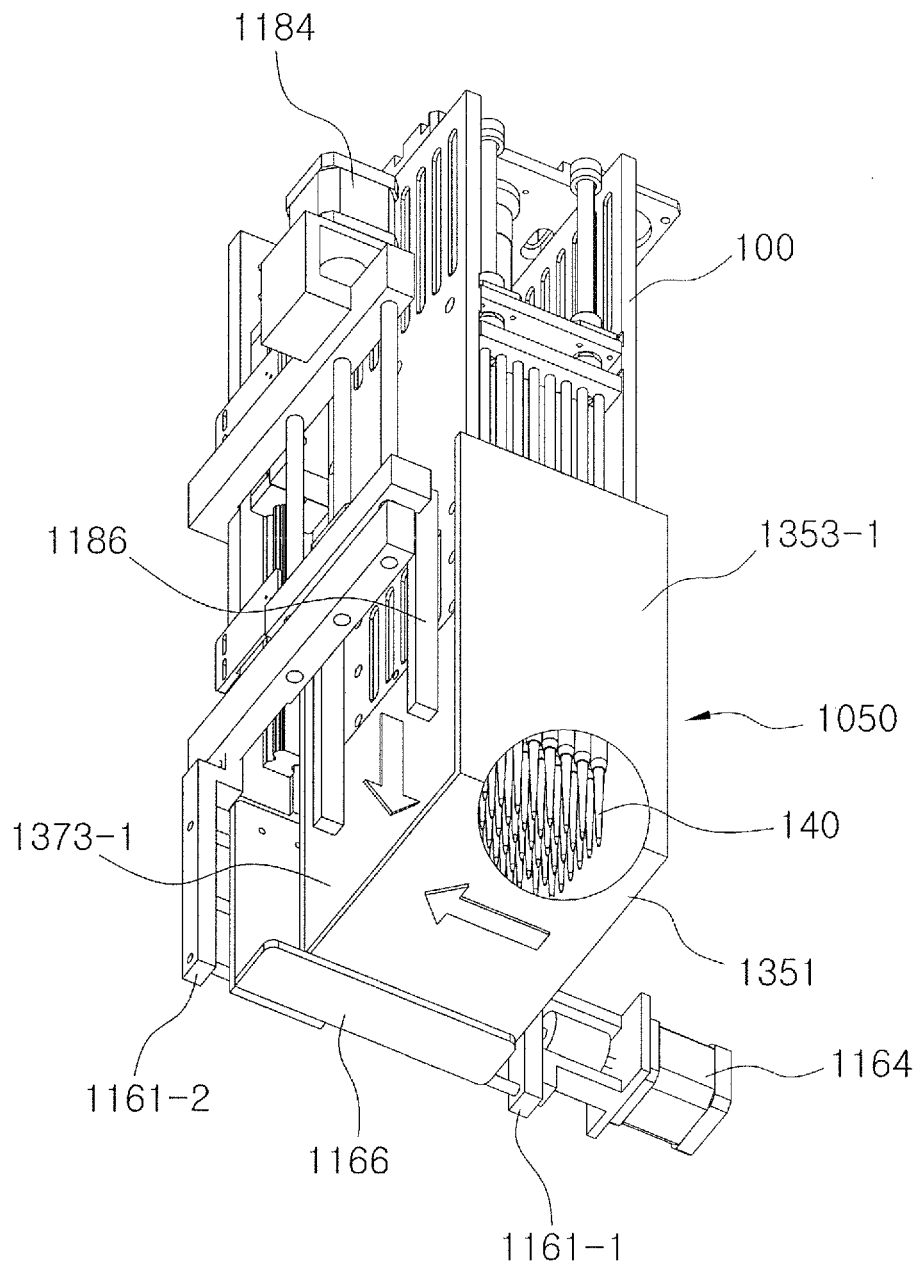

FIGS. 47 and 48 are perspective views of main parts according to the ninth embodiment of the present invention.

The ninth embodiment is the same as the sixth embodiment except the solution drip tray 1050 and the aerosol prevention part 1070. Therefore, the same reference numerals and technical terms are used for the same elements.

Referring to FIG. 47, the solution drip tray 1050 has a lower plate 1351 for solution drip tray and two side plates 1353-1 and 1353-2 for solution drip tray.

Referring to FIGS. 47 and 48, the lower plate 1351 for solution drip tray is formed into a flat plate and disposed horizontally. The lower plate 1351 for solution drip tray is fixed to the second supporting part 1166 for solution drip tray. The lower plate 1351 for solution drip tray is disposed so as to be moved along the same horizontal plane when the second supporting part 1166 for solution drip tray is moved. Therefore, the air flow generated by the movement of the lower plate 1351 for solution drip tray is minimized. Like in the sixth embodiment, the lower plate 1351 for solution drip tray has a sufficient surface area in order to receive all of the solution drips from the plurality of pipettes 140. Meanwhile, although not shown in the drawings, the lower plate 1351 for solution drip tray is formed with two insertion grooves (not shown) which are straightly arranged to be spaced apart from each other and in which lower ends of two side plates 1373-1 and 1373-2 for aerosol prevention part are inserted so as to enhance the air-tightness.

Referring to FIGS. 47 and 48, the two side plates 353-1 and 353-2 for solution drip tray are uprightly disposed at both edge portions of the lower plate 351 for solution drip tray. The two side plates 1353-1 and 1353-2 for solution drip tray are disposed to be respectively moved along the same vertical surfaces when the second supporting part 1166 for solution drip tray is moved, and thus the air flow generated by the movement of the two side plates 1353-1 and 1353-2 for solution drip tray is minimized. Accordingly, the solution drip tray 1050 has a "U"-shaped longitudinal cross section. The two side plates 1353-1 and 1353-2 for solution drip tray are disposed so that upper ends thereof are tightly contacted with side surfaces of the pipette block 100 when the solution drip tray 1050 is moved.

Referring to FIG. 47, the aerosol prevention part 1070 has two side plates 1373-1 and 1373-2 for aerosol prevention part. Upper ends of the two side plates 1373-1 and 1373-2 for aerosol prevention part are connected with each other through a side plate connection part 1373C so that the two side plates 1373-1 and 1373-2 for aerosol prevention part are parallelly faced with each other and the pipette block 100 is interposed therebetween.

Referring to FIGS. 47 and 48, the side plate 1373-1 for aerosol prevention part is fixedly connected to a lower end of the second supporting part 1186 for aerosol prevention part. Meanwhile, the aerosol prevention part 1070 is disposed so that the two side plates 1373-1 and 1373-2 for aerosol prevention part are respectively moved along the same vertical surfaces when the aerosol prevention part 1070 is moved down. Since the two side plates 1373-1 and 1373-2 for aerosol prevention part are respectively moved along the same vertical surfaces, the air flow generated by the movement of the two side plates 1373-1 and 1373-2 for aerosol prevention part is minimized.

Referring to FIGS. 47 and 48, the aerosol prevention part 1070 is installed so that upper inner surfaces of the two side plates 1373-1 and 1373-2 for aerosol prevention part are tightly contacted with the outer surface of the pipette block 100 and lower ends thereof is inserted into the insertion groove (not shown) of the lower plate 1351 for solution drip tray when the aerosol prevention part 1070 is moved down. Further, the aerosol prevention part 1070 is also installed so that both side ends of the two side plates 1373-1 and 1373-2 for aerosol prevention part are tightly contacted with the two side plates 1353-1 and 1353-2 for solution drip tray when the aerosol prevention part 1070 is moved down.

Tenth Embodiment

A tenth embodiment relates to yet another automatic purification apparatus for isolating a target substance from a plurality of biological samples.

Referring to FIGS. 47 and 48, a solution drip tray and an aerosol prevention part of the tenth embodiment have the same structure as those of ninth embodiment. Therefore, the same reference numerals and technical terms are used for the same elements. In the tenth embodiment, the aerosol prevention part 1070 is fixedly installed at a vertical position in which an upper inner surface thereof can be tightly contacted with the outer surface of the pipette block 100 when the pipette block 100 is moved upward. Therefore, the tenth embodiment does not include the aerosol prevention part moving means for moving up and down the aerosol prevention part 1070. Further, unlike in the ninth embodiment, the lower plate 1351 for solution drip tray is not formed with the two insertion grooves (not shown) which are formed in edge portions of an upper surface thereof. Thus, the lower plate 1351 for solution drip tray of the tenth embodiment may be formed with a tightly-contacting plate equivalent to the tightly-contacting plates 1053-1, 1053-2, 1055-1 and 1055-2 for solution drip tray (referring to FIG. 40) of the ninth embodiment. The other matters are the same as in the ninth embodiment.

INDUSTRIAL APPLICABILITY

According to the present invention as described above, it is possible to move up and down a magnet mounting part and a heating part, thereby applying and releasing the magnetic field and also controlling the temperature.

And since a plurality of unit well inserting grooves formed in the magnet mounting part are formed so as to enclose a lower portion of each unit well of a multi-well plate, it is possible to improve the reaction efficiency.

According to the present invention, it is possible to prevent solution drips undesirably fallen from the plurality of pipettes from being introduced into the unit wells of the multi-well plate, thereby stably isolating the target substance.

Further, it is possible to maintain nucleic acid received in the target substance receiving tube and the diagnostic kit or diagnostic reagent received in the target substance diagnosing tube at a low temperature, e.g., 3~5° C.

Further, it is possible to prevent the multi-well plate from being separated upward when the pipettes installed at the pipette block is moved up and down so as to access to the unit wells of the multi-well plate.

Furthermore, it is possible to automatically mix the purified nucleic acid and the diagnostic kit or diagnostic reagent received in the target substance diagnosing tube using the plurality of pipettes.

Further, it is possible to perform the expression and purification of protein as the target substance from the biological samples using the plurality of pipettes installed at the pipette block.

Further, since the heat transfer is occurred from the heating part to the auxiliary heating part enclosing the particular unit well of the multi-well plate, it is possible to efficiently heat the particular unit well of the multi-well plate.

Further, since the contamination preventing device can block an upper end of the target substance receiving tube, the aerosol generated from purified nucleic acid can be prevented from being spread to the outside of the target substance receiving tube when the purified nucleic acid is discharged from the plurality of pipettes.

While the present invention has been described with respect to the specific embodiments, it will be apparent to those skilled in the art that various changes and modifications may be made without departing from the spirit and scope of the invention as defined in the following claims.

The invention claimed is:

1. An automatic purification apparatus for isolating a target substance from a plurality of biological samples, comprising:
   a pipette block capable of moving vertically and horizontally and in which a plurality of pipettes for sucking and discharging a fluid material are removably installed;
   a fixed body which supports the pipette block;
   a solution drip tray attached to a solution drip tray moving portion, wherein the solution drip tray moving portion is attached to the fixed body and located at a lower side of the plurality of pipettes installed at the pipette block, and wherein the solution drip tray moving portion moves the solution drip tray horizontally;
   an aerosol prevention portion which is attached to the solution drip tray located at the lower side of the plurality of pipettes so as to enclose portions of the pipettes, which are wetted with a solution containing the target substance, such that the portions of the pipettes can be blocked from the outside;
   a multi-well plate located at a lower side of the pipette block;
   a magnetic field applying part mounted on a base plate, the magnetic field applying part comprises a magnet mounting part on which a magnet is mounted and which is located at a lower side of a particular unit well of the multi-well plate;
   a lifting part which lifts up and down the magnet mounting part to apply and release a magnetic field to the particular unit well; and
   a heating part which is integrally formed with the magnet mounting part.

2. The automatic purification apparatus according to claim 1, further comprising:
   a unit well inserting in an upper surface of the magnet mounting part so that a lower portion of the particular unit well of the multi-well plate is removably inserted, and the base plate is formed comprises a unit well exposing hole so that the lower portion of the particular unit well is inserted in the unit well inserting groove when the magnet mounting part is lifted up.

3. The automatic purification apparatus according to claim 2, wherein the magnet is installed around the unit well inserting groove.

4. The automatic purification apparatus according to claim 1, wherein the heating part is a heat generating film.

5. The automatic purification apparatus according to claim 2, further comprising a pipette rack in which the plurality of pipettes in the pipette block are received, a first tube rack, and a waste liquid container are mounted on the base plate.

6. The automatic purification apparatus according to claim 5, further comprising a cooling block for cooling the first tube rack.

7. A method of extracting a target substance from a biological sample using the automatic purification apparatus according to claim 1, comprising:
   introducing a biological sample to a particular unit well of a multi-well plate;
   adding a mixture comprising distilled water and an expression solution to the particular unit well;
   injecting and mixing a cell extract into the particular unit well;
   heating the particular unit well;
   injecting a first expressed protein into the particular unit well;
   injecting a magnetic particle binding solution containing magnetic particles to the particular unit well;
   applying a magnetic field by the magnetic field applying part to a lower portion of the particular unit well;
   removing the mixture from the particular unit well except for the magnetic particles on which the target substance and impurities are attached;
   injecting a second expression protein into the particular unit well;
   injecting additional magnetic particle binding solution containing magnetic particles to the particular unit well;
   re-applying the magnetic field by the magnetic field applying part to the lower portion of the particular unit well;
   removing the mixture from the particular unit well except for the magnetic particles on which the target substance are attached;
   injecting a washing or an elution solution into the particular unit well;
   re-applying the magnetic field by the magnetic field applying part to the lower portion of the particular unit well; and
   isolating the target substance.

8. An automated method of performing protein expression, purification and isolation using the automatic purification apparatus according to claim 1,
   injecting a biological sample comprising a target DNA protein, an expression solution and cell extract in a particular unit well of the multi-well plate;
   heating the mixture of target DNA, the expression solution and the cell extract for producing expressed protein;
   injecting a mixture of an expressed protein with a magnetic particle binding solution into the particular unit well;
   applying a magnet mounting part to a lower part of the particular unit well to apply a magnetic field;
   injecting a washing solution into the particular unit well for separating the expressed protein from magnetic particles; and
   injecting a elution solution into the particular unit well for isolating a target protein.

9. An automatic purification apparatus for isolating a target substance from a plurality of biological samples, comprising:
   a pipette block capable of moving vertically and horizontally and in which a plurality of pipettes for sucking and discharging a fluid material are removably installed;
   a multi-well plate located at a lower side of the pipette block;
   a magnet mounting part mounted on a base plate, wherein the magnetic mounting part comprises a magnet for applying a magnetic field to a particular unit well of a multi-well plate is mounted, and wherein the magnet mounting part is located at a lower side of the pipette block on a lower side of the particular unit well;
   a lifting part which lifts up and down the magnet mounting part to apply and release the magnetic field to the particular unit well;
   a heating part which is installed at the magnet mounting part to heat the magnet mounting part; and
   an auxiliary heating part in which the particular unit well of the multi-well plate is inserted.

10. The automatic purification apparatus according to claim 9, wherein the auxiliary heating part comprises:
    a first body which is contacted with an outer surface of one side of the particular unit well;
    a second body which is contacted with an outer surface of another side of the particular unit welt; and
    a spring which presses the second body toward the first body so that the outer surface of the particular unit well is contacted with the first and second bodies.

11. The automatic purification apparatus according to claim 9, further comprising
    a unit well inserting groove in an upper surface of the magnet mounting part so that a lower portion of the particular unit well is removably inserted, and
    the base plate comprising a unit well exposing hole so that the lower portion of the particular unit well is inserted in the unit well inserting groove when the magnet mounting part is moved up.

12. The automatic purification apparatus according to claim 9, wherein the heating part is a heat generating film.

13. A method of extracting a target substance from a biological sample using the automatic purification apparatus according to claim 11, comprising:
    mixing the biological sample with a cell lysis solution injected into a particular unit well of the multi-well plate using the pipette block;
    heating the particular unit well using the heating part while the magnet mounting part is lifted up;
    mixing the mixture of the cell lysis solution and the biological sample with a binding solution injected into the particular unit well;
    mixing a mixture of the binding solution with an aqueous dispersion solution of magnetic particles injected into the particular unit well;
    lifting up the magnet mounting part to apply a magnetic field from a magnet to a lower portion of the particular unit well;
    removing the mixture except for the magnetic particles and a substance on the magnetic particles from the mixture attached to a lower inner surface of the particular unit well;
    injecting a washing solution into the particular unit well;
    removing the washing solution mixture except for the magnetic particles comprising the target substance attached to the lower inner surface of the particular unit well;
    injecting a nucleic acid elution solution into the particular unit well; and
    isolating a target substance containing solution except the magnetic particles from the nucleic acid elution solution.

14. The method according to claim 13, wherein the washing solution includes alcohol, and further comprises heating the lower portion of the particular unit well of the multi-well plate using the heating part removing alcohol contained in the washing solution.

15. The method according to claim 13, wherein the method step of obtaining the target substance further comprises injecting the target substance containing solution into a target substance receiving tube or a target substance diagnosing tube.

16. An automatic purification apparatus for isolating a target substance from a plurality of biological samples, comprising:
   a pipette block capable of moving vertically and horizontally and in which a plurality of pipettes for sucking and discharging a fluid material are removably installed;
   a multi-well plate located at a lower side of the pipette block;
   a magnetic field applying part capable of applying a magnetic field to a particular unit well of the multi-well plate;
   a first tube rack capable of receiving a target substance tube; and
   a contamination preventing device to block an upper end of the target substance tube, comprising a cover film having a cut line which is gaped by a pressing force of the plurality of pipettes to allow the lower portions of the pipettes to be passed therethrough, and a film supporter mounted on a base plate,
   wherein the film supporter comprises a settle plate with a through-hole on which the cover film is settled and a horizontal movement preventing plate installed at an upper surface of the settle plate to prevent horizontal movement of the cover film.

17. The automatic purification apparatus according to claim 16, wherein the film supporter comprises a vertical movement preventing plate comprising an exposing hole and attached to an upper surface of the cover film.

18. The automatic purification apparatus according to claim 17, wherein the film supporter comprises a settle plate supporter which is inserted into the first tube rack.

19. The automatic purification apparatus according to claim 16, wherein a foil which can be punched by pressing force of the pipettes is employed between the settle plate and the cover film.

20. The automatic purification apparatus according to claim 16, wherein the first tube rack comprises at least one of a target substance receiving tube and a target substance diagnosing tube.

21. The automatic purification apparatus according to claim 16, further comprising
   a base plate comprising a unit well exposing hole;
   a waste liquid container mounted on the base plate adjacent to the unit well exposing hole with which the base plate is formed to apply the magnetic field to the lower portion of the particular unit well; and
   a second tube rack adjacent to the unit well exposing hole and the waste liquid container.

* * * * *